(12) United States Patent
Goren et al.

(10) Patent No.: US 9,599,575 B2
(45) Date of Patent: Mar. 21, 2017

(54) SYSTEM, A METHOD AND A COMPUTER PROGRAM PRODUCT FOR CAD-BASED REGISTRATION

(75) Inventors: Zvi Goren, Nes Ziona (IL); Nir Ben-David Dodzin, Hod Hasharon (IL)

(73) Assignee: Applied Materials Israel, Ltd., Rehovot (IL)

( * ) Notice: Subject to any disclaimer, the term of this patent is extended or adjusted under 35 U.S.C. 154(b) by 724 days.

(21) Appl. No.: 13/368,305

(22) Filed: Feb. 7, 2012

(65) Prior Publication Data
US 2013/0204569 A1    Aug. 8, 2013

(51) Int. Cl.
*G01N 21/95*    (2006.01)
*G01N 21/956*    (2006.01)

(52) U.S. Cl.
CPC ............ *G01N 21/9501* (2013.01); *G01N 2021/95615* (2013.01)

(58) Field of Classification Search
CPC .......... G01N 21/9501; G01N 21/88; G01N 21/95607; G01N 21/8803
See application file for complete search history.

(56) References Cited

U.S. PATENT DOCUMENTS

| | | |
|---|---|---|
| 5,640,200 A | 6/1997 | Michael |
| 7,034,272 B1 | 4/2006 | Leonard et al. |
| 7,539,338 B2 | 5/2009 | Fukae et al. |
| 7,559,047 B2 | 7/2009 | Miyamoto et al. |
| 7,847,929 B2 | 12/2010 | Kutscher et al. |
| 8,090,221 B2 | 1/2012 | Chen et al. |
| 8,173,962 B2 | 5/2012 | Sutani et al. |
| 8,331,670 B2 | 12/2012 | Yu et al. |
| 8,467,595 B2 | 6/2013 | Takahashi et al. |
| 2003/0223639 A1 | 12/2003 | Shlain et al. |
| 2006/0288325 A1* | 12/2006 | Miyamoto .......... G03F 7/70625 716/50 |
| 2007/0053582 A1* | 3/2007 | Yamashita .................... 382/151 |

(Continued)

FOREIGN PATENT DOCUMENTS

KR    1020040026157    3/2004

OTHER PUBLICATIONS

U.S. Appl. No. 13/368,306, filed Feb. 7, 2001.

*Primary Examiner* — Gregory J Toatley
*Assistant Examiner* — Kyle R Quigley
(74) *Attorney, Agent, or Firm* — Lowenstein Sandler LLP

(57) ABSTRACT

A system for generating calibration information usable for wafer inspection, the system including: (I) a displacement analysis module, configured to: (a) calculate a displacement for each target out of multiple targets selected in multiple scanned frames which are included in a scanned area of the wafer, the calculating based on a correlation of: (i) an image associated with the respective target which was obtained during a scanning of the wafer, and (ii) design data corresponding to the image; and (b) determining a displacement for each of the multiple scanned frames, the determining based on the displacements calculated for multiple targets in the respective scanned frame; and (II) a subsequent processing module, configured to generate calibration information including the displacements determined for the multiple scanned frames, and a target database that includes target image and location information of each target of a group of database targets.

18 Claims, 25 Drawing Sheets

(56) References Cited

U.S. PATENT DOCUMENTS

| | | |
|---|---|---|
| 2007/0070335 A1* | 3/2007 | Goren ................ G01N 21/8806 |
| | | 356/237.2 |
| 2007/0230770 A1 | 10/2007 | Kulkarni et al. |
| 2008/0181484 A1 | 7/2008 | Litichever et al. |
| 2009/0074299 A1 | 3/2009 | Wenzel |
| 2010/0172570 A1* | 7/2010 | Sakai et al. ................... 382/151 |
| 2012/0057773 A1 | 3/2012 | Langmatz et al. |
| 2012/0207397 A1 | 8/2012 | Nagatomo et al. |

\* cited by examiner

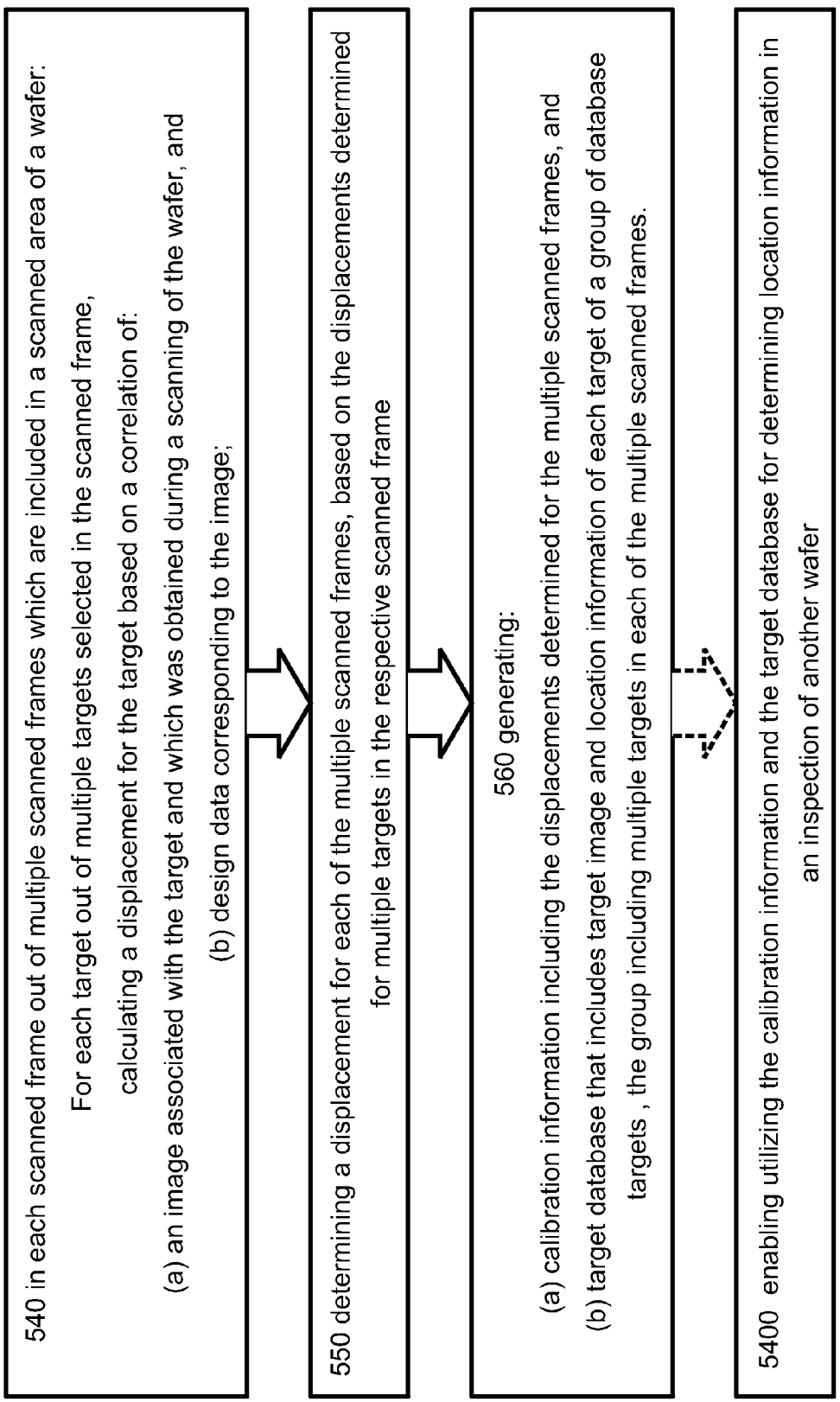

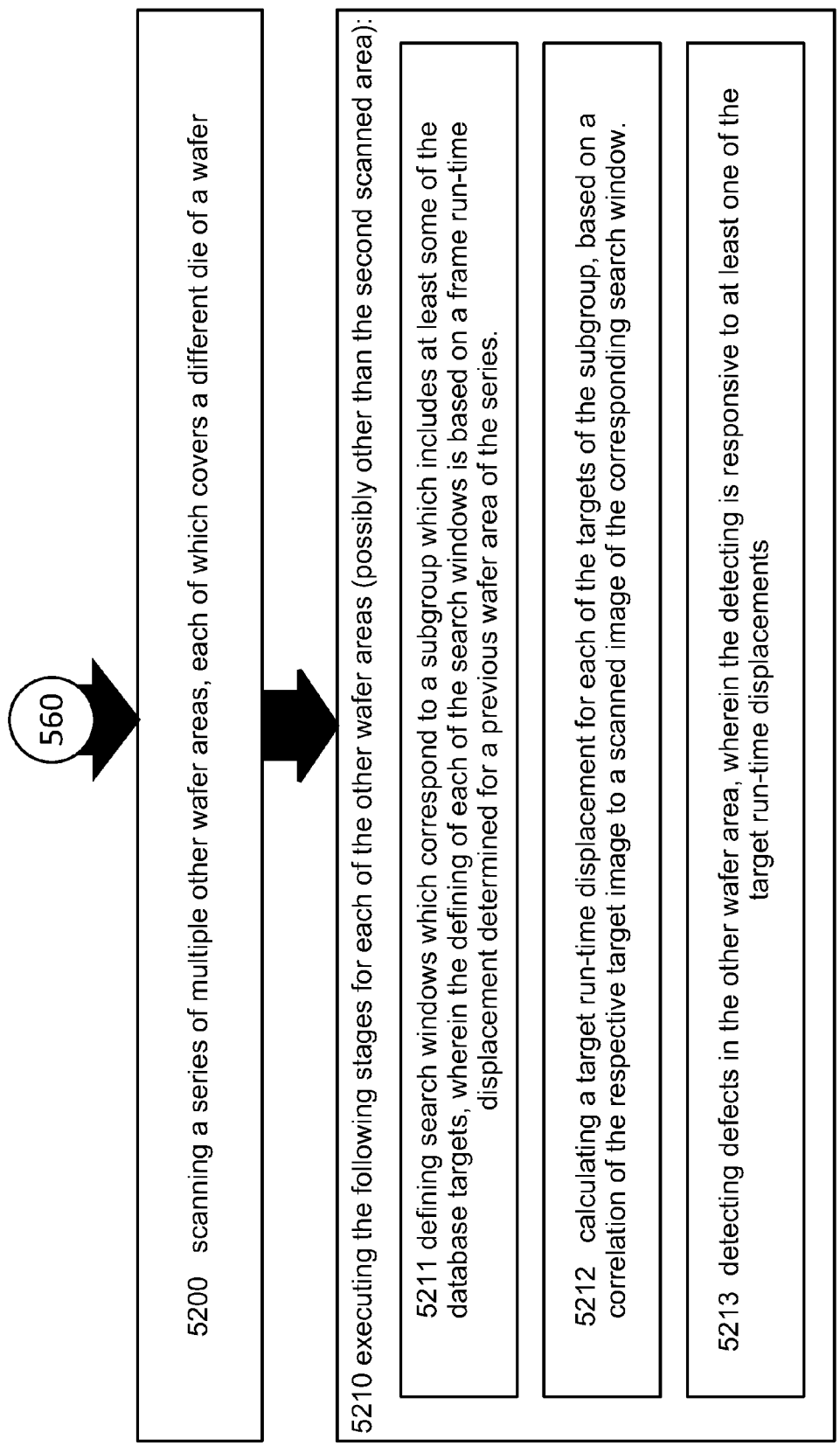

560 generating: (a) calibration information including the displacements determined for the multiple scanned frames, and (b) target database that includes target image and location information of each target of a group of database targets, the group including multiple targets in each of the multiple scanned frames.

563 generating target information of a subgroup that includes multiple targets in an analyzed frame out of the scanned frames, wherein the analyzed frame was scanned in a first scanning direction 570 scanning a second wafer area other than the scanned area 571 scanning the second wafer area which includes a frame that corresponds to the analyzed frame and is scanned in a second scanning direction which is opposite to the first scanning direction 5300 computing an averaged displacement by averaging frame-displacements of scanned frames that are adjacent to the analyzed frame and which were scanned in the second scanning direction 581 defining search windows which correspond to the targets of the subgroup, wherein the defining of each of the search windows is based on the averaged displacement 590 correlating each of multiple target images to at least a portion of a scanned image of the corresponding search window 5100 calculating a run-time displacement for each out of multiple database targets, based on a correlation of the respective target image to at least a portion of a scanned image of the corresponding search window 5140 detecting defects in the second wafer area, wherein the detecting is provided with the help of at least one of the target run-time displacements

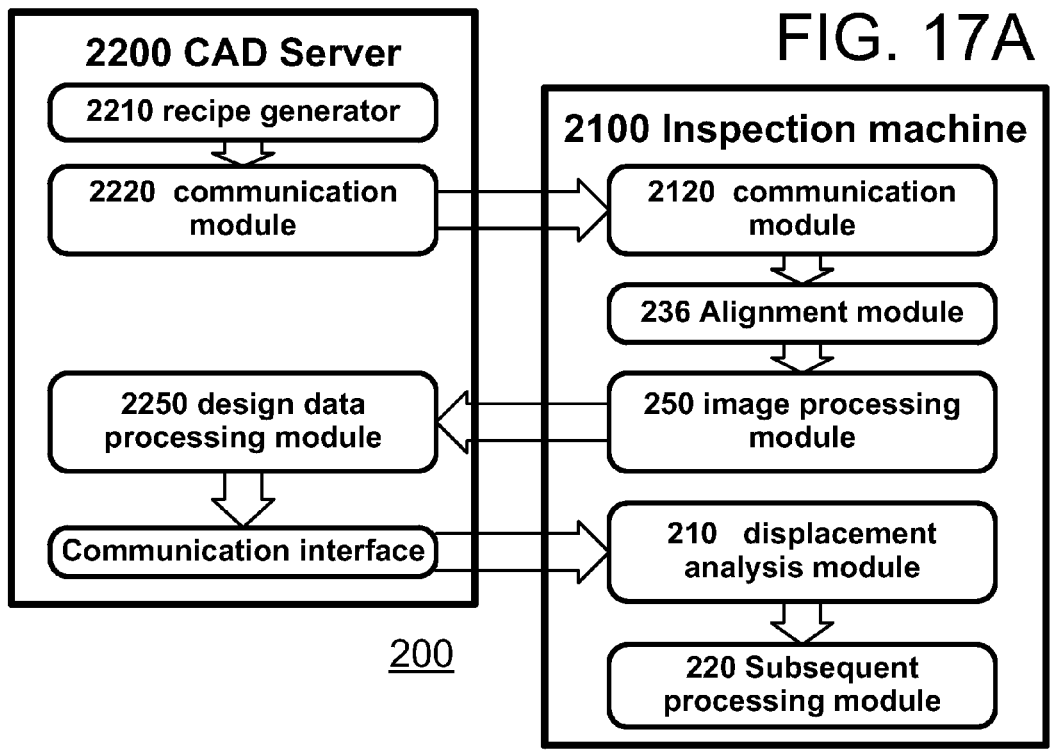
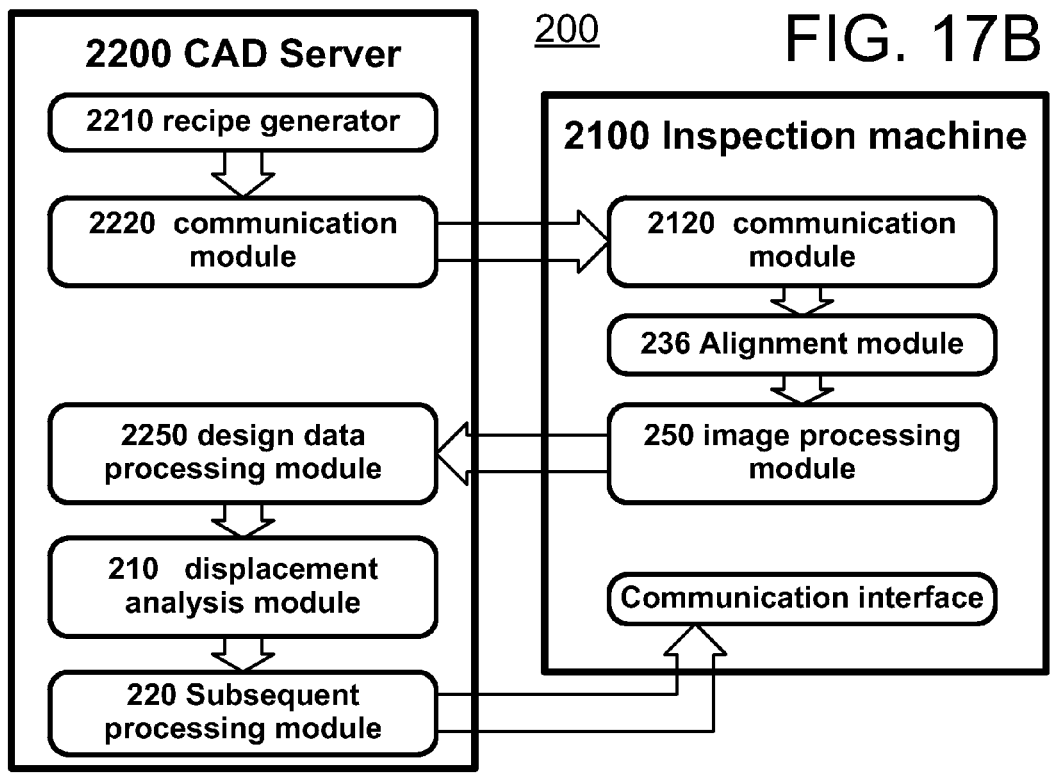

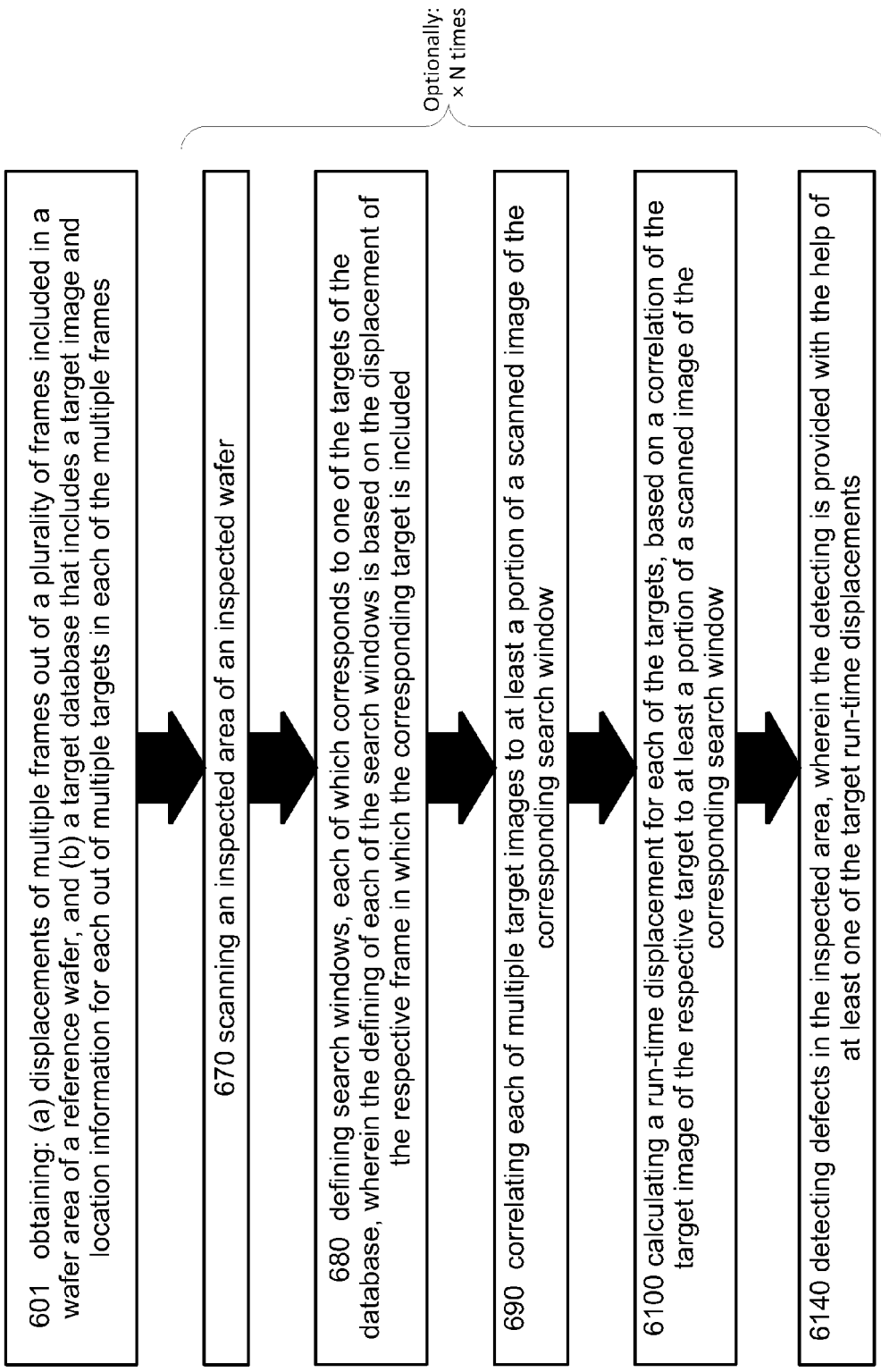

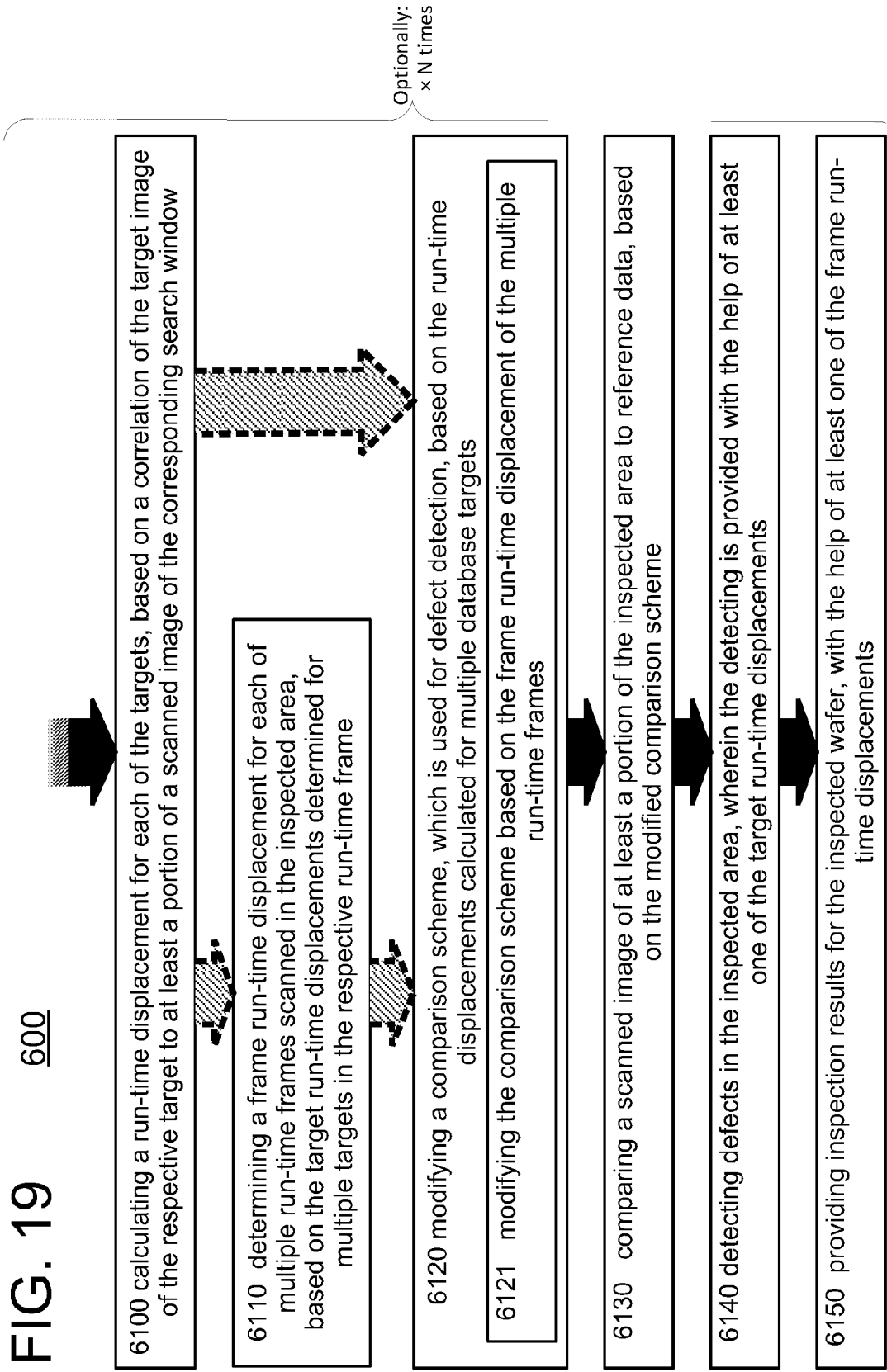

6200 scanning a series of multiple inspected areas, each of which covers a different die of a wafer 6210 executing the following stages for each of the inspected areas of the series, possibly other than first:

6211 defining search windows which correspond to a subgroup which includes at least some of the database targets, wherein the defining of each of the search windows is based on a frame run-time displacement determined for a previous inspected wafer area of the series.

5212 calculating a target run-time displacement for each of the targets of the subgroup, based on a correlation of the respective target image to a scanned image of the corresponding search window.

5213 detecting defects in the other wafer area, wherein the detecting is responsive to at least one of the target run-time displacements

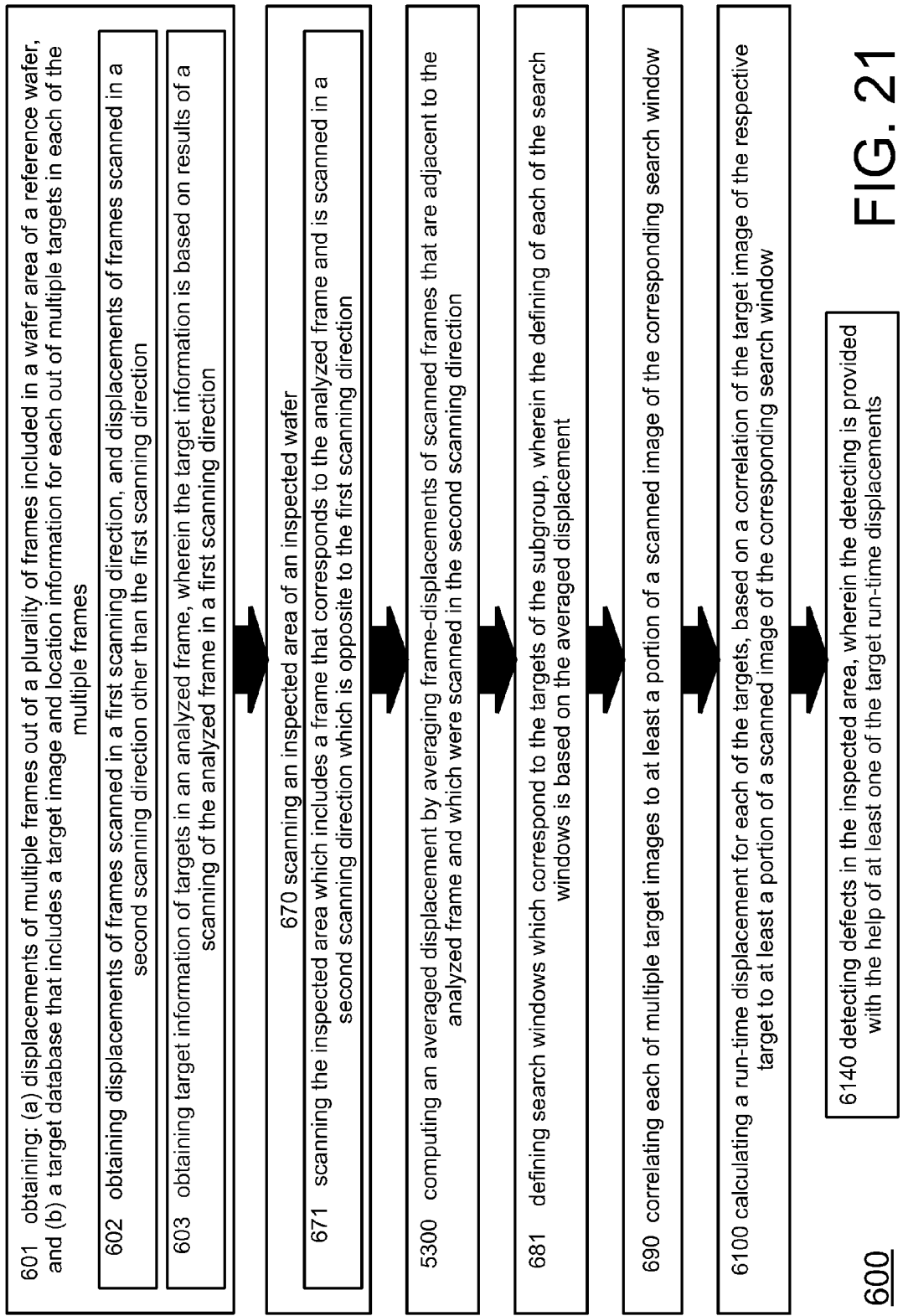

SYSTEM, A METHOD AND A COMPUTER PROGRAM PRODUCT FOR CAD-BASED REGISTRATION

FIELD OF THE INVENTION

This invention relates to systems, methods and computer program products for CAD-based registration.

BACKGROUND OF THE INVENTION

FIG. 1 is an illustration of a wafer 10 such as ones which may be used in the fabrication of integrated circuits and other microdevices. While the term wafer may be used to refer only to the substrate material on which the integrated circuit is fabricated (e.g. a thin slice of semiconductor material, such as a silicon crystal), this term may also be used to refer to the entire construction, including the electronic circuit fabricated on the wafer. The wafer 10 is divided into multiple dies 11 which are illustrated in a widely implemented rectangular form. Like the term 'wafer', the term 'die' may also be used either for small blocks of semiconducting material, on which a given functional circuit is fabricated, or for such a block including the fabricated electric circuit.

Usually, wafer 10 may be cut ("diced") into its multiple dies 11, wherein all of the dies of the wafer contain a copy of the same electronic circuit. While not necessarily so, each of the dies 11 is independently functional.

U.S. Pat. No. 7,847,929 which is entitled "Methods and Apparatus for Inspecting a Plurality of Dies" discloses a method for inspecting a plurality of dies, that are typically disposed on a surface of a semiconducting wafer. Each of the dies includes respective functional features within the die. The method consists of identifying within a first die a first multiplicity of the functional features having respective characteristics, and measuring respective first locations of the first multiplicity with respect to an origin of the first die. Within a group of second dies a second multiplicity of the functional features having the respective characteristics is identified, respective second locations of the second multiplicity are measured. The second locations are compared to the first locations to determine a location of an origin of the group of the second dies.

SUMMARY OF THE INVENTION

In accordance with an aspect of the presently disclosed subject matter, there is provided a system for generating calibration information usable for wafer inspection, the system including a displacement analysis module, configured to: (a) calculate a displacement for each target out of multiple targets selected in multiple scanned frames which are included in a scanned area of the wafer, the calculating based on a correlation of: (i) an image associated with the respective target which was obtained during a scanning of the wafer, and (ii) design data corresponding to the image; and (b) determining a displacement for each of the multiple scanned frames, the determining based on the displacements calculated for multiple targets in the respective scanned frame; and a subsequent processing module, configured to generate: (a) calibration information including the displacements determined for the multiple scanned frames, and (b) a target database that includes target image and location information of each target of a group of database targets, the group including multiple targets in each of the multiple scanned frames.

In accordance with an embodiment of the presently disclosed subject matter, there is provided a system, wherein the subsequent processing module is configured to save the location information of the database targets in computer aided design (CAD) coordinates.

In accordance with an embodiment of the presently disclosed subject matter, there is further provided a system, further including an input interface for receiving scanned image data of the scanned area of the wafer; and an image processing module, configured to select the image for each of the multiple targets based on image processing of the scanned image data; and to save the multiple images based on the selection.

In accordance with an embodiment of the presently disclosed subject matter, there is yet further provided a system, wherein the image processing module is further configured to define the scanned frames based on image processing of the scanned image data.

In accordance with an embodiment of the presently disclosed subject matter, there is yet further provided a system, wherein the subsequent processing module is configured to determine the displacement for at least one of the scanned frames by determining for the scanned frame an X-axis displacement value for the frame based on the displacements determined for targets of a first subgroup of the targets of the frame, and determining a Y-axis displacement value for the frame based on the displacements determined for the targets of a second subgroup of other targets of the scanned frame, wherein the determining of the Y-axis displacement value is irrespective of the displacements determined for the targets of the first subgroup.

In accordance with an embodiment of the presently disclosed subject matter, there is yet further provided a system, further including an input interface for receiving scanned image data of a second wafer area other than the scanned area; a correlator, configured to: (a) define search windows, each of which corresponds to one of the database targets, wherein the defining of each of the search windows is based on the determined displacement of the respective scanned-frame in which the corresponding target is included; and (b) calculate a run-time displacement for multiple database targets, based on a correlation of the respective target image to at least a portion of a scanned image of the corresponding search window; and a defect detection module, configured to detect defects in the second wafer area with the help of at least one of the target run-time displacements.

In accordance with an embodiment of the presently disclosed subject matter, there is yet further provided a system, further including an output interface configured to report at least some of the defects, wherein the reporting includes reporting location information of at least one of the defects in coordinates of the design data.

In accordance with an embodiment of the presently disclosed subject matter, there is yet further provided a system, wherein the correlator is configured to determine a frame run-time displacement for each of multiple run-time frames scanned in the second wafer area, based on the target run-time displacements determined for multiple targets in the respective run-time frame; wherein the defect detection module is further configured to modify a comparison scheme based on the frame run-time displacement of the multiple run-time frames; wherein the defect detection module is configured to compare a scanned image of at least a portion of the second wafer area to reference data, based on the modified comparison scheme and to detect defects in the second wafer area based on results of the comparing.

In accordance with an embodiment of the presently disclosed subject matter, there is yet further provided a system, wherein the input interface is configured to receive scanned image data of a series of multiple other wafer areas other than the scanned area, the series including the second wafer area, wherein each of the other wafer areas covers a different die; wherein the correlator is configured to perform the following actions for each of the other wafer areas, other than the second scanned area: (a) define search windows which correspond to a subgroup which includes at least some of the database targets, wherein the defining of each of the search windows is based on a frame run-time displacement determined for a previous wafer area of the series, wherein the size of at least one of the search windows is smaller than the size of a search window defined for the corresponding target in the second wafer area; and (b) calculate a target run-time displacement for each of the targets of the subgroup, based on a correlation of the respective target image to a scanned image of the corresponding search window; wherein the defect sensor is configured to detect defects in the other wafer area in response to at least one of the target run-time displacements.

In accordance with an embodiment of the presently disclosed subject matter, there is yet further provided a system, further including an input interface for receiving scanning results of a scan of the scanned area of the wafer that was scanned in slices scanned in alternating scanning directions; wherein the subsequent processing module is configured to generate, as part of the calibration information, a first displacement map which includes frame-displacements of scanned frames scanned in a first scanning direction, and a second displacement map which includes frame-displacements of scanned frames scanned in a second scanning direction.

In accordance with an embodiment of the presently disclosed subject matter, there is yet further provided a system, wherein the subsequent processing module is configured to generate, as part of the target database, target information of a subgroup that includes multiple targets in an analyzed frame out of the scanned frames, wherein the analyzed frame was scanned in a first scanning direction; wherein the target information of each of the targets of the subgroup includes the target image associated with the target and location information; wherein the input interface is configured to receive scanned image data of a second wafer area other than the scanned area, wherein the second wafer area includes a frame that corresponds to the analyzed frame and is scanned in a second scanning direction which is opposite to the first scanning direction; wherein the correlator is configured to: (a) compute an averaged displacement by averaging frame-displacements of scanned frames that are adjacent to the analyzed frame and which were scanned in the second scanning direction; (b) define search windows which correspond to the targets of the subgroup, wherein the defining of each of the search windows is based on the averaged displacement; and (c) calculate a target run-time displacement for each of the targets of the subgroup, based on a correlation of the respective target image to a scanned image of the corresponding search window; wherein the defect sensor is configured to detect defects in the second wafer area in response to at least one of the target run-time displacements.

In accordance with an aspect of the presently disclosed subject matter, there is yet further provided a computerized method for generating calibration information usable for wafer inspection, the method including: determining a displacement for each of the multiple scanned frames, the determining based on the displacements calculated for multiple targets in the respective scanned frame; and generating (a) calibration information including the displacements determined for the multiple scanned frames, and (b) a target database that includes target image and location information of each target of a group of database targets, the group including multiple targets in each of the multiple scanned frames.

In accordance with an embodiment of the presently disclosed subject matter, there is yet further provided a method, the method including enabling utilizing the calibration information and the target database for determining location information in an inspection of another wafer.

In accordance with an embodiment of the presently disclosed subject matter, there is yet further provided a method, wherein the generating includes saving the location information of the database targets in computer aided design (CAD) coordinates.

In accordance with an embodiment of the presently disclosed subject matter, there is yet further provided a method, further including: scanning the scanned area of the wafer to provide scanned image data; selecting the image for each of the multiple targets based on image processing of the scanned image data; and saving the multiple images based on the selection.

In accordance with an embodiment of the presently disclosed subject matter, there is yet further provided a method 5, further including defining the scanned frames based on image processing of the scanned image data.

In accordance with an embodiment of the presently disclosed subject matter, there is yet further provided a method, wherein the determining of the displacement for at least one of the scanned frames includes determining for the scanned frame an X-axis displacement value for the frame based on the displacements determined for targets of a first subgroup of the targets of the frame, and determining a Y-axis displacement value for the frame based on the displacements determined for the targets of a second subgroup of other targets of the scanned frame, wherein the determining of the Y-axis displacement value is irrespective of the displacements determined for the targets of the first subgroup.

In accordance with an embodiment of the presently disclosed subject matter, there is yet further provided a method, wherein the generating is followed by: scanning of a second wafer area other than the scanned area; for each out of multiple targets of the database: defining a corresponding search window based on the determined displacement of the scanned-frame in which the target is included; and calculating a run-time displacement for the target, based on a correlation of the target image to at least a portion of an area of the scanned image which is defined by the corresponding search window; determining a frame run-time displacement for each of multiple run-time frames scanned in the second wafer area, based on the target run-time displacements determined for multiple targets in the respective run-time frame; and providing inspection results for a wafer which includes the second wafer area, with the help of at least one of the frame run-time displacements.

In accordance with an embodiment of the presently disclosed subject matter, there is yet further provided a method, further including detecting defects in the second wafer area with the help of at least one of the target run-time displacements, wherein the providing includes providing results of the defect detection.

In accordance with an embodiment of the presently disclosed subject matter, there is yet further provided a method, further including reporting defects, after the detecting, wherein the reporting includes reporting location information of at least one of the defects in coordinates of the design data.

In accordance with an embodiment of the presently disclosed subject matter, there is yet further provided a method, further including: modifying a comparison scheme based on the frame run-time displacement of the multiple run-time frames; and comparing a scanned image of at least a portion of the second wafer area to reference data, based on the modified comparison scheme; wherein the detecting of the defects is based on results of the comparing.

In accordance with an embodiment of the presently disclosed subject matter, there is yet further provided a method, including: scanning a series of multiple other wafer areas other than the scanned area, the series including the second wafer area, wherein each of the other wafer areas covers a different die; and for each of the other wafer areas, other than the second scanned area: defining search windows which correspond to a subgroup which includes at least some of the database targets, wherein the defining of each of the search windows is based on a frame run-time displacement determined for a previous wafer area of the series, wherein the size of at least one of the search windows is smaller than the size of a search window defined for the corresponding target in the second wafer area; calculating a target run-time displacement for each of the targets of the subgroup, based on a correlation of the respective target image to a scanned image of the corresponding search window; and detecting defects in the other wafer area, wherein the detecting is responsive to at least one of the target run-time displacements.

In accordance with an embodiment of the presently disclosed subject matter, there is yet further provided a method, wherein the calculating is preceded by scanning the scanned area of the wafer in slices which are scanned in alternating scanning directions; wherein the generating of the calibration information includes generating a first displacement map which includes frame-displacements of scanned frames scanned in a first scanning direction, and a second displacement map which includes frame-displacements of scanned frames scanned in a second scanning direction.

In accordance with an embodiment of the presently disclosed subject matter, there is yet further provided a method, wherein the generating of the target database includes generating target information of a subgroup that includes multiple targets in an analyzed frame out of the scanned frames, wherein the analyzed frame was scanned in a first scanning direction; wherein the target information of each of the targets of the subgroup includes the target image associated with the target and location information; wherein the generating is followed by: scanning of a second wafer area other than the scanned area, wherein the second wafer area includes a frame that corresponds to the analyzed frame and is scanned in a second scanning direction which is opposite to the first scanning direction; computing an averaged displacement by averaging frame-displacements of scanned frames that are adjacent to the analyzed frame and which were scanned in the second scanning direction; defining search windows which correspond to the targets of the subgroup, wherein the defining of each of the search windows is based on the averaged displacement; calculating a target run-time displacement for each of the targets of the subgroup, based on a correlation of the respective target image to a scanned image of the corresponding search window; and detecting defects in the second wafer area, wherein the detecting is responsive to at least one of the target run-time displacements.

In accordance with an aspect of the presently disclosed subject matter, there is yet further provided a program storage device readable by machine, tangibly embodying a program of instructions executable by the machine to perform a method for generating calibration information usable for wafer inspection, including the steps of: (a) determining a displacement for each of the multiple scanned frames, the determining based on the displacements calculated for multiple targets in the respective scanned frame; and (b) generating (i) calibration information including the displacements determined for the multiple scanned frames, and (ii) a target database that includes target image and location information of each target of a group of database targets, the group including multiple targets in each of the multiple scanned frames.

In accordance with an embodiment of the presently disclosed subject matter, there is yet further provided a program storage device, wherein the program of instructions further includes computer readable program code for causing the machine to enable utilizing the calibration information and the target database for determining location information in an inspection of another wafer.

In accordance with an embodiment of the presently disclosed subject matter, there is yet further provided a program storage device, wherein the computer readable program code that is included in the program of instructions for causing the machine to perform the step of generating include instructions for saving the location information of the database targets in computer aided design (CAD) coordinates.

In accordance with an embodiment of the presently disclosed subject matter, there is yet further provided a program storage device, wherein the program of instructions further includes computer readable program code for causing the machine to: (a) scan the scanned area of the wafer to provide scanned image data; (b) select the image for each of the multiple targets based on image processing of the scanned image data; and (c) save the multiple images based on the selection.

In accordance with an embodiment of the presently disclosed subject matter, there is yet further provided a program storage device, wherein the program of instructions further includes computer readable program code for causing the machine to define the scanned frames based on image processing of the scanned image data.

In accordance with an embodiment of the presently disclosed subject matter, there is yet further provided a program storage device, wherein the computer readable program code that is included in the program of instructions for causing the machine to perform the determining of the displacement for at least one of the scanned frames includes instructions for determining for the scanned frame an X-axis displacement value for the frame based on the displacements determined for targets of a first subgroup of the targets of the frame, and determining a Y-axis displacement value for the frame based on the displacements determined for the targets of a second subgroup of other targets of the scanned frame, wherein the determining of the Y-axis displacement value is irrespective of the displacements determined for the targets of the first subgroup.

In accordance with an embodiment of the presently disclosed subject matter, there is yet further provided a program storage device, wherein the program of instructions further includes computer readable program code for causing the machine to perform the following steps after the execution of the step of generating: (a) scanning of a second wafer area other than the scanned area; (b) for each out of multiple targets of the database: (i) defining a corresponding search window based on the determined displacement of the scanned-frame in which the target is included; and (ii) calculating a run-time displacement for the target, based on a correlation of the target image to at least a portion of an area of the scanned image which is defined by the corresponding search window; (c) determining a frame run-time displacement for each of multiple run-time frames scanned in the second wafer area, based on the target run-time displacements determined for multiple targets in the respective run-time frame; and (d) providing inspection results for a wafer which includes the second wafer area, with the help of at least one of the frame run-time displacements.

In accordance with an embodiment of the presently disclosed subject matter, there is yet further provided a program storage device, wherein the program of instructions further includes computer readable program code for causing the machine to detect defects in the second wafer area with the help of at least one of the target run-time displacements, wherein the providing includes providing results of the defect detection.

In accordance with an embodiment of the presently disclosed subject matter, there is yet further provided a program storage device, wherein the program of instructions further includes computer readable program code for causing the machine to report defects, after the detecting, wherein the reporting includes reporting location information of at least one of the defects in coordinates of the design data.

In accordance with an embodiment of the presently disclosed subject matter, there is yet further provided a program storage device, wherein the program of instructions further includes computer readable program code for causing the machine to: (a) modify a comparison scheme based on the frame run-time displacement of the multiple run-time frames; and (b) compare a scanned image of at least a portion of the second wafer area to reference data, based on the modified comparison scheme; wherein the detecting of the defects is based on results of the comparing.

In accordance with an embodiment of the presently disclosed subject matter, there is yet further provided a program storage device, wherein the program of instructions further includes computer readable program code for causing the machine to: scan a series of multiple other wafer areas other than the scanned area, the series including the second wafer area, wherein each of the other wafer areas covers a different die; and for each of the other wafer areas, other than the second scanned area: (a) define search windows which correspond to a subgroup which includes at least some of the database targets, wherein the defining of each of the search windows is based on a frame run-time displacement determined for a previous wafer area of the series, wherein the size of at least one of the search windows is smaller than the size of a search window defined for the corresponding target in the second wafer area; (b) calculate a target run-time displacement for each of the targets of the subgroup, based on a correlation of the respective target image to a scanned image of the corresponding search window; and (c) detect defects in the other wafer area, wherein the detecting is responsive to at least one of the target run-time displacements.

In accordance with an embodiment of the presently disclosed subject matter, there is yet further provided a program storage device, wherein the program of instructions further includes computer readable program code for causing the machine to scan, prior to executing the step of calculating, the scanned area of the wafer in slices which are scanned in alternating scanning directions; wherein the generating of the calibration information includes generating a first displacement map which includes frame-displacements of scanned frames scanned in a first scanning direction, and a second displacement map which includes frame-displacements of scanned frames scanned in a second scanning direction.

In accordance with an embodiment of the presently disclosed subject matter, there is yet further provided a program storage device, wherein the computer readable program code that is included in the program of instructions for causing the machine to perform the step of generating the target database further includes instructions for generating target information of a subgroup that includes multiple targets in an analyzed frame out of the scanned frames, wherein the analyzed frame was scanned in a first scanning direction; wherein the target information of each of the targets of the subgroup includes the target image associated with the target and location information; and, following generating: (a) scanning of a second wafer area other than the scanned area, wherein the second wafer area includes a frame that corresponds to the analyzed frame and is scanned in a second scanning direction which is opposite to the first scanning direction; (b) computing an averaged displacement by averaging frame-displacements of scanned frames that are adjacent to the analyzed frame and which were scanned in the second scanning direction; (c) defining search windows which correspond to the targets of the subgroup, wherein the defining of each of the search windows is based on the averaged displacement; (d) calculating a target run-time displacement for each of the targets of the subgroup, based on a correlation of the respective target image to a scanned image of the corresponding search window; and (e) detecting defects in the second wafer area, wherein the detecting is responsive to at least one of the target run-time displacements.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 3-8 illustrate a computerized method for generating calibration information usable for wafer inspection, according to various embodiments of the invention;

FIGS. 17A and 17B illustrate relationships between an inspection machine and a CAD server, according to various embodiments of the invention;

FIGS. 18-21 illustrate a computerized method location based wafer analysis of at least one wafer, according to various embodiments of the invention.

Figure 1:
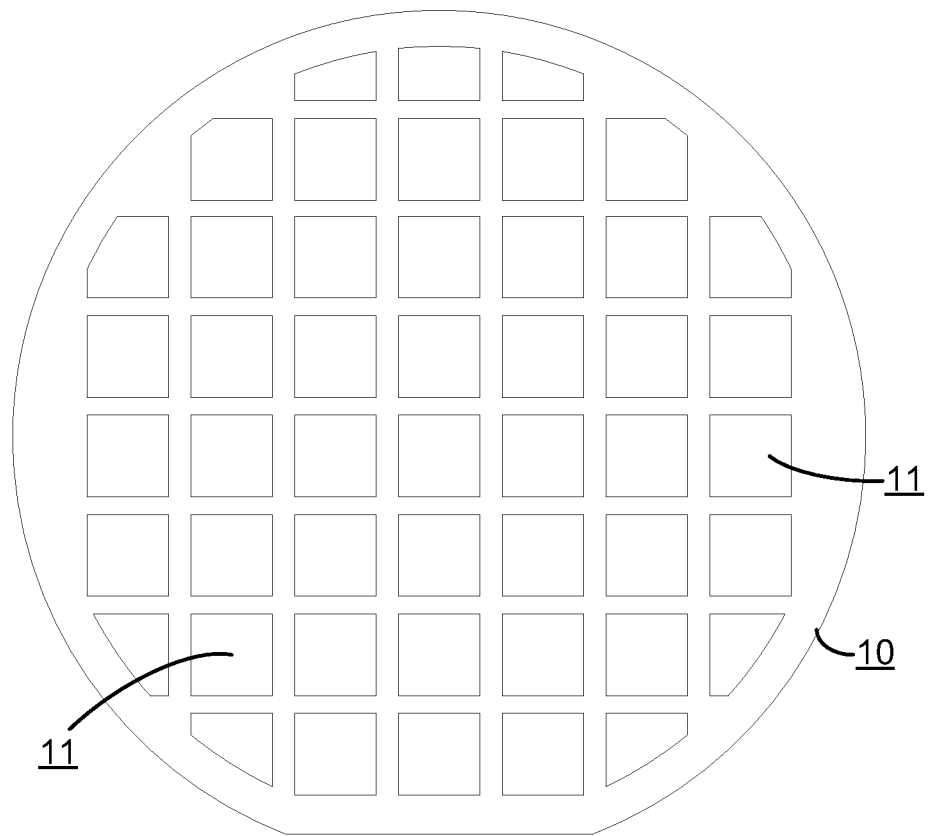
FIG. 1 is an illustration of a wafer 10 such as ones which may be used in the fabrication of integrated circuits and other microdevices.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "processing", "calculating", "determining", "generating", "computing", "selecting", or the like, include action and/or processes of a computer that manipulate and/or transform data into other data, said data represented as physical quantities, e.g. such as electronic quantities, and/or said data representing the physical objects. The term "computer" should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof.

The operations in accordance with the teachings herein may be performed by a computer specially constructed for the desired purposes or by a general purpose computer specially configured for the desired purpose by a computer program stored in a computer readable storage medium.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

In embodiments of the presently disclosed subject matter one or more stages illustrated in the figures may be executed in a different order and/or one or more groups of stages may be executed simultaneously and vice versa. The figures illustrate a general schematic of the system architecture in accordance with an embodiment of the presently disclosed subject matter. Each module in the figures can be made up of any combination of software, hardware and/or firmware that performs the functions as defined and explained herein. The modules in the figures may be centralized in one location or dispersed over more than one location.

Figure 2A:
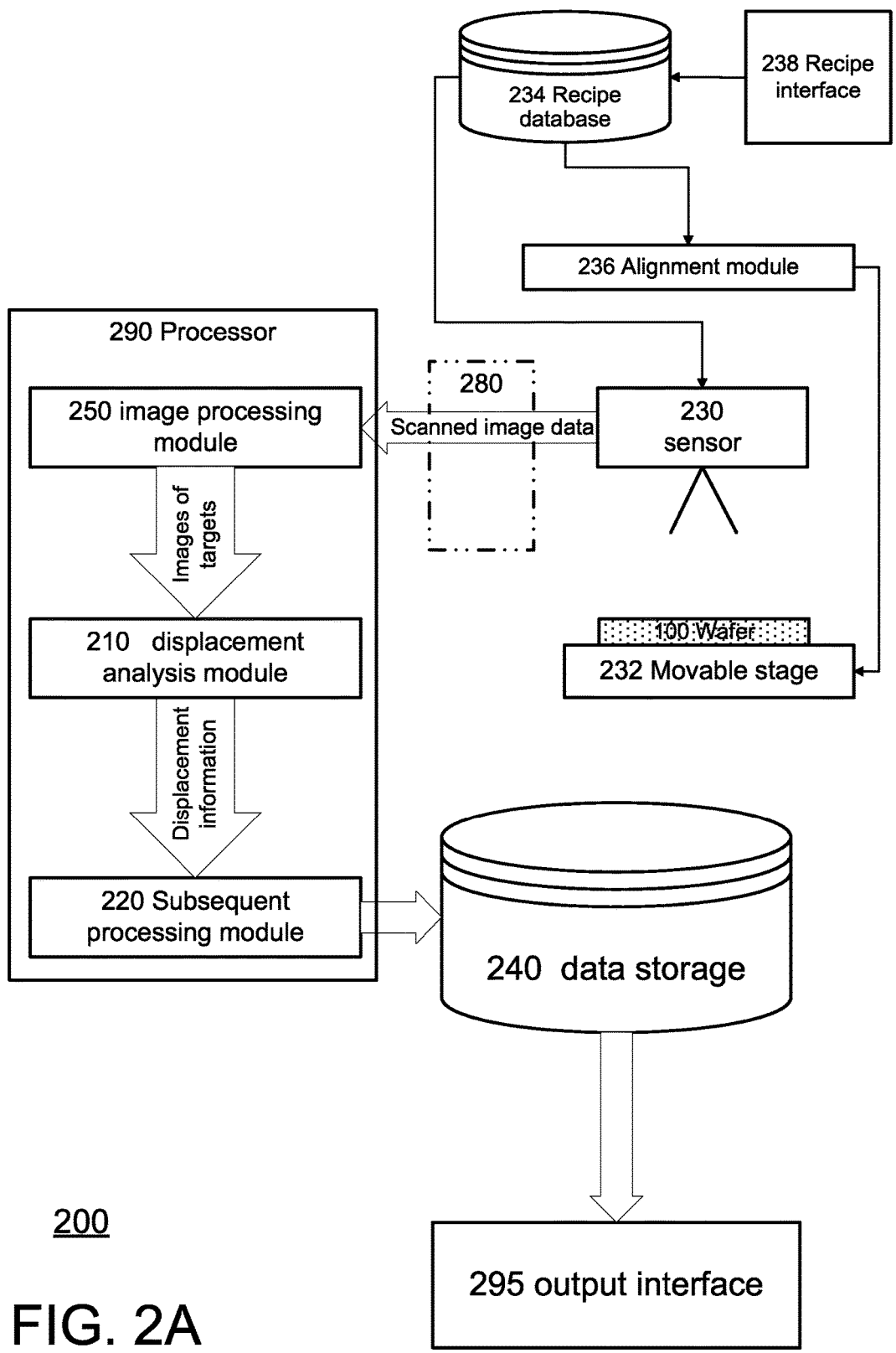
FIGS. 2A and 2B illustrate a system for generating calibration information usable for wafer inspection of a wafer, according to an embodiment of the invention.

FIG. 2 illustrates system 200 for generating calibration information usable for wafer inspection of a wafer, according to an embodiment of the invention. System 200 may be combined with an inspection machine that is used to inspect the wafer (e.g. during different stages of manufacturing thereof) or connected to such a machine, but this is not necessarily so. Also, system 200 may be an inspection machine into which some or all of the modifications and/or features discussed below have been integrated.

As will be discussed below in more detail, one or more of the components of system 200 may be used to generate calibration information that includes displacements determined for different parts of the wafer. Those displacements determined may later be used in manufacturing of the wafer, and/or in later stages of inspection of the wafer. Some of the ways in which system 200 may operate will become clearer when viewed in light of method 500 discussed below. Therefore, part of the description of system 200 will be provided after method 500 is discussed, and the description of system 200 preceding the discussion of method 500 is therefore partial.

It should be noted that, as will be clear to any person who is of skill in the art, wherever the term "wafer" is used—similar techniques, systems, methods and computer program products may be implemented for optical masks that are used for the manufacturing of wafers.

Without limiting the scope of the invention in any way, in some possible implementations system 200 may be used for inspection tools in which an entire wafer or at least an entire die is scanned for detection of potential defects (such as the Elite and the UVision systems by Applied Materials, Inc.), and/or for review tools which are typically of higher resolution (e.g. a scanning electron microscope, SEM) which are used for ascertaining whether a potential defect is indeed a defect. Such review tools usually inspect fragments of a die, one at a time, in high resolution. Whenever the term "inspection" or its derivatives are used in this disclosure, such an inspection is not limited with respect to resolution or size of inspection area, and may be applied, by way of example, to review tools and to lower resolution wafer inspection tools alike.

System 200 includes at least displacement analysis module 210 which determines displacements in the scanning of different parts of a wafer 100, and subsequent processing module 220 which generates calibration information as well as additional information. As is demonstrated in some embodiments of the invention discussed below, the information generated by the subsequent processing module may be used to improve later scanning of the wafer, or of similar wafers.

Each of displacement analysis module 210 and subsequent processing module 220 (and possibly also image processing module 250, correlator 260 and defect detection module 270) may be implemented by one or more hardware processors, either independent from those of the other modules, or shared with at least one of them. Those modules may also include software processing modules and/or firmware processing modules. For example, some or all of those modules may be implemented on a hardware processor 290.

The scanning of the wafer 100 may be implemented by any scanning, imaging and/or detecting apparatus, many of which are known in the art. Such an apparatus (denoted "sensor 230") may be part of system 200, but this is not necessarily so and the two may or may not be directly connected. By way of example, such an apparatus may be a scanning electron microscope, an optical inspection system and so forth. Wafer 100 may be similar to prior art wafer 10 discussed in the Background.

By way of example, a wafer 100 (or several wafers) may be placed on a movable stage 232. In such an implementation, wafer 100 remains stationary with respect to movable stage 232 during the scanning of wafer 100, and the respective movement between wafer 100 and sensor 230 (if required to image different parts of the wafer) is achieved by controllably moving movable stage 232. For example, movable stage 232 may be moved along an X-axis, a Y-axis, and possibly also a Z-axis direction (wherein the X and Y axes are perpendicular axes on the surface plane of movable stage 232, and the Z-axis is perpendicular to both of those axes). Alternatively (or in addition), sensor 230 may change a position in order to image different parts of wafer 100.

Figure 9:
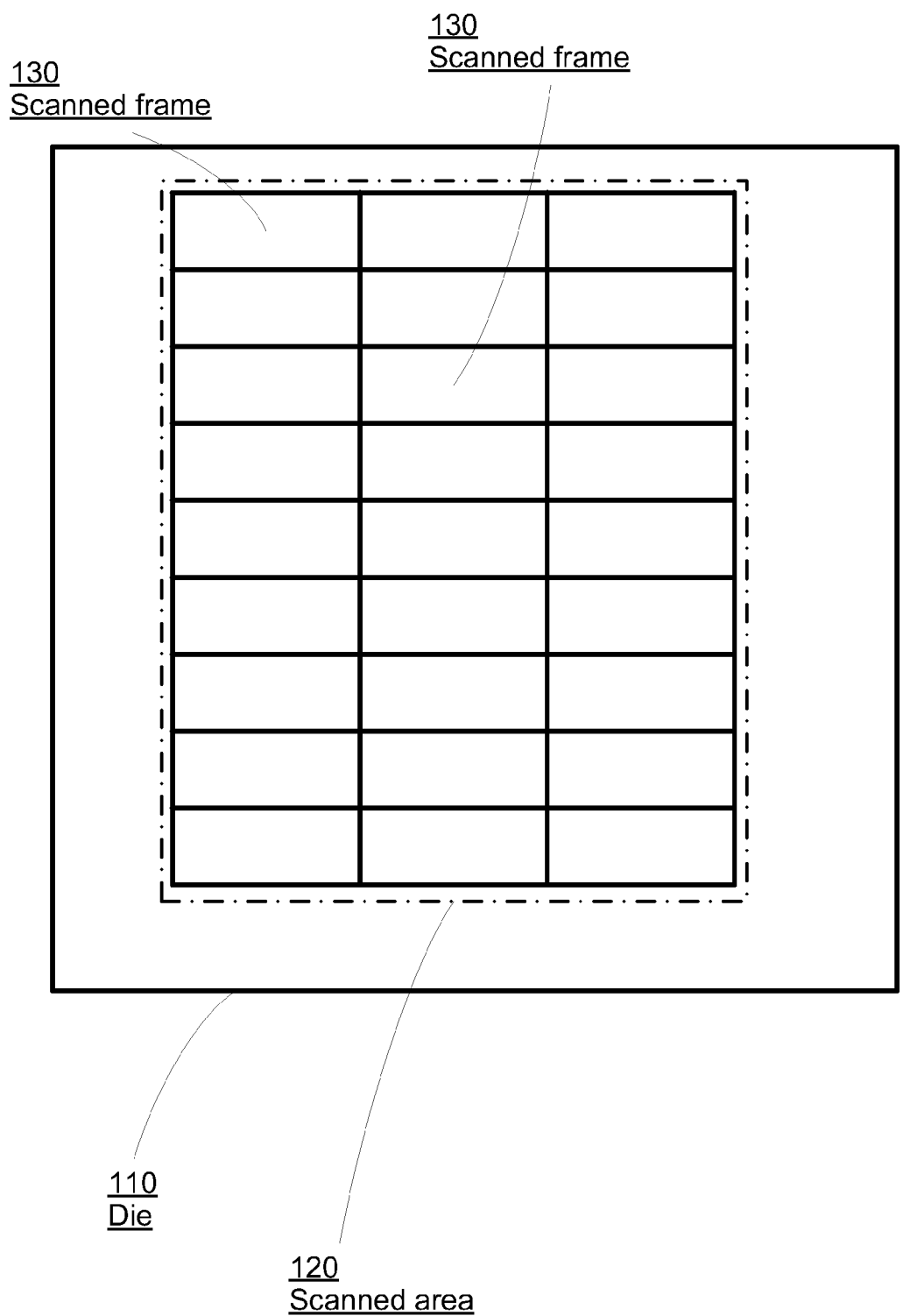
FIG. 9 illustrates relationships between a scanned area, a scanned frame, and a die of a wafer, according to an embodiment of the invention.

Displacement analysis module 210 receives information gathered in a scanning of an area 120 of wafer 100 (an example of such a scanned area 120 is provided in FIG. 9). It should be noted that while scanned area 120 is illustrated as a single continuous rectangular area, in other implementations the geometry and/or topology of the scanned area may vary. The scanning of the scanned area may be executed by sensor 230, and may be based on scanning instructions retrieved from a scanning recipe (which may be stored in recipe database 234).

The scanned area 120 is divided into multiple sub-areas, herein referred to as "scanned frames 130". The dividing of the scanned area 120 into frames may be executed by the sensor 230 which scans the area 130, by displacement analysis module 210 which processes the scanning data, or by another unit. While the frames 130 may be of identical shape and size, this is not necessarily so. As discussed below in greater detail, in some implementations dividing the scanned area 120 into frames 130 of varying sizes may be beneficial. Likewise, while the frames 130 are illustrated as non-overlapping and as covering the entire scanned area 120, this is not necessarily so. In some implementations one or more parts of scanned area 120 may be covered by more than one frame 130, or by none at all. As will be demonstrated below, a displacement is determined by displacement analysis module 210 for each of those independent frames.

Figure 10A:
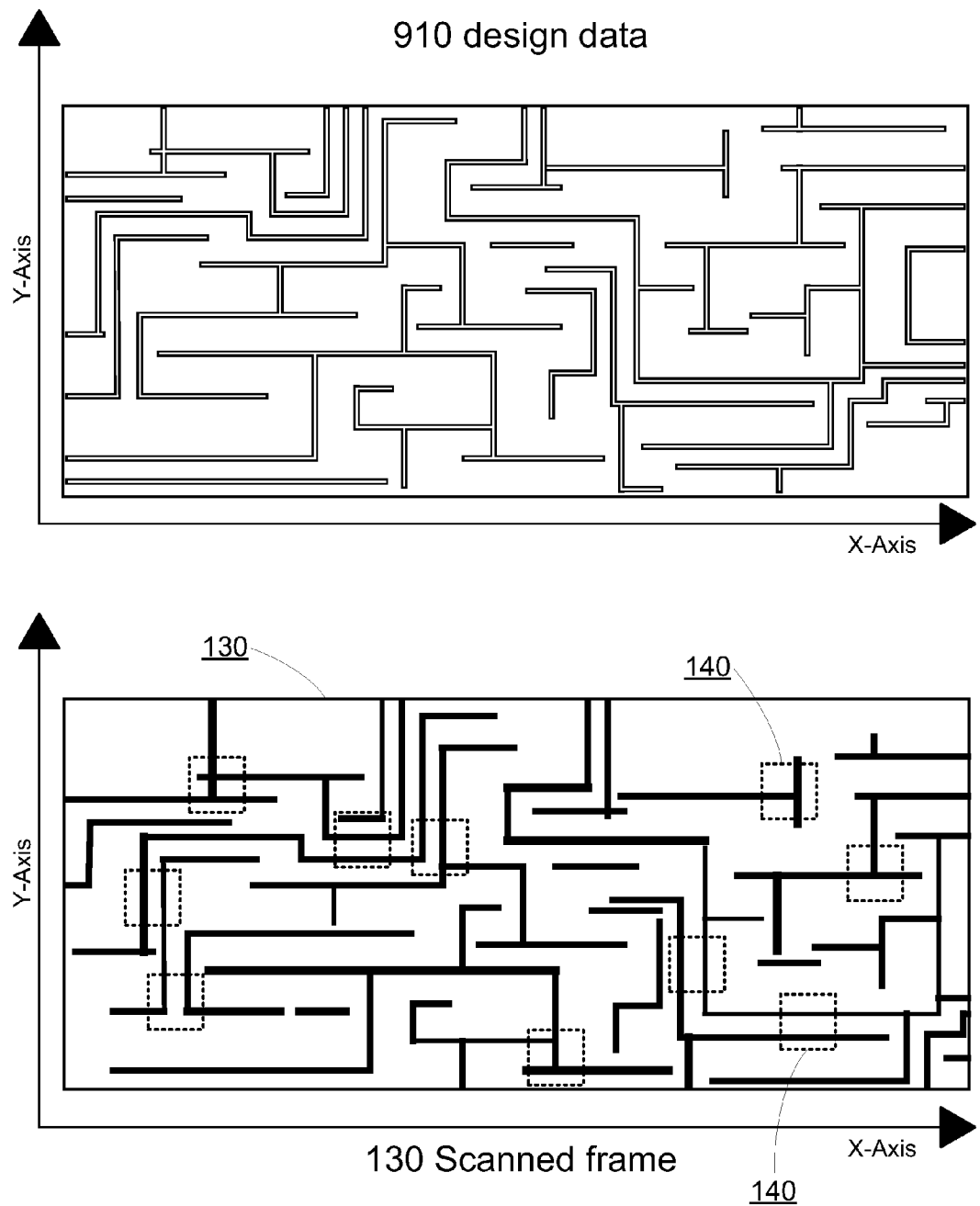
FIGS. 10A-10D illustrate relationships between various entities which may be utilized in various implementations of the invention, with respect to scanned image data and to design data, according to various embodiments of the invention.

Multiple targets 140 are defined within each of the frames 130 (e.g. as exemplified in FIG. 10A). Some of the ways in which such targets may be determined are discussed below. For example, each of the targets may be selected to include a pattern which is identifiable within its environment (e.g. by means of image processing). Each of the targets 140 has image data associated with it, as well as associated location information. The associated location information may be an assessed location, whose assessment may be facilitated by an alignment of the wafer with respect to sensor 230 (and/or to stage 232) prior to the scanning of area 120. Such an alignment may be executed and/or controlled by alignment module 236.

Displacement analysis module 210 is configured to calculate a displacement for each target 140 out of multiple targets 140 selected in multiple scanned frames 130 which are included in scanned area 120 of wafer 100. While not necessarily so, several targets 140 may be selected in each of the scanned frames 130. Also, the multiple scanned frames 130 may be all of the plurality of frames defined within scanned area 120, but a smaller amount of frames 130 may also be used.

Displacement analysis module 210 is configured to calculate the displacement for each of the targets 140 based on a correlation of: (a) an image associated with the respective target 140 (an image which was obtained during a scanning of wafer 100), and (b) design data corresponding to the image. The design data may be, for example, computer aided design (CAD) data, which is used for the planning and/or manufacturing of wafer 100.

The term "design data" used in the specification should be expansively construed to cover any data indicative of physical design of a specimen and/or data derived from the physical design (e.g. through complex simulation, simple geometric and Boolean operations, etc.). For example, the various formats of Computer Aided Design (CAD) data may be used as design data. Design data can be provided in different formats as, by way of non-limiting example, GDSII format, OASIS format, etc.

As discussed below, in implementations in which the format of the image associated with the target 140 and that of the design data differ (e.g. if the former is in a grayscale intensity image format while the latter is in a vector format), intermediate processing of at least one of them may be required prior to the correlation. Additional details and variations of possible ways in which displacement analysis module 210 may execute the correlation are provided in relation to stage 540 of method 500.

The displacement calculated for each of the multiple targets is indicative of the displacement of the corresponding target image to where it should have been, according to the design data. During the scanning of the die area, an estimated location of each scanned portion of the image with respect to some reference location of the image (e.g. the topmost leftmost corner of that die) is known. The estimated location with respect to the scanned image may be translated to a supposed location with respect to the design data.

Displacement analysis module 210 is further configured to determine a displacement (also referred to as "frame-displacement") for each of the multiple scanned frames 130, this determining based on the displacements calculated for multiple targets 140 in the respective scanned frame 130.

While the frame-displacement may have a physical meaning in at least some implementations of the invention, this is not necessarily so, and in other implementations its meaning may only be as an imaginary construct which is only defined as a result of a computation that is based on (though not necessarily solely on) the respective target-displacements.

Subsequent processing module 220 utilizes the frame-displacements determined by displacement analysis module 210. Subsequent processing module 210 is configured to generate calibration information that includes at least the displacements determined for the multiple scanned frames 130. As discussed below in more detail (e.g. in relation to stage 560 of method 500), the calibration information may include additional information such as information regarding the locations of each of those frames 130.

Apart from the calibration information, subsequent processing module 220 further generates a target database that includes target image and location information of each target of a group of database targets, the group including multiple targets in each of the multiple scanned frames 130.

The calibration information and/or the target database may be stored in data storage 240 and/or transmitted to an external system (or another unit of system 200) via an output interface 295.

The operation of system 200 and of the various components thereof may be better understood in view of the process of operation. While not necessarily so, the process of operation of system 200 may correspond to some or all of the stages of method 500. Likewise, method 500 and its possible implementations may possibly be implemented by a system such as system 200. It is therefore noted that embodiments of the invention discussed in relation to method 500 may also be implemented, mutatis mutandis, in a hardware counterpart as various embodiments of system 200, and vice versa.

System 200 may enable utilizing the calibration information and the target database for determining location information in an inspection of another wafer. The location information may be used for example for detecting defects in an inspection image of such another wafer.

As will be discussed below, system 200 may also include components which enable system 200 to utilize the calibration information and the target database for the determining of the location information in such an inspection (e.g. as exemplified in relation to the discussion of FIGS. 5, 6, 7, and 8). In some implementations of the invention, system 200 may enable utilization of the calibration information and/or the target database for implementations other than defect detection (such as determining location information in an inspection of another wafer or otherwise); e.g. system 200 may enable utilizing that location information in correction of a location of an inspection beam (e.g. electrons beam) used for that inspection.

Figure 4:
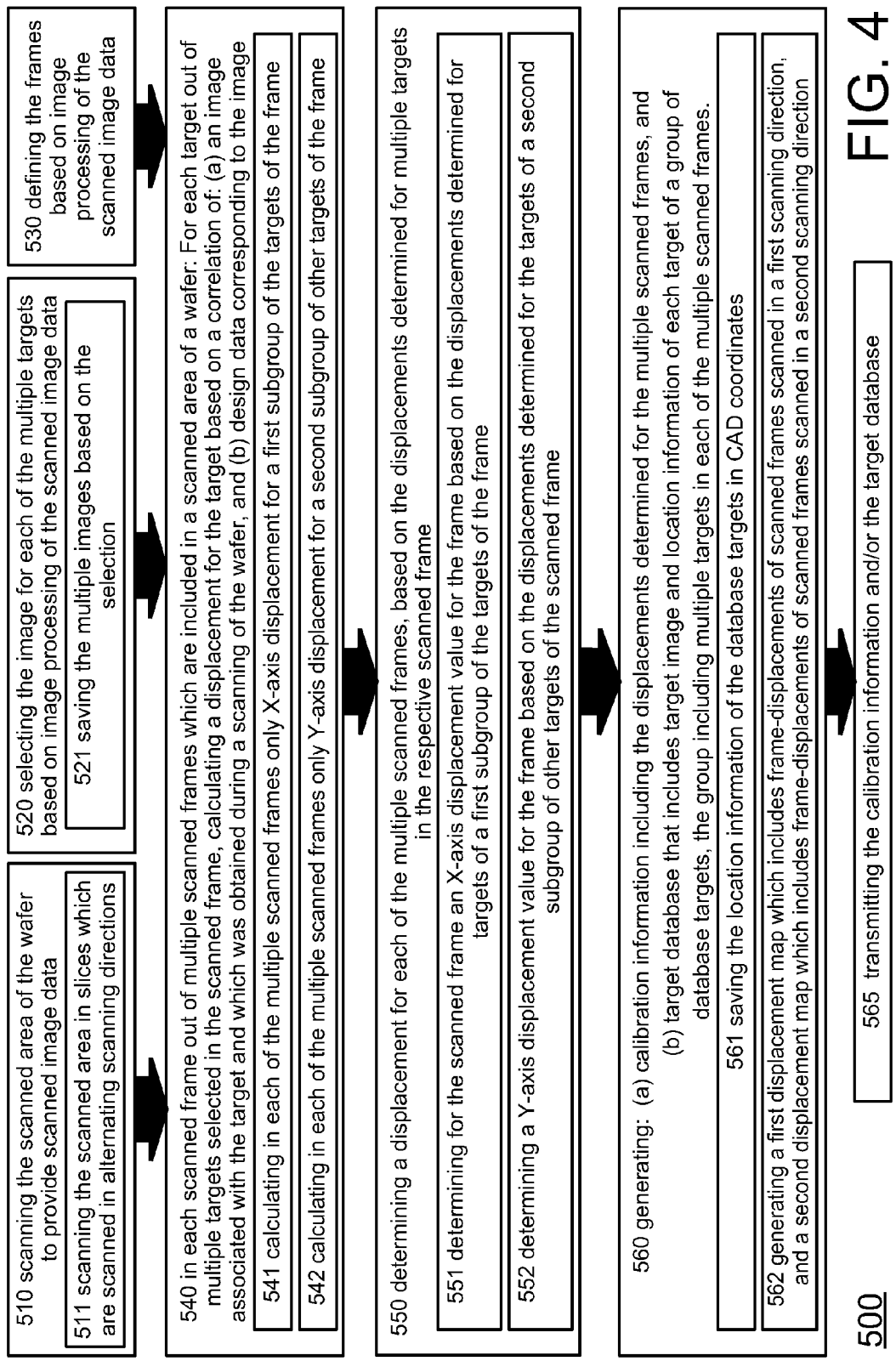

FIGS. 3 and 4 illustrate computerized method 500 for generating calibration information usable for wafer inspection, according to an embodiment of the invention. Referring to the examples set forth in the previous drawings, method 500 may be carried out by a system for generating calibration information usable for wafer inspection, such as system 200.

It should be noted that in wafers that include more than one layer, some or all of the disclosed stages of method 500 may be implemented for the same single wafer layer, and the method may be repeated (e.g. independently) for different layers (some or all of the layers of the respective wafer). Likewise, the method may be implemented for optical masks used in the manufacturing of wafers.

Referring to FIG. 3, method 500 includes stage 540 which is carried out for each scanned frame out of multiple scanned frames which are included in a scanned area of a wafer. The multiple scanned frames may include all of the plurality of scanned frames included in the scanned area of the wafer, or only some thereof.

In each scanned frame out of multiple scanned frames which are included in a scanned area of a wafer, stage 540 includes: for each target out of multiple targets selected in the scanned frame, calculating a displacement (herein below also referred to as "target-displacement") for the target. The calculating of the displacement for each of the targets in those scanned frames is based on a correlation of: (a) an image associated with the target and which was obtained during a scanning of the wafer, and (b) design data corresponding to the image. The design data may be computer aided design data (i.e. CAD data), but this is not necessarily so. Referring to the examples set forth in the previous drawings, stage 540 may be carried out by a displacement analysis module such as displacement analysis module 210.

While not limited to a single die in any way, the scanned area of the wafer may be a whole die or a part of it. Occasionally, the terms "the die area" or "the scanned area" would be used interchangeably with the term "the scanned area of the wafer". It should be noted that when the term "the die area" or "the scanned area" is used, it is not limited to a single die or a portion thereof. The scanned area of the wafer may also be referred to as "reference area" or "reference die", as displacements determined based on this area may later be used to correct displacement errors in other areas of the wafer (or of other, similar, wafers)

Referring to FIG. 9 as an example, the scanned area is divided into multiple scanned frames (e.g. frames 130). These frames may be adjacent and/or nonoverlapping with respect to one another, but neither of these characteristics is compulsory. Some of the ways in which such frames may be determined are discussed below. While not necessarily so, for the sake of clarity it is assumed that all the frames are rectangular, parallel to one another, and substantially parallel to at least one scanning axis in which the scanned area is imaged. For example, each frame may be defined by its anchor/start point $(X_0, Y_0)$, and by its dimensions $(d_x, d_y)$. As discussed below in more detail, the frames may be of identical size, but this is not necessarily so, and frames of intentionally distinct sizes may be defined within the die area. By way of example, a size of a frame may be 100 by 100 micrometers (μm).

While the frames may be defined in relation to a specific scanned image of the wafer, they could only be regarded as constructs which are defined in relation to the wafer and/or to design data (e.g. CAD data) that includes design details of the wafer.

Multiple targets (e.g. targets 140) are defined in each of the frames. Some of the ways in which such targets may be determined are discussed below. While not necessarily so, for the sake of clarity it is assumed that all the targets are rectangular, parallel to one another, and substantially parallel to at least one scanning axis in which the scanned area is imaged. For example, each target may be defined by its anchor/start/center point $(X_0, Y_0)$, and by its dimensions $(d_x, d_y)$. The targets may be of identical size. As is discussed below, the targets may be selected based on an analysis of scanned image data acquired during a scanning of the scanned area, based on content thereof. Specifically, each of the targets may include a pattern which is identifiable within its environment. The size of such an environment may vary, e.g. based on the expected dislocation errors in a given imaging scenario. It should be noted that in other implementations, the targets may be selected based on an analysis of the design data, in addition to or instead of the processing of the scanning image data.

Reverting to FIGS. 3 and 4, and to the calculating in stage 540 of the displacement for each of the multiple targets (such displacements calculated for targets are also referred to as "target-displacement"). The calculating of stage 540 of a target-displacement for each of the multiple targets is based on a correlation of an image associated with the respective target (an image which was obtained during a scanning of the wafer), and a corresponding design data. The images of the different targets may be of identical size (e.g. 32 by 32 pixels), but this is not necessarily so.

As aforementioned, most or all of the targets may include patterns that are identifiable within the environment of the respective target. The identifiability of the patterns of the targets may be a key factor in the selection (e.g. in stage 520) of the targets based on the scanned image. Some of the other factors that may affect the selection of the targets based on the scanned image are, for example, usability for determination of location and/or displacement in at least one direction.

Figure 11:
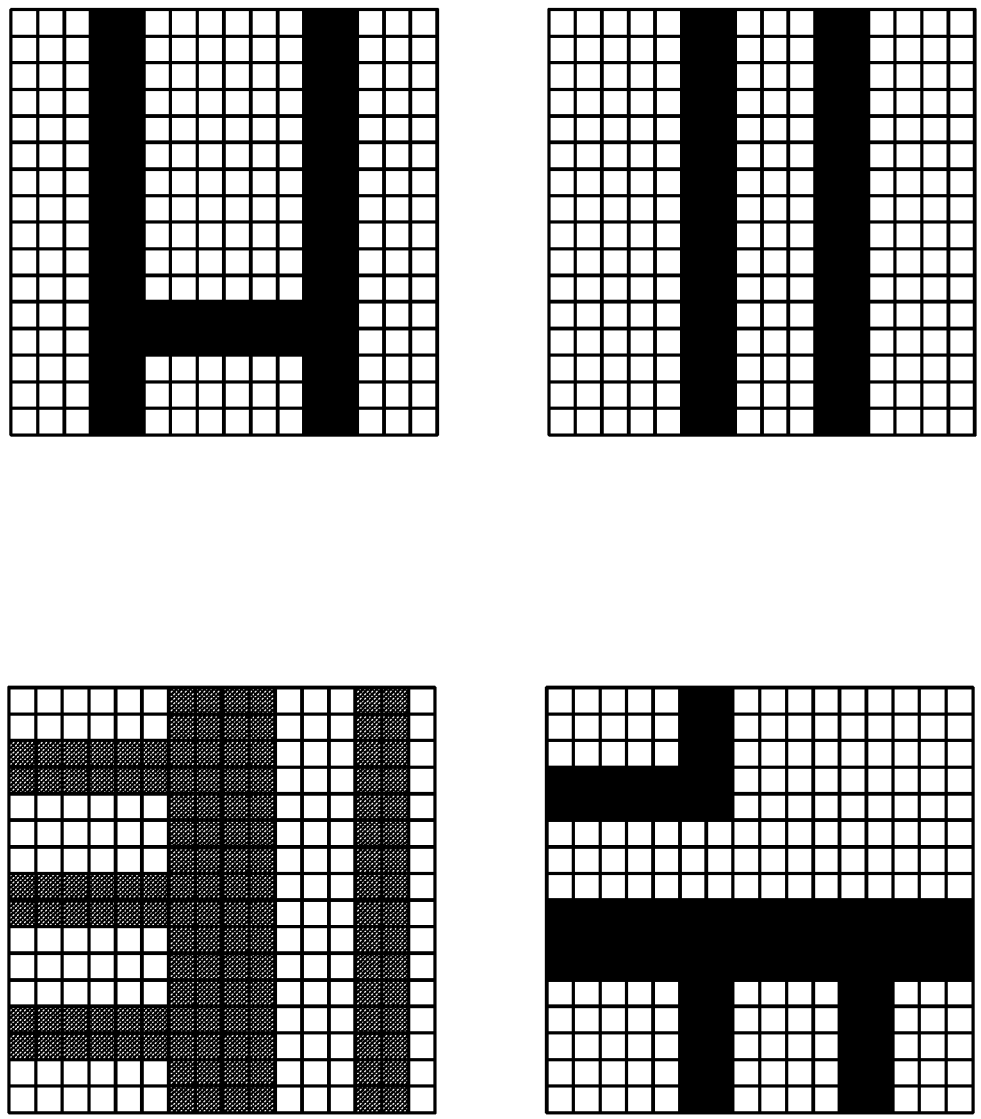
FIG. 11 is a representation of several patterns which may be selected for targets, according to an embodiment of the invention.

FIG. 11 is a representation of several patterns which may be selected for targets, according to an embodiment of the invention. In the illustrated example, each of the target images is a 16×16 pixels binary image. Clearly, other resolutions and color spaces may be implemented. The targets may either be directly identifiable (e.g. as exemplified in FIG. 11), or identifiable after implementation of one or more image processing algorithms or filters (e.g. closing and opening image processing operations) to the image data.

Reverting to the calculating of the displacement of the targets based on the correlation of the target images and the corresponding design data, it is noted that various types of design data may be used. The term "design data" used in the specification should be expansively construed to cover any data indicative of physical design of a specimen and/or data derived from the physical design (e.g. through complex simulation, simple geometric and Boolean operations, etc.). For example, the various formats of Computer Aided Design (CAD) data may be used as design data. Design data can be provided in different formats as, by way of non-limiting example, GDSII format, OASIS format, etc.

Some differences between the target images obtained from the scanning of the die area and the corresponding locations of the design data are likely to occur for various reasons—scanning conditions (e.g. illumination) as well as imperfections, shifts and outright errors in the scanning process, errors in the manufacturing of the electric circuit printed on the wafer, and so forth. Nevertheless, statistically significant correlation between the images and the design data may nevertheless be detected, especially if the targets are selected based (at least partly) on the identifiability thereof.

The displacement calculated for each of the multiple targets is indicative of the displacement of the corresponding target image to where it should have been, according to the design data. During the scanning of the die area, an estimated location of each scanned portion of the image with respect to some reference location of the image (e.g. the topmost leftmost corner of that die) is known. The estimated location with respect to the scanned image may be translated to a supposed location with respect to the design data.

Correlation between the target image and at least a portion of the design data may then be computed, and a similarly sized area of the design data in the environment of the supposed location whose correlation to the target image is the highest may then be selected. A distance between the supposed location and the location of the selected area may then be determined, and used as a base for the determination of the displacement (especially, the displacement may be equal to that distance). The selection of the selected area may follow a series of correlation steps (e.g. implementing Digital image correlation (DIC) techniques), wherein in each of these steps the target image is correlated to an area of the design data having a similar size to provide a correlation coefficient indicative of the degree of correlation between the two, and the area of the design data, whose correlation coefficient with respect to the target image is the largest, may then be selected.

It is noted that the target-displacements of the various targets may be determined as vectors (particularly, they may be determined as two dimensional vectors), but this is not necessarily so. Some or all of the target-displacements determined may be one dimensional (scalar). For example, if some (or all) of the targets are intended for determining of displacement only in one direction (e.g. an X-axis direction or a Y-axis direction), then a displacement value (scalar) may be determined for each such target, and not a vector. Clearly, even if a vector displacement is determined, a projection of that vector on any axis may be determined and later used in further computations.

The calculating of stage 540 is not necessarily carried out for each of the plurality of targets selected in each of the frames. For example, the number of targets selected in a given frame may be larger than the number of valid target-displacements required for successful execution of future stages of method 500. In another example, some of the target images may not be successfully correlated to any area of the design data, and may therefore be considered defective and not used in later stages of method 500. Also, calculating of target-displacement for targets in one or more of the multiple scanned frames may also be implemented for targets other than the aforementioned group of multiple targets. For example, selection of the multiple targets, out of all of the targets for which target-displacement was calculated, may be carried out after the selection—e.g. during stage 550 of determining.

Stage 550 of method 500 includes determining a displacement for each of the multiple scanned frames, wherein the determining of stage 550 is based on the displacements calculated for multiple targets in the respective scanned frame (that is, on the target-displacement of such targets). Such displacements determined in stage 550 for the scanned frames are also referred to as "frame-displacements". Referring to the examples set forth in the previous drawings, stage 550 may be carried out by a displacement analysis module such as displacement analysis module 210.

The determining of frame-displacements in stage 540 may be carried out in different ways, and different types of frame-displacements may be determined (in different implementations of the invention or even in a single implementation). For example, a vector (and especially a two-dimensional vector) displacement may be determined, indicating both direction of the displacement and the size thereof. In another example, a scalar indicating only the size of the displacement (either of a projection of the displacement on a known axis, or regardless of such an axis), only a direction of which, or another meaning.

While the frame-displacement may have a physical meaning in at least some implementations of the invention, this is not necessarily so, and in other implementations its meaning may only be as an imaginary construct which is only defined as a result of a computation that is based on (though not necessarily only on) the respective target-displacements.

The determining may include, for example, determining at least one (and possibly all) of the frame-displacements based on a result of averaging of the target displacements (wherein different types of averages may be implemented, e.g. arithmetic mean, median, geometric median, geometric mean, harmonic mean, quadratic mean, weighted mean, truncated mean, interquartile mean, midrange, winsorized mean, and so forth).

Such a frame-displacement may also be carried out by averaging target displacement in a first axis (e.g. the x-axis) independently from the averaging of the target displacements in another axis (e.g. the y-axis). The averaging of target displacements for providing components ("coordinates") of the frame-displacement separately (e.g. for providing an x-axis component and a y-axis component independently) may be executed on different sub-groups of the multiple targets. If, continuing the example offered above with relation to stage 540, a scalar displacement value is determined for each target in a frame, and not a vector, then each such target-displacement of a single target may only be averaged once—e.g. either for determination of x-axis frame-displacement value or for determination of y-axis frame-displacement value.

FIG. 10A illustrates a scanned frame 130 and graphical representation of corresponding part of the design data, denoted 910, according to an embodiment of the invention. While not the only possible implementation, the design data is also referred to below as "CAD data". It however may be another type of data (e.g. either vector or grayscale intensity image format data, generated by a computer or not, etc.).

The boundaries of the graphically represented corresponding part of the design data (denoted 910) are selected based on preliminary registration of the scanning to the design data (e.g. based on registration of a corner of the die 110—or of another die—before the scanning of the scanned area begins). It can be seen that due to displacement between the two regions (and also to other transformation such as linear stretching/compression, vertically, horizontally, or otherwise), different parts of the integrated circuit (illustrated by the background pattern in each of the areas denoted 910 and 130) are included in the scanned frame 130 and in the graphical representation of the corresponding part of the design data, denoted 910. The frame-displacement that may be determined for scanned frame 130 (e.g. in stage 550) may indicate an average displacement of different parts of the scanned frame 130. As aforementioned—not all of the parts of the scanned frame 130 are necessarily equally displaced. This may be the result of, for example, linear stretching or compression during the scan, scanning errors, and manufacturing errors.

The scanned frame 130 includes multiple targets (represented by squares 140) which were selected in it (e.g. in stage 520). The targets (for which the notion 140 will be used below, for the sake of clarity) are illustrated as square targets, but, as aforementioned, this is not necessarily so. The selection of the different targets 140 may be based on the content of the corresponding areas in the scanned image 130 (which is illustrated as confined within the respective squares 140).

Figure 10B:
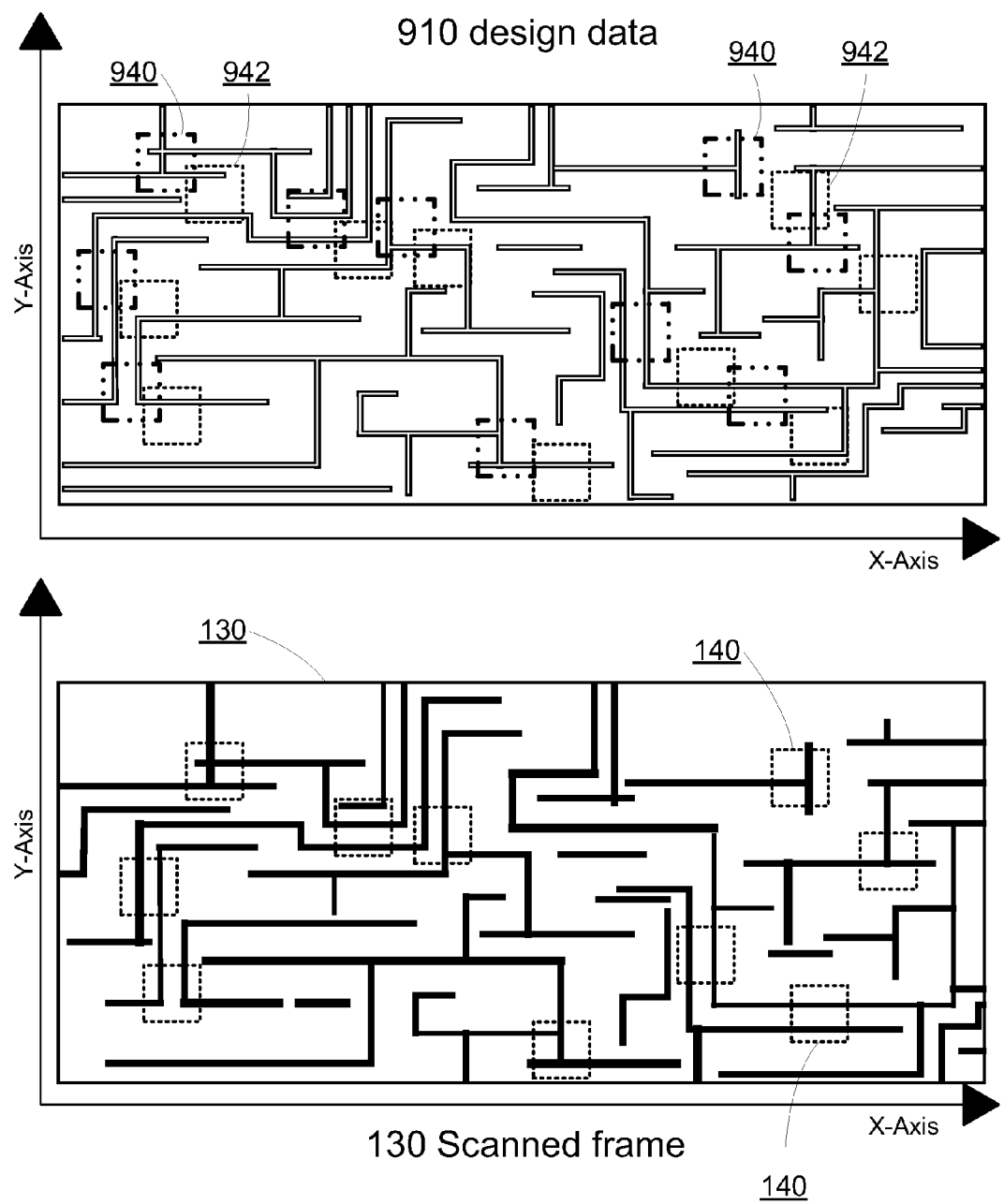

FIG. 10B illustrates the scanned frame 130 of FIG. 10B and the corresponding graphical representation of design data (denoted 910). On the latter, two sets of areas are illustrated. The first set of areas, denoted 942 and represented in monotonously dotted border lines, are located in similar locations with respect to the area denoted 910, as targets 140. That is, the squares denoted 942 may be regarded as the assumed locations of the targets with respect to the CAD data.

The second set of areas, denoted 940 and represented in wider, interchangeably dashed-double-dotted border lines, are areas that contain similar content to those of the respective targets 140 as illustrated in the example scanned frame 130. Each area 940 in the example illustrated, is located to the left and towards the top in respect to a corresponding area 942. However, it is not necessary that all of the areas 940 would be displaced in similar direction with respect to the corresponding areas 942.

Each of the areas 940 may be selected based on a correlation of the respective target image with the design data. If the design data is provided in grayscale intensity image format, it can be correlated with the scanned image data in a reasonably straightforward manner. However, if the design data is provided in vectorial format, the correlation may require additional interchangeably steps. For example, the correlation may be preceded by processing the vectorial design data to provide a corresponding grayscale intensity format image, which may then be correlated with the respective target image. Alternatively, the respective target image (if provided in grayscale intensity image format) may be converted to a vector format, wherein the correlation is done in a vector space.

Conversion of a vectorial design data to provide a corresponding grayscale intensity format image may be implemented in various ways, and may take into consideration (or otherwise simulate) various factors, such as target image pixel size, scanning machine characteristics and operating parameters, illumination parameters, optical parameters, target image statistics (e.g. average grey level), and so on and so forth.

Once a corresponding area 940 has been selected for each of the multiple targets 140 (or to some of the targets, e.g. in case the selection of corresponding area to one or more of the targets 140 fails), the distance between each of the targets (e.g. as represented by areas 942) and the corresponding area 940 may be determined (as well as projection of such distance on one or more axes, and/or direction of that distance with respect to any one or more such axes). For example, such distance may be determined between the corner pixels of each of the corresponding areas 940 and 942.

The calculating of the target-displacement for each of those targets (e.g. in stage 540) may be determined on that distance and/or other parameters—such as those discussed above.

Figure 10C:
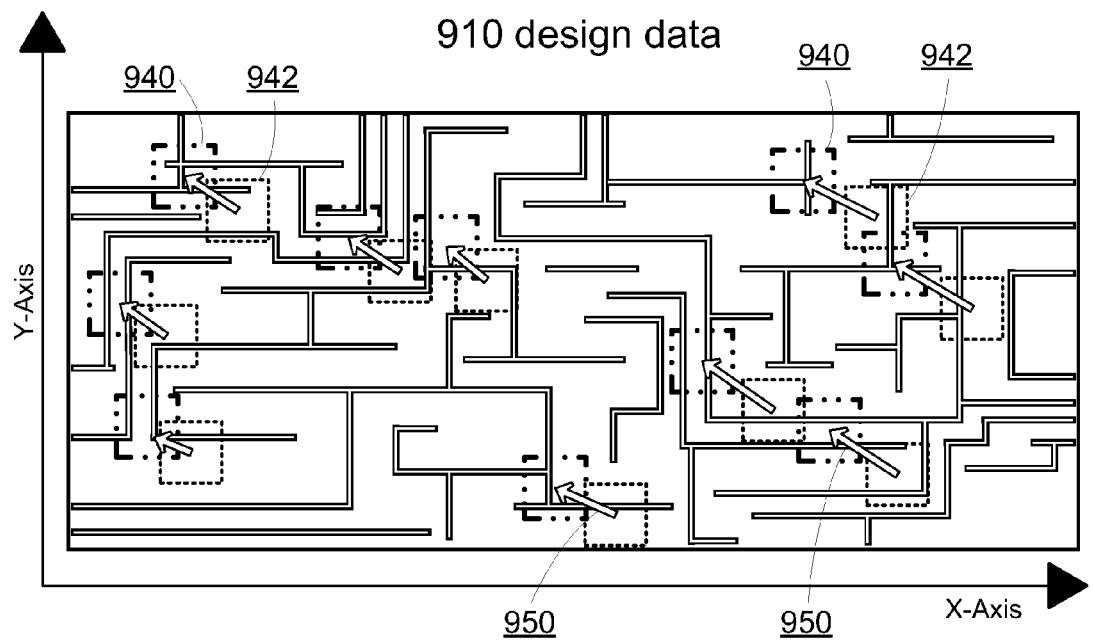

For example, in the example of FIG. 10C, the target-displacements 950 determined are equal (or at least based on, e.g. a truncated version thereof) to the distance between each two areas 940 and 950, and on the direction of such a displacement. In another way of representation, such a displacement 950 may be represented by an x-axis displacement and a y-axis displacement (or any other suitable two projections on two axes).

Figure 10D:
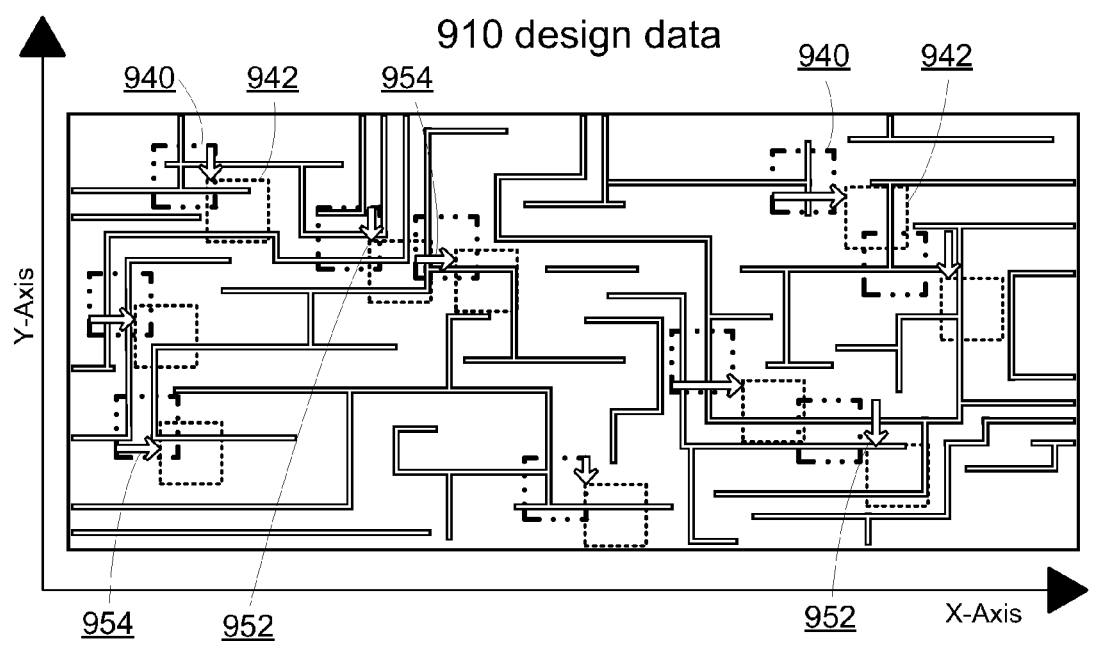

In the example of FIG. 10D, two types of target-displacements, 952 and 954, are illustrated. For some of the targets, displacements 952 are determined along the y-axis, while for other targets displacements 954 are determined along the x-axis. It should be noted that while not illustrated, displacement along two (or more) axes may be determined for one or more of the targets. The target-displacements 952 and/or 954 may be equal to the projection of the distance between two corresponding areas 940 and 942 on the corresponding x or y axes, and may also be calculated based on that distance and/or on such a projection thereof.

Once target-displacements (e.g. 950, 952, and/or 954) have been calculated for each of the multiple targets in the scanned frame 130, the corresponding frame-displacement 960 may be determined based on some or all of these target-displacements 950. As aforementioned, the determining of the frame displacement 960 may be executed by averaging one or more groups of targets out of the multiple targets.

The determining may include (or be preceded by) selection of the multiple targets that the displacements determined for which will be used for the determining of the frame-displacement of the scanned-frame in which those targets are included. For example, the determining may include (or be preceded by) selection of the multiple targets out of all of the targets for which target-displacement was calculated and may be carried out after the selection (e.g. selecting 80% of the targets having the middle displacement values).

Frame displacements may be determined in stage 540 to all of the plurality of scanned frames in the scanned area of the wafer, but this is not necessarily so. For example, frame-displacement for some other scanned frames may not be determined at all, or may be determined in other ways—e.g. based on frame-displacements determined for adjacent scanned-frames rather than on the target-displacements of targets within the respective frames.

It is noted that the determining of the frame-displacement for each of the scanned frames may be based only on the target-displacements of the multiple targets in it, but this is not necessarily so, and in other implementations it may also depend on additional parameters (e.g. number of such targets, location of the frame with respect to the die, physical properties of the area of the wafer corresponding to the scanned frame, and so forth).

It is noted that while stage 550 is illustrated as following stage 540, it may be carried out partly concurrently with it. For example, determining a frame displacement for a first scanned frame which was previously scanned may be carried out before the target-displacement values have been determined for targets of a second scanned framed scanned later than the first scanned frame. Generally, stages 540 and/or 550 may be carried out at least partly while the scanned area is being scanned.

Figure 12:
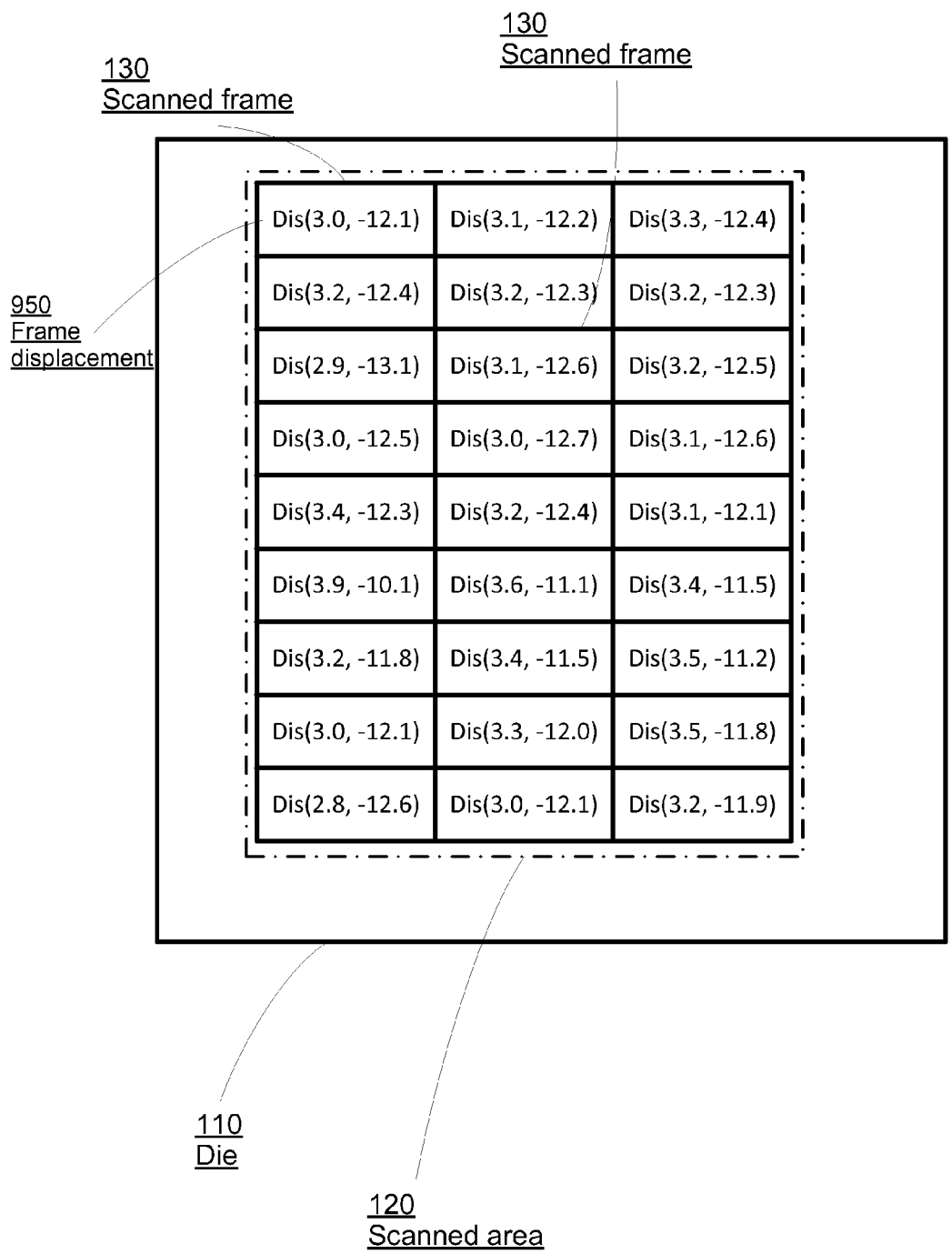
FIG. 12 illustrates frame displacements determined for multiple scanned frames scanned within a scanned area, according to an embodiment of the invention.

FIG. 12 illustrates the frame displacements 960 determined for multiple scanned frames 130 scanned within scanned area 120, according to an embodiment of the invention.

Reverting to FIG. 3, method 500 further includes stage 560 of generating: (a) calibration information including the displacements determined for the multiple scanned frames; and (b) a target database that includes target image and location information of each target of a group of database targets, the group including multiple targets in each of the multiple scanned frames. The location information of each of those targets may be determined with respect to an anchor point of the frame in which it is included (the displacements of the frames with respect to an external anchor point are referred to in the formerly discussed calibration information).

Referring to the examples set forth in the previous drawings, stage 560 may be carried out by a processing module such as subsequent processing module 220.

The generating of the calibration information may include generating of a table, an array (or any other one or more suitable data structures) that identify the different scanned frames, and include at least the frame-displacements determined for the multiple scanned frames.

For example, table 1 illustrates a data structure storing the calibration information generated in stage 560, according to an embodiment of the invention. Clearly, this is just an example, and other data structures may be implemented. Also, each of the fields is optional, and may be differently implemented, or not implemented at all.

The frame ID field stores an identifier identifying each of the multiple scanned frames. In the provided example, the unit digit represents the column, and the tenths digit represents the row, when referring to the example of FIG. 12.

The $X_{start}$ and the $Y_{start}$ fields indicate the position in which each scanned frame starts (e.g. the location of the top-left corner thereof). The units used may be those of the design data (e.g. CAD data)—such as micrometers (μm)—and may be those of the scanned image—e.g. pixels.

The $X_{length}$ and the $Y_{length}$ fields indicate the dimensions of each frame, e.g. in case different scanned frames are of different sizes. The units used may be those of the design data (e.g. CAD data)—such as micrometers (μm)—and may be those of the scanned image—e.g. pixels.

TABLE 1

| Frame ID | Xstart | Ystart | Xlength | Ylength | Xdisp | Ydisp |
|---|---|---|---|---|---|---|
| frame 1.1 | 0 | 0 | 120 | 40 | 3 | −12.1 |
| frame 1.2 | 0 | 40 | 120 | 40 | 3.2 | −12.4 |
| frame 1.3 | 0 | 80 | 120 | 40 | 2.9 | −13.1 |
| frame 1.4 | 0 | 120 | 120 | 40 | 3 | −12.5 |
| frame 1.5 | 0 | 160 | 120 | 40 | 3.4 | −12.3 |
| frame 1.6 | 0 | 200 | 120 | 40 | 3.9 | −10.1 |
| frame 1.7 | 0 | 240 | 120 | 40 | 3.2 | −11.8 |
| frame 1.8 | 0 | 280 | 120 | 40 | 3 | −12.1 |
| frame 1.9 | 0 | 320 | 120 | 40 | 2.8 | −12.6 |
| frame 2.1 | 120 | 0 | 120 | 40 | 3.1 | −12.2 |
| frame 2.2 | 120 | 40 | 120 | 40 | 3.2 | −12.3 |
| frame 2.3 | 120 | 80 | 120 | 40 | 3.1 | −12.6 |
| frame 2.4 | 120 | 120 | 120 | 40 | 3 | −12.7 |
| frame 2.5 | 120 | 160 | 120 | 40 | 3.2 | −12.4 |
| frame 2.6 | 120 | 200 | 120 | 40 | 3.6 | −11.1 |
| frame 2.7 | 120 | 240 | 120 | 40 | 3.4 | −11.5 |
| frame 2.8 | 120 | 280 | 120 | 40 | 3.3 | −12 |
| frame 2.9 | 120 | 320 | 120 | 40 | 3 | −12.1 |
| frame 3.1 | 240 | 0 | 120 | 40 | 3.3 | −12.4 |
| frame 3.2 | 240 | 40 | 120 | 40 | 3.2 | −12.3 |
| frame 3.3 | 240 | 80 | 120 | 40 | 3.2 | −12.5 |
| frame 3.4 | 240 | 120 | 120 | 40 | 3.1 | −12.6 |
| frame 3.5 | 240 | 160 | 120 | 40 | 3.1 | −12.1 |
| frame 3.6 | 240 | 200 | 120 | 40 | 3.4 | −11.5 |
| frame 3.7 | 240 | 240 | 120 | 40 | 3.5 | −11.2 |
| frame 3.8 | 240 | 280 | 120 | 40 | 3.5 | −11.8 |
| frame 3.9 | 240 | 320 | 120 | 40 | 3.2 | −11.9 |

The $X_{disp}$ and the $Y_{disp}$ fields indicate the frame-displacement of the respective scanned frame. The units used may be those of the design data (e.g. CAD data)—such as micrometers (μm)—and may be those of the scanned image—e.g. pixels. Other representations of the displacement may also be used (e.g. size and direction of displacement, (R,θ)).

As will be discussed in more detail below, the calibration information (which may also be referred to as "displacement map") may later be used in the scanning of other dies of the wafer (or of other wafers) during run-time mode.

Reverting to the target database, the generating of the target database may include generating the target database that includes target image and location information of all of the multiple targets of stage 540, but this is not necessarily so. Some of the targets whose target-displacement was used in stage 550 for the determining of the respective one or more frame-displacements may, in some implementations, not be included in the group of database targets. The number of targets from each of the scanned frames to be included in the group of database targets may be limited, for example, by memory size limitations of the recipe database (which may for example be part of the inspection tool).

While the generating of the target database may include generating the target database that includes the target images used for the correlation of stage 540, this is not necessarily so, and in other implementations other images may be used for some or all of the database targets. For example, images of different size, resolution, color depth or location may be saved, for some or all of the database targets.

The location information generated may be corrected location information corrected based on the frame-displacements determined. While the location information may be corrected based on the target-displacements of the respective targets, the correction based only on the respective frame-displacement may be favored.

In some implementations, the group of database targets includes at least two target images which are saved for later X-axis displacement correction and at least two are saved for later Y-axis displacement correction in each of the scanned frames. Other minimum numbers of images may clearly be selected, and more than the minimal number of targets may be saved. The selection of targets to be saved (i.e. the selection of the group of database targets) may be carried out during the set-up scanning runtime, and may be based on criteria such as uniqueness in the environment of the target, sufficient information and sufficient contrast. The number of targets selected may be limited by the storage in the recipe (to which those targets may be saved, along with the displacement maps).

Stage 560 may include saving of the calibration and/or the target database to one or more data storages (e.g. computer memory such as RAM, hard-disk, optical storage, etc.). The saving may include stage 561 of saving the location information of the database targets in design data coordinates (e.g. CAD data coordinates) such as micrometers.

Stage 560 may be followed by stage 565 (illustrated in FIG. 4) of transmitting the calibration information and/or the database targets—or parts thereof. The transmitting may include transmitting such data to one or more databases, to other one or more components of the same system, or to one or more other machines.

Stage 560 may be followed by stage 5400 of enabling utilizing the calibration information and the target database for determining location information in an inspection of another wafer. The location information may be used for example for detecting defects in an inspection image of such another wafer.

As will be discussed below, method 500 may also include the actual utilization of the calibration information and the target database for the determining of the location information in such an inspection. Some such ways of utilizing, which pertain to defect detections, are exemplified in relation to the discussion of FIGS. 5, 6, 7, and 8.

It is however noted that method 500 may also include enabling utilization of the calibration information and/or the target database for implementations other than defect detection (such as determining location information in an inspection of another wafer or otherwise). For example, method 500 may include enabling utilizing the calibration information and the target database for determining such location information in the inspection of the another wafer, and enabling utilizing that location information in correction of a location of an inspection beam (e.g. electrons beam) used for that inspection.

FIG. 4 illustrates computerized method 500 for generating calibration information usable for wafer inspection in more detail, according to an embodiment of the invention. The stages which are illustrated in FIG. 4 but not in FIG. 3 are optional, and the different possible combinations of those stages and of stages 540, 550 and 560 may be implemented in different embodiments of the invention.

Method 500 may include stage 510 of scanning the scanned area of the wafer to provide scanned image data. The scanning of the scanned area may be a part of larger parts of the wafer—e.g. a die, multiple dies, or even the entire wafer (or at least the parts of which that include electronic circuit parts). The scanning may be carried out in different techniques such as electron beam scanning and optical scanning. Referring to the examples set forth in the previous drawings, stage 510 may be carried out by any scanning, imaging and/or detecting apparatus such as sensor 230.

Since the scanning may be a lengthy process, some or all of the other stages (e.g. stages 520, 530, 540, 550, and/or 560) may be carried out at least partly concurrently with the scanning of one or more parts of the wafer, such as the scanning of the scanned area of the wafer in stage 510. Alternatively, stage 510 may precede stage 540, and possibly other stages of method 500 (e.g. stages 520, 530, 550, 560).

If method 500 includes scanning of a reference die (or other scanned area), information gathered during such a scanning may be used to generate the calibration information which may later be used to correct displacement errors when other dies of the wafer (or of other wafers) are scanned.

Method 500 may also include selection of the reference area (not illustrated), either prior to the scanning of at least part of the wafer, or as a result of such a scanning. The scanned area may be selected in different ways in different implementations of the invention—for example, it may be the first die of the first column (or the last die of that column) or of another column, it may be a substantially central reference die, etc.

Method 500 may further include additional stages that precede the optional scanning of the scanned area in stage 510, such as wafer alignment and translation of the wafer so that the reference area may be scanned. The global alignment of the wafer (e.g. by aligning a stage on which the wafer is positioned) may be based, for example, on CAD data, using coarse anchor points from the design data. The translation of the wafer may include translating the wafer to a position in which the reference die may be scanned.

The information required for successful execution of such preliminary stages may be retrieved from a previously determined recipe (or recipe parameters) and/or from a configuration file (referred to as "config") which does not pertain to a specific scan or to a specific layer of a wafer, but rather to a configuration of the scanning machine executed right after its manufacture (or at a later time, irrespective of any specific target to be scanned).

Method 500 may include stage 520 of selecting the image for each of the multiple targets based on image processing of the scanned image data. By selecting the images for the targets, the targets themselves may be selected. Referring to the examples set forth in the previous drawings, stage 520 may be carried out by an image processing module such as image processing module 250, which may and may not be part of the aforementioned displacement analysis module. It is noted that in other implementations, the targets may be selected based on processing of the design data (in addition or instead of the selecting based on the scanned image data). The selecting of the images for the different targets may be based on the content of such images—and its suitability for correlation with design data.

Stage 520 may include (or be followed by) stage 521 of saving the multiple images later used in stage 540, based on the selection. The saving may include saving for each of the multiple targets position information with regard to the scanned data (e.g. positions in pixels) and/or an estimated location of those target images (with respect to the design data). For example, scanned image information may be stored for a large number of targets (e.g. 100,000 targets in a die, each of which sized 32×32 pixels) whose estimated location is known (e.g. based on location information of the inspection system). As aforementioned, the selecting of stage 520 may be at least partly concurrent to the scanning of stage 510.

Method 500 may also include stage 530 of defining the scanned frames based on image processing of the scanned image data. The defining of the scanned frames may also be based on (additionally or instead of the scanned image data) the design data, required abilities of correction in future scans, capabilities of the machinery used for the scanning of the scanned area, for the calculation of the target-displacements and/or for the determination of the frame-displacements, etc. The defining of a frame may include defining its dimensions and/or its location. Referring to the examples set forth in the previous drawings, stage 530 may be carried out by an image processing module such as image processing module 250.

While not necessarily so, the defining of stage 530 may be at least partly concurrent to the scanning of stage 510, and/or to the selecting of stage 520. It is noted that, according to an embodiment of the invention, the defining of the frames may be based on results of the calculating of stage 540. For example, each frame may be defined so that the majority of the targets included therein have substantially similar target-displacements.

If the defining of the frames is based on the design data or is otherwise irrespective of the scanning data (e.g. based only on machinery capabilities), method 500 may include loading definitions of predefined frames (e.g. from the recipe or the config).

Referring to the number of frames defined in stage 530 (or otherwise determined), their number may be, by way of example only, 100-200 per slice, wherein each die may hold some 200 slices (the scanning of any die of a wafer or part thereof may be executed in elongated slices, substantially parallel to each other, which are scanned serially, usually in alternating scanning direction). In another example, e.g. when the pixel sizes implemented are smaller, the number of scanned frames per slice may be 300, and the number of slices may be 500.

The defining of the frames—either as part of method 500 (in stage 530) or preceding it (e.g. as part of the generation of the configuration file) may be implemented in various ways. In a first example, the determination of the frames (sizes and/or locations thereof) may be a result of a balancing between the machine scanning capabilities and the required abilities of correction in future scans (which relates to the type of distortion encountered). The smaller the frames are—the higher are the required computation capabilities, especially if real time implementation of either the first or the second methods is desired.

In implementations in which stage 530 includes defining the frames during the run time of the scanning, the distortion level may be measured during the set-up scanning, after data of multiple target windows is saved, and the frames may then be defined based on the distortion analysis. It is noted that if some areas of the scanned layer are not highly distorted, the amount of target windows in the (relatively large) frame defined may be reduced, thus saving data storage capacity, and future computation time.

For example, stage 540 may be based on frames of a fixed size (e.g. a minimal size), and based on the displacement determined for the targets of one or more of the frames, other frames may be defined (e.g. by splitting, combining, or otherwise modifying the preliminary frames).

Reverting to stages 540 and 550, it is noted that the calculating of the target-displacements and/or the determining of the frame-displacements may be implemented for X-axis displacements and for Y-axis displacements, e.g. as illustrated in FIG. 10D.

A frame-displacement vector (if indeed implemented as a vector) for the scanned frames may be determined by determining two scalar components independently of each other. E.g. target-displacement values of targets that were selected for X-axis displacement information gathering may be used for determining of an X-axis displacement value, and values of targets that were selected for Y-axis displacement information gathering may be used for determining of a Y-axis displacement value, and those two values may be saved as a displacement vector (or alternatively just as two scalar values).

For example, stage 540 may include stage 541 of calculating in each of the multiple scanned frames only X-axis displacement for a first subgroup of the targets of the scanned frame, and/or stage 542 of calculating only Y-axis displacement for a second subgroup of other targets of the scanned frame. Both X-axis and Y-axis displacements may be determined for a third subgroup of yet other targets, if implemented.

Continuing the same example, stage 550 of determining of the displacement for at least one of the scanned frames may further include stage 551 of determining for the scanned frame an X-axis displacement value for the frame based on the displacements determined for targets of a first subgroup of the targets of the frame (and, according to an embodiment of the invention, also of the third subgroup, but not of the second subgroup), and/or stage 552 of determining a Y-axis displacement value for the frame based on the displacements determined for the targets of the second subgroup (and, according to an embodiment of the invention, also of the third subgroup), wherein the determining of the Y-axis displacement value in stage 552 is irrespective of the displacements determined for the targets of the first subgroup.

Stage 541 and/or 542 may be carried out, if implemented, for targets in one or more of the multiple frames, or in all of them. Stages 551 and/or 552 may be carried out, if implemented, for one or more of the multiple frames, or for all of them.

Figure 5:
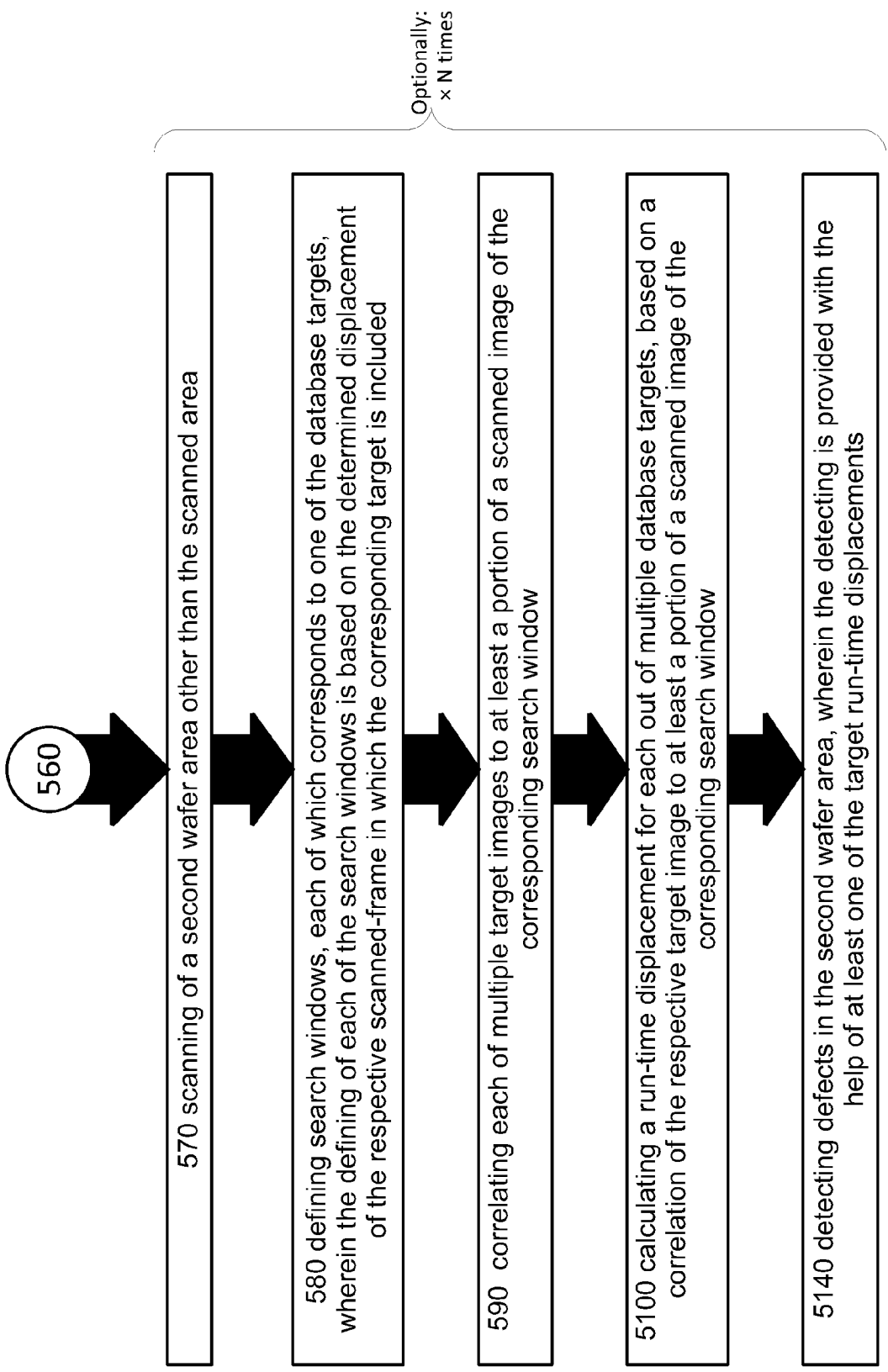

FIG. 5 illustrates additional stages of method 500, according to an embodiment of the invention. The stages illustrated in FIG. 5 are optional, and may be implemented in order to detect defects in a second wafer area other than the scanned area (whether on the same wafer or on another wafer) using the displacement values calculated for the scanned frames of the scanned area.

Stage 570, which may be carried out after stage 560 (and possibly after stage 565, if implemented), includes the scanning of a second wafer area. While not necessarily so, the second area is not the formerly discussed scanned area. As aforementioned, the second wafer area may be on the same wafer (e.g. another die, or within another die) or even on another wafer. If the second wafer area is located on another wafer, the other wafer and the originally scanned wafer would usually include similar electronic circuits (e.g. be wafers for the production of the same product, possibly from the same batch). The second wafer area would usually belong to the same layer as the originally scanned area (or to a corresponding layer, if it belongs to another wafer).

The content of the second wafer area would usually be similar to some or all of the content of the initially scanned area. For example, if the scanned area scanned in stage 510 is a whole die, the second wafer area may be a similar die (on either the same wafer or a similar wafer). Multiple frames may be defined within the second wafer area, wherein each of those frames may correspond to one or the scanned frames for which a frame-displacement was determined. Alternatively, if the frames of the second wafer area do not substantially cover similar content as the scanned frames, the displacement values of some scanned frames may be averaged. However, in the following description it will be assumed that each of the frames defined in the second wafer area corresponds to exactly one of the scanned frames, and includes substantially similar content (with some leeway which may exist for example due to scanning inaccuracy errors and other causes of inaccuracies).

While not necessarily so, the scanning of stage 570 may be executed by the same scanning machine which was used for the scanning of the scanned area (e.g. in stage 510). Using the same scanning machine for the scanning of those two wafer areas enables, inter alia, to compensate for displacement errors which are characteristic of that machine (e.g. x-y stage disposition errors, charging pattern if it is an electron beam scanner, and so on). Referring to the examples set forth in the previous drawings, stage 570 may be carried out by any scanning, imaging and/or detecting apparatus, such as sensor 230.

The scanning of the second wafer area in stage 570 and possibly of other areas of the same wafer may be executed during defect-detection run time. During defect detection run time, many wafers may be scanned for the detection of defects. For example, an entire batch of wafers which are manufactured together may be inspected for defects, or even multiple such batches. Since many wafers are possibly inspected for defects during the defect-detection run-time, and since a lengthy run-time defect detection process delays the manufacturing process, reducing the time required for the run-time defect detection is beneficial in at least some scenarios. In such scenarios, fast techniques for compensating for location inaccuracies and displacements may be desirable.

However, since the defect detection of many similar wafers may utilize calibration information (and target database) which was generated following a single determining of the frame-displacements (e.g. in a single instance of stage 560), time-consuming processing that is invested in stage 560 and/or in one or more of the stages preceding stage 560 has relatively small implications on the per-wafer overall defect detection time (to which the relative part of the duration of displacement evaluation may be added).

Figure 6:
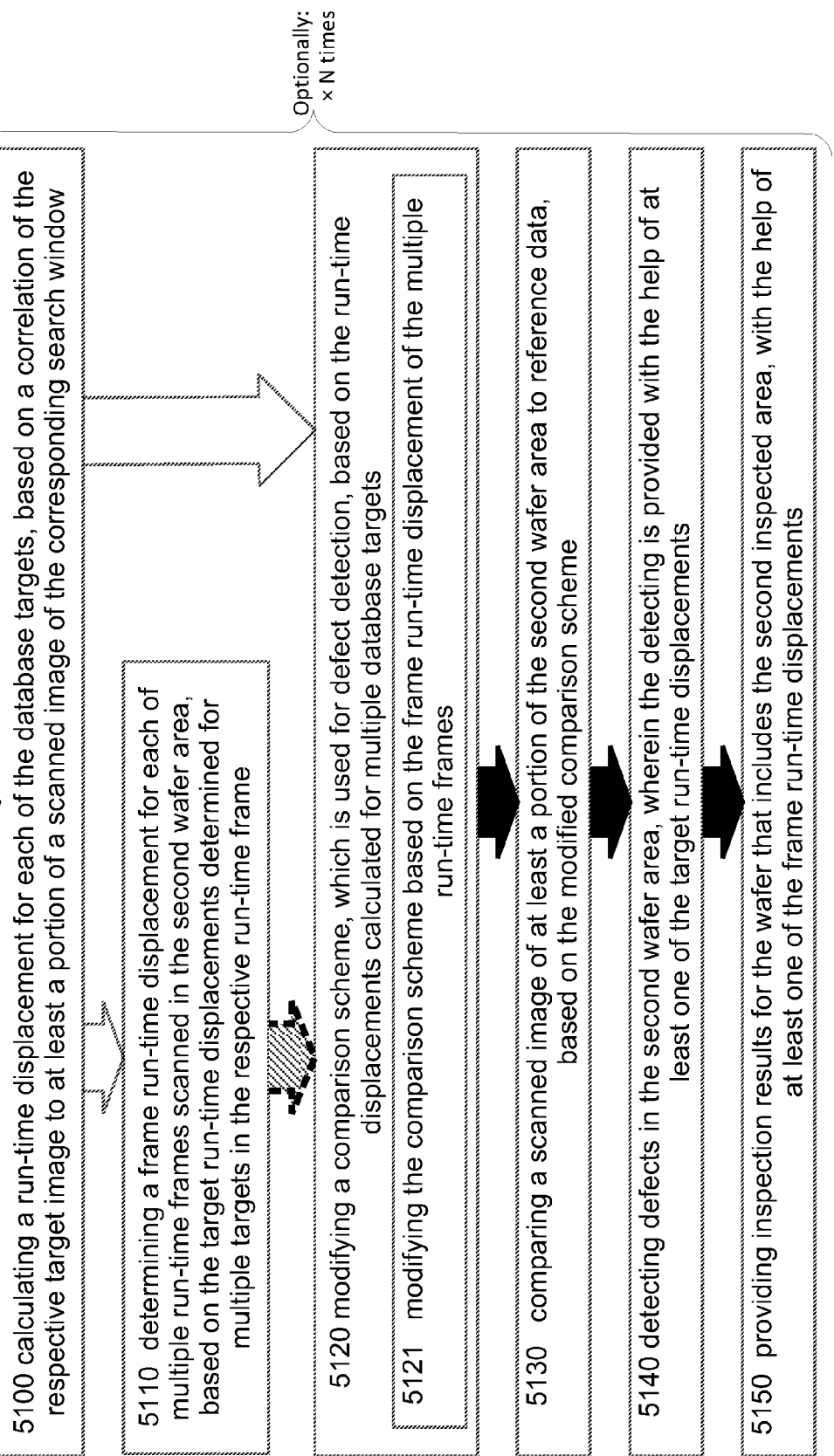

It should therefore be noted that some or all of stages 570 through 5140 which are illustrated in FIGS. 5 and 6 may be repeated for N different wafer areas (this is illustrated by the "×N times" denotement). Those N different wafer areas may be in a single wafer or in more than one wafer. For example, if each die in a batch of 25 similar wafers (each of which including some 150 dies), then the displacement results determined once for the scanned area of a single wafer (up until stage 560) may be utilized in the run-time defect detection for some 3,750 dies (=150*25). As will be discussed further below, the displacement values used for the second wafer area may be used for another area in the same wafer, and so on. The following discussion which pertains to FIGS. 5 and 6 would mainly focus on the implementation to a single wafer area (i.e. the second wafer area).

Stage 580, which is initiated after the beginning of the scanning of stage 570 (and possibly when stage 570 is done), includes defining search windows in the scanned image (or, possibly, images) of the second wafer area. Each of the search windows defined in stage 580 corresponds to one of the database targets. A corresponding search windows may be defined for each of the database targets, but this is not necessarily so, and fewer search windows may also be defined. The defining of each of the search windows in stage 580 is based on the determined displacement of the respective scanned-frame in which the corresponding target is included. Referring to the examples set forth in the previous drawings, stage 580 may be carried out by a correlator such as correlator 260.

As aforementioned, the location information generated in stage 560 of the group of database targets may be corrected location information corrected based on the frame-displacements determined. Such a correction may be (though not necessarily so) based only on the respective frame-displacement. Alternatively, if the location information from the target database is not corrected, the location information of the database targets may be corrected in stage 580 for the defining of the search windows.

The defining of the search windows includes defining the location of each search window, and possibly also the size thereof. It is noted that not necessarily all of the search windows are of the same size (for example, if the variance of target-displacements of targets of a given scanned frame was high, such data may be saved in the calibration information—and larger search windows may be defined in corresponding frames of the second wafer area).

The search windows defined are usually larger than the corresponding database targets, and are expected to include scanning image data similar to that of the corresponding target image (and clearly additional image data as well, of a nearby area of the wafer). For example, if a target image (e.g. similar to one of the illustrations of FIG. 11) is 32×32 pixels, then the corresponding search window defined in stage 580 may be, for example, 100×100 pixels.

Figure 13:
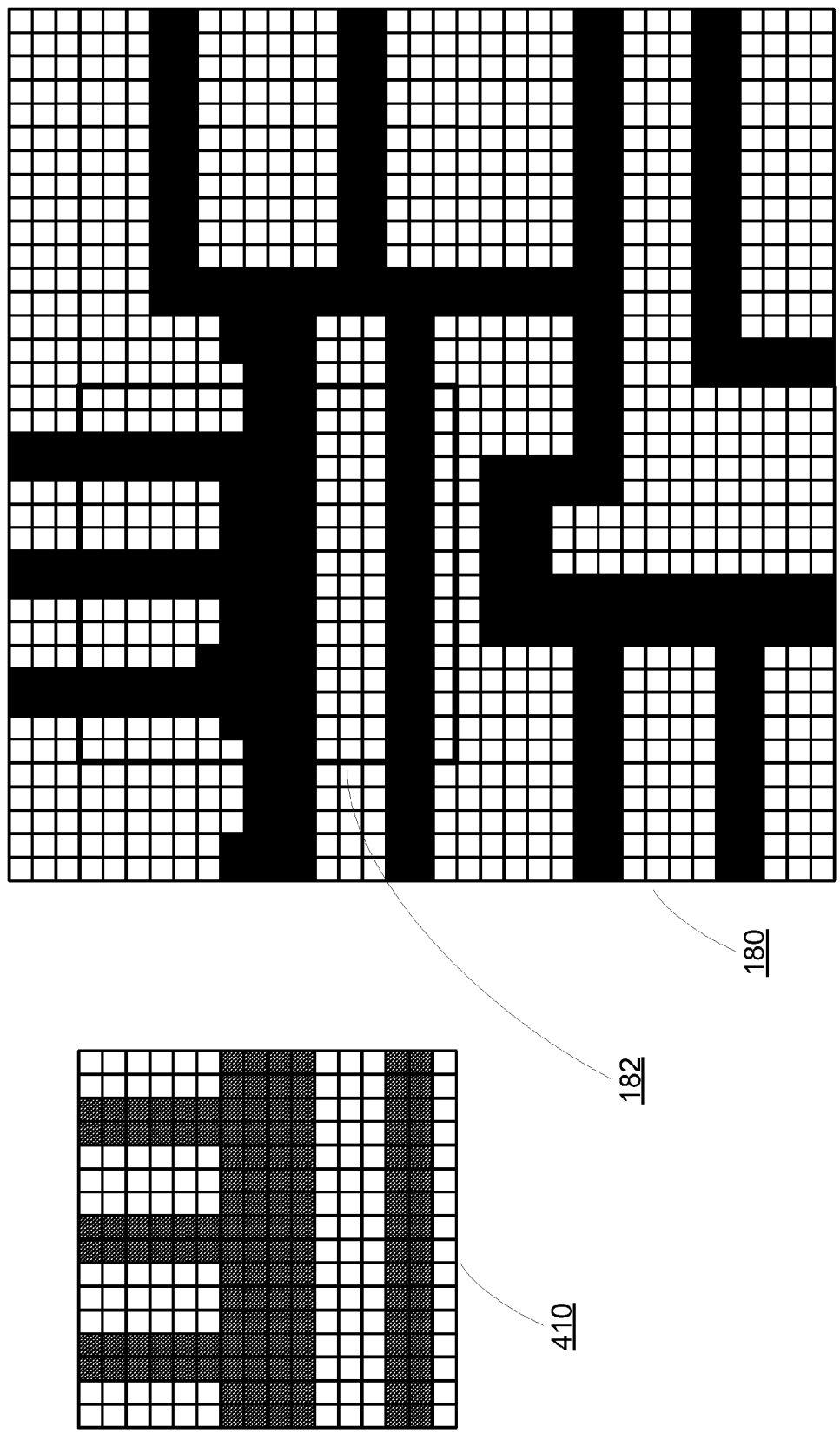
FIG. 13 illustrates a target image and a scanned image of a search window which is defined according to that target image, according to an embodiment of the invention.

FIG. 13 illustrates one target image 410 (e.g. as stored in the target database) and a scanned image of a search window 180 which is defined according to that target image 410, according to an embodiment of the invention. As can be seen, the search window defined (and the corresponding search image 180) is significantly larger than the target image 410 to which it corresponds, when comparing pixel size. Area 182 within the search window (this area is surrounded by a bold black border) corresponds to the target image 410 in size and in content. However, as can be seen—target image 410 and area 182 are not necessarily identical, e.g. due to manufacturing errors or inaccuracies in at least one of the scanning processes (the one yielding the target image and the other yielding the search window image), due to inconsistencies between such scanning processes (e.g. somewhat different lightening), and/or due to manufacturing errors in at least one of the corresponding wafer areas.

Figure 14:
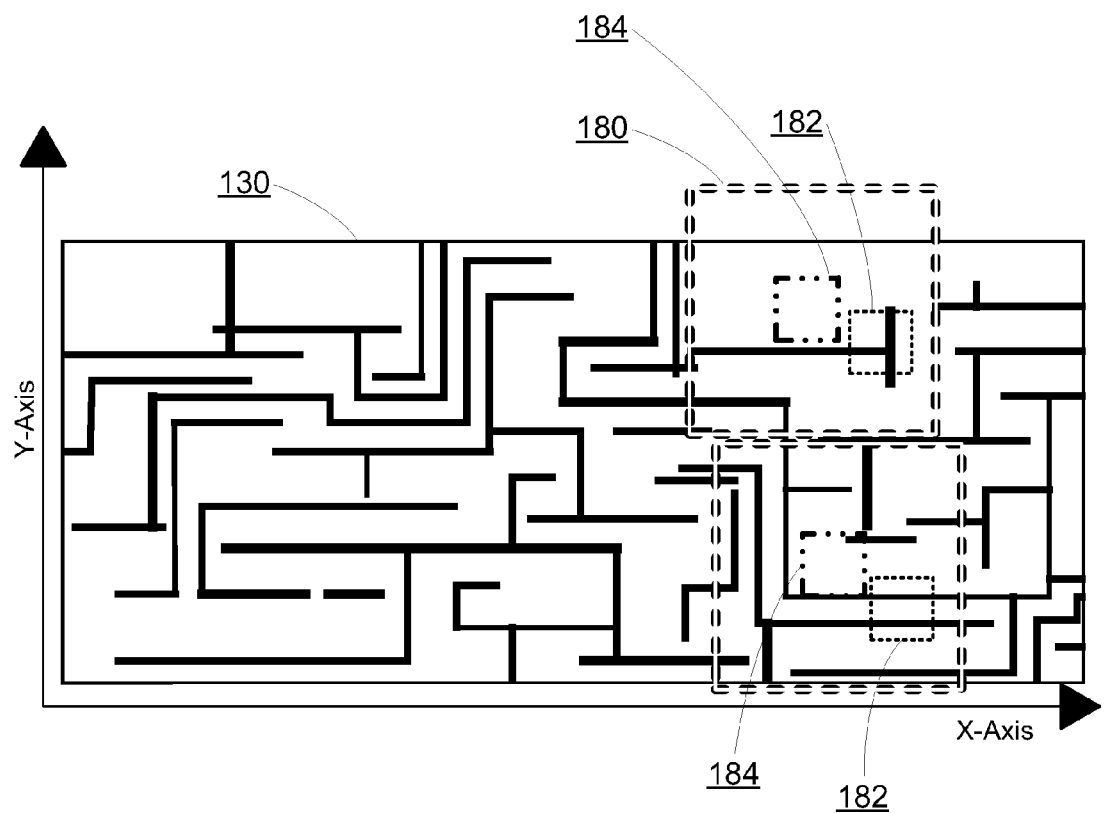
FIG. 14 illustrates two search windows which are defined within a frame of a scanned image of a scanned area of the wafer, according to an embodiment of the invention.

FIG. 14 illustrates two search windows 180 which are defined within a frame of a scanned image of a scanned area of the wafer, according to an embodiment of the invention.

Areas 184 are the estimated locations of targets. Based on those areas 184 the search windows 180 may be defined, and the areas 184 corresponding to the respective targets may be identified within the search windows 180.

Reverting to FIG. 5, stage 580 may be followed (or be at least partly concurrent with) stage 590 of correlating each of multiple target images (e.g. at least those for which a corresponding search window was defined in stage 580) to at least a portion of a scanned image of the corresponding search window. Referring to the examples set forth in the previous drawings, stage 590 may be carried out by a correlator such as correlator 260.

The correlating of stage 590 for each of the target images may include executing a series of correlations of the M by N pixels sized target image (e.g. 32×32 sized) with a series of similarly sized M by N pixels areas of the corresponding search window, and selecting the M by N area having the best correlation with the target image. The correlation may include correlations with all of the M by N pixels sized areas in the search window, but this is not necessarily so, and only some of them may be correlated.

While the correlation of the target image and the one or more portions of the scanned image of the corresponding search window may be symmetric for X-axis and Y-axis, this is not necessarily so. For example, targets that are selected for X-axis displacement assessment may be correlated with more significance to X-axis correlation, and targets that are selected for Y-axis displacement assessment may be correlated with more significance to Y-axis correlation.

For each of the search windows, a result of stage 590 may be an indication of part of the search window whose correlation to the target image is the best, and/or correlation results determined of multiple parts of the search window.

Method 500 continues with stage 5100 of calculating a run-time displacement for each out of multiple database targets (possibly for all of them), wherein the calculating for each of the multiple targets is based on a correlation of the respective target image to at least a portion of a scanned image of the corresponding search window (e.g. the correlation of stage 590). Similarly to the target-displacements in the scanned wafer area, the run-time displacements calculated for each of the multiple database targets is indicative of the displacement of a corresponding target image to where it should have been, according to the design data.

The run-time displacement may be calculated based on the distance between the location of the correlated portion of the search window (e.g. area 182 of FIG. 13) and the location information of the corresponding database target (e.g. as retrieved from the target database). The run-time displacement may also be calculated based on a distance between those two locations along an axis (e.g. the X-axis and/or the Y-axis). The run-time displacement, like the target displacement calculated in stage 540, may be a scalar displacement or a vector displacement, and may pertain to the overall displacement or only to displacement along an axis. Referring to the examples set forth in the previous drawings, stage 5100 may be carried out by a correlator such as correlator 260.

By stages 580 and 5100 (and possibly also 590), method 500 includes carrying out for each out of multiple targets of the database the following actions: (a) defining a corresponding search window based on the determined displacement of the scanned-frame in which the target is included; and (b) calculating a run-time displacement for the target, based on a correlation of the target image to at least a portion of an area of the scanned image which is defined by the corresponding search window.

Optional stage 5140, which is executed after stage 5100, includes detecting defects in the second wafer area, wherein the detecting is provided with the help of at least one of the target run-time displacements, and possibly with the help of all of them. Referring to the examples set forth in the previous drawings, stage 5140 may be carried out by a defect detection module such as defect detection module 270.

Stage 5140 may be followed by a stage of reporting some or all of the defects (e.g. as part of the inspection results provided in stage 5150), wherein the reporting may include reporting location information of at least one of the defects (and possibly of all of them) in coordinates of the design data (e.g. in high accuracy, and relative to CAD origin or another anchor point identified therein). It should be noted that the determining of stage 5140 may include determining for each of the detected defects a location in coordinates of the design data (e.g. in CAD coordinates). The defects may be associated in high accuracy to design data, which may enable various utilizations such as (though not limited to) design based classification.

The detecting of defects, other than dependency on at least one of the run-time displacements, may be similar to known practices of defect detecting. For example, the detecting of defects in stage 5140 may include comparing between the scanned image of the second wafer area, and reference data. Such reference data may be design data (e.g. CAD data) in Die-to-Database (D2 DB) defect detection techniques, and may be scanned image data of other parts of the wafer in Die-to-Die (D2D) or Cell-to-Cell (C2C) defect detection techniques. Such other parts may belong to the second wafer area, or to other areas of the wafer.

All the more so, several such techniques may be implemented, in which defects in some parts of the second wafer area may be detected using D2 DB detection, while defects in other parts of the second wafer area may be detected using D2D and/or C2C detection.

The decision as to what comparison technique (e.g. D2 DB, D2D, C2C) will be used in each area of second wafer area (and possibly in other areas of the wafer) may be based on a predetermined comparison scheme (also referred to as "layout" or "die layout"), in which different portions of each die are assigned different comparison techniques.

Some of the manners by which the defect detection of stage 5140 may be executed with the help of one or more of the run-time displacements calculated in stage 5100 are detailed in relation to FIG. 6.

FIG. 6 illustrates additional stages of method 500, according to an embodiment of the invention. The stages illustrated in FIG. 6 are optional, and may be implemented in order to detect defects in the second wafer area with the help of one or more of the run-time displacement values calculated in stage 5100.

Method 500 may include stage 5110 of determining a frame run-time displacement for each of multiple run-time frames scanned in the second wafer area, based on the target run-time displacements determined for multiple targets in the respective run-time frame.

The determining of the frame run-time displacements in stage 5110 may be implemented similarly to the determining of the frame-displacements in stage 550 (for which several examples of implementation were provided), but this is not necessarily so.

Frame run-time displacements may be determined in stage 5110 for all of the frames in the second wafer area, but not necessarily so. Also, frame run-time displacements may be determined in stage 5110 for all of the frames which correspond to the multiple scanned frames of stage 550, but this is not necessarily so.

While the run-time frame-displacements may have a physical meaning in at least some implementations of the invention, this is not necessarily so, and in other implementations its meaning may only be as an imaginary construct which is only defined as a result of a computation that is based on (though not necessarily only on) run-time displacements calculated for the respective targets.

Method 500 may include stage 5150 of providing inspection results for the wafer which includes the second wafer area inspected wafer, with the help of at least one of the frame run-time displacements. This may be facilitated by executing stage 5140 as an intermediate step (and possibly other stages as well, such as stages 5120 and 5130), but this is not necessarily so. Optionally, the providing of stage 5150 may include providing some or all of the results of the defect detection of stage 5140. Referring to the examples set forth with respect to the previous drawings, stage 5150 may be carried out by a processor such as processor 290.

Apart from defect detection, the frame run-time displacements may also be utilized for other uses, such as improving an accuracy of the scanning of the inspection area, or parts thereof. For example, the scanning of the inspected area may include improving location accuracy of the scanning of at least one of the run-time frames based on the frame run-time displacement determined for another run-time frame. This may be implemented, for example, by correcting a direction of an electron beam which is used for the scanning of a given frame (or part thereof) based on the run-time displacement of a previous frame. Likewise, the improving of the accuracy may be implemented by correcting a direction and/or a location of a camera, a sensor, or a stage on which the wafer is placed, during a scanning of a given frame (or part thereof) based on the run-time displacement of a previous frame.

Method 500 may include stage 5120 of modifying a comparison scheme, which is used for defect detection, based on the run-time displacements calculated for multiple database targets. The modifying of stage 5120 may include updating the comparison scheme. In some implementations stage 5100 may be executed based on the calculations of stage 5100 and further based on the intermediary computations of stage 5110 (determining of the frame run-time displacements). In other implementations, computations other than those of stage 5110 may be used for the updating in stage 5120. Referring to the examples set forth in the previous drawings, stage 5120 may be carried out by a defect detection module such as defect detection module 270.

According to an embodiment of the invention, stage 5120 may include stage 5121 of modifying the comparison scheme based on the frame run-time displacement of the multiple run-time frames. Referring to the examples set forth in the previous drawings, stage 5121 may be carried out by a defect detection module such as defect detection module 270.

The modifying of the comparison scheme may include, for example, modifying defect detection instructions which pertain to different areas within the second wafer area (e.g. use D2D comparison instead of C2C comparison), and/or modifying the definitions of the areas to which such instructions apply. The redefining of the boundaries of such areas may be based on the run-time displacements computed beforehand in stage 5110 and/or 5120.

Other parameters that may be included in the comparison scheme are, for example, instructions not to look for defects in some areas (e.g. "do not compare to reference image"), and sensitivity level indications, indicating what counts as a defect (e.g. threshold levels).

Method 500 may further include stage 5130 of comparing a scanned image of at least a portion of the second wafer area to reference data, based on the modified comparison scheme. Referring to the examples set forth in the previous drawings, stage 5130 may be carried out by a defect detection module such as defect detection module 270. In such an implementation, the detecting of the defects in stage 5140 may be based on results of the comparing of stage 5130.

As aforementioned, some or all of stages 570 through 5140 which are illustrated in FIGS. 5 and 6 may be repeated for N different wafer areas (this is illustrated by the "×N times" denotement). Those N different wafer areas may be in a single wafer or in more than one wafer. In some implementations, that process of defect detection in each of those N different wafer areas may be based directly on the calibration information generated in stage 560 (based on the data of the original scanned area of the original wafer). However, in other implementations the process of defect detection in some of those N different wafer areas may be based on calibration processes previously carried out for previously processed wafer areas. For example, the defect detection in a given die in a slice of the wafer may be based on displacement and/or calibration calculations which were used for previously processed dies of the same slice in that wafer.

FIG. 7 illustrates additional stages of method 500, according to an embodiment of the invention. The stages illustrated in FIG. 7 are optional, and may be implemented in order to detect defects in each wafer area of a series of wafer areas (in one or more wafers), with the help of run-time displacement values computed for another area of the series.

Each of the stages illustrated in FIG. 7 is carried out—if implemented—after stage 560 is fully executed.

Optional stage 5200 includes scanning a series of multiple other wafer areas (i.e. other than the scanned area of the originally scanned wafer, indicated in stage 540), wherein each of these other wafer areas covers a different die (the entire die, or a portion thereof) of the same wafer. The series of other wafer areas may include, for example, all of the dies-area in a slice, wherein each die-area covers an area from a single die (but not necessarily all of it).

Figure 15B:
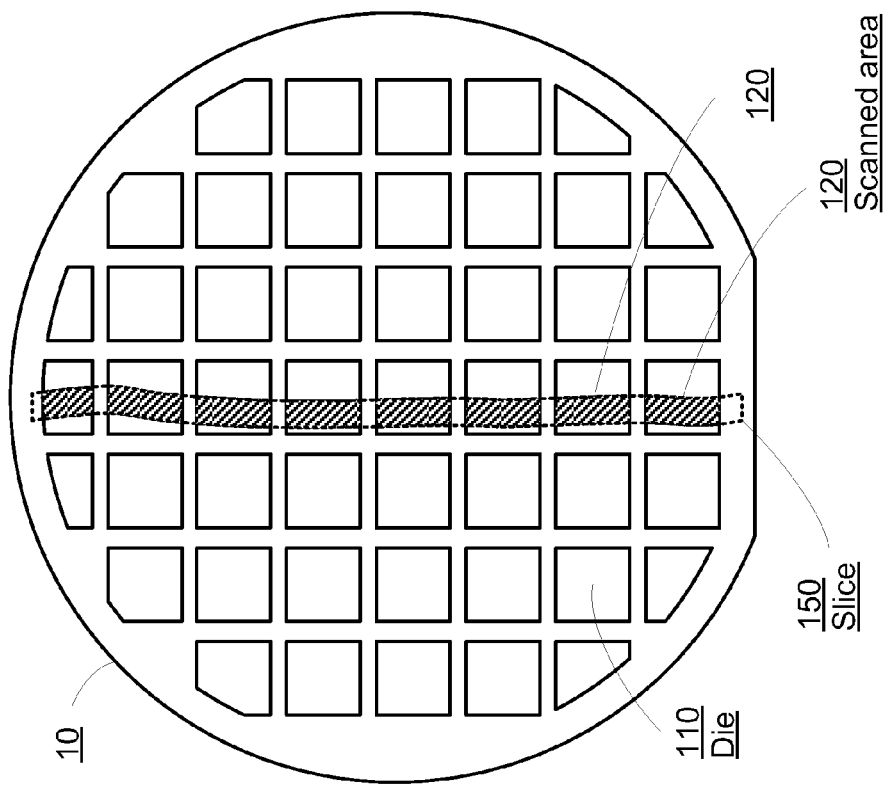
FIGS. 15A and 15B illustrate relationships between a wafer, dies of the wafer, a slice, and multiple scanned areas, according to an embodiment of the invention.
Figure 15A:
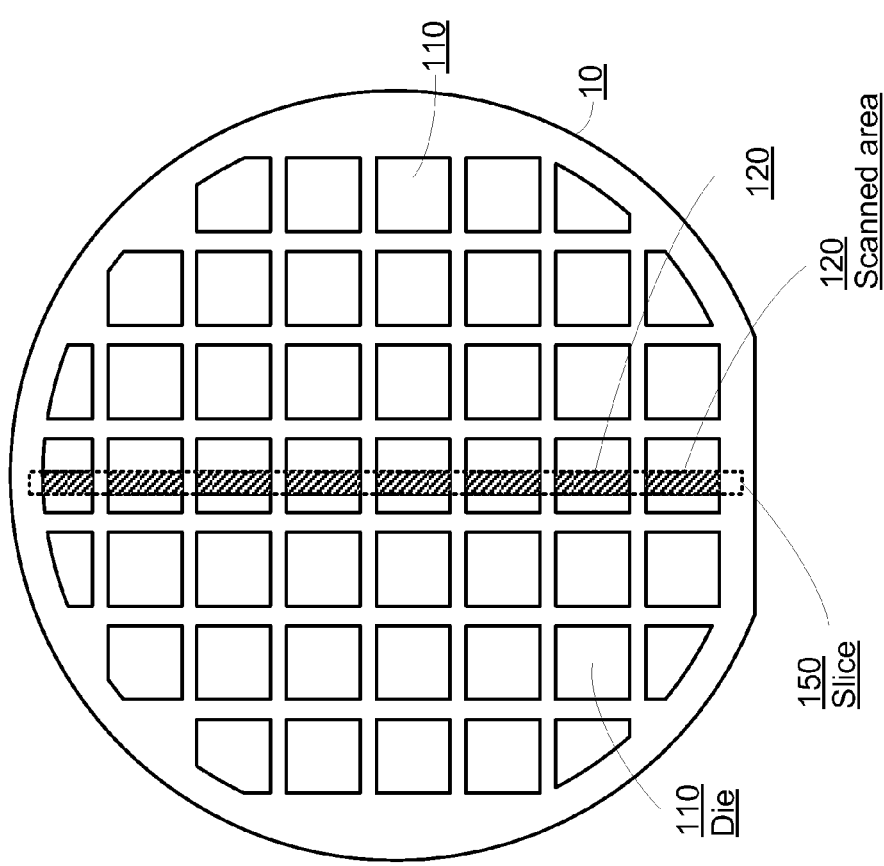

Referring to the examples of FIGS. 15A and 15B, the series of grey scanned areas 120 (illustrated as gray areas) includes the portion of a single slice 150 in each of the dies 110 in a single column of the wafer 10. It should be noted that while the actual slice 150 scanned is not necessarily perfectly linear as illustrated in FIG. 15A, the illustration of FIG. 15B is exaggerated with respect to normal conditions of wafer inspection. Usually the diversions from linearity of the slice 150 are far smaller (e.g. up to a few pixels, possibly sub-pixels), and could not have been seen in the scale of FIG. 15B.

Referring to the stages of method 500 discussed in relation to the previous figures, it is noted that stage 5200 may include multiple instances of stage 570, executed for different wafer areas other than the scanned area of stage 540. Especially, the series of other wafer areas may include the aforementioned second wafer area.

Stage 5200 may be followed, if implemented, by stage 5210 in which for each of the other wafer areas (other than the second scanned area) the following stages 5211, 5212, and 5213 are carried out.

Stage 5211 includes defining search windows which correspond to a subgroup which includes at least some of the database targets, wherein the defining of each of the search windows is based on a frame run-time displacement determined for a previous wafer area of the series. For example, the search windows for the subgroup of a third wafer area may be defined based on the frame run-time displacement determined for the second wafer area, and the search windows for the subgroup of a sixth wafer area may be defined based on the frame run-time displacement determined for a fifth wafer area (but in other implementations also—either in addition or alternatively—based on the frame run-time displacement determined for another one or more previous wafer areas of the series such as the second and/or the third wafer areas). Referring to the examples set forth in the previous drawings, stage 5211 may be carried out by a correlator such as correlator 260. It should be noted that search window in stage 5211 may be defined for other targets of the database targets, apart from those of the subgroup.

If the respective wafer area includes more than one frame, the search window may be defined based on the frame run-time displacement determined in the previous wafer area for the frame in which the corresponding target is included.

Since for each scanned area of the series, the search windows are defined based on the frame run-time displacement that was determined for a previous wafer area of the series, displacement values that are determined for one scanned area are used to refine the estimated location of the targets, and thereby possibly reduce the displacement error of the target location. Since the displacement errors may be smaller than would be possible without the correction, the size of the search windows may be reduced.

Assuming a given size of a target (e.g. a 32×32 pixels sized target), the search window in which a matching for the target is looked for in the second wafer area (e.g. the size of window that is defined in stage 580) may be significantly larger (e.g. a search window of 100×100). However, smaller search windows may possibly be defined for consecutive search areas of the series (because some accuracy may be gained from the matching of the target to an area within the search window of the first area). According to an embodiment of the invention, the size of at least one of the search windows defined for the subgroup targets is smaller than the size of a search window defined for the corresponding target in the second wafer area.

It should be noted that the subgroups of targets used in stage 5211 may differ between different wafer areas of the series.

Stage 5212 includes calculating a target run-time displacement for each of the targets of the subgroup, based on a correlation of the respective target image to a scanned image of the corresponding search window. While not necessarily so, the calculating of the target displacement in stage 5212 may be implemented similarly to the calculating of stages 540 and/or 5100. For example, it may include (or be preceded by) correlating a target image of each of the targets of the subgroup to at least a portion of a scanned image of the corresponding search window. Referring to the examples set forth in the previous drawings, stage 5212 may be carried out by a correlator such as correlator 260.

Stage 5213 includes detecting defects in the other wafer area, wherein the stage of detecting is responsive to at least one of the target run-time displacements. Referring to the examples set forth in the previous drawings, stage 5213 may be carried out by a defect detection module such as defect detection module 270. The detecting of the defects in stage 5213 may be preceded by various stages, and especially it may be preceded by stages which are based on the calculating of the target run-time displacements for each of the respective other wafer areas in stage 5212. While not necessarily so, such stages may be similar to stages 5110, 5120 and 5130, mutatis mutandis.

For example, method 500 may include for some or all of the other wafer areas executing the following stages, which are optional, and may be implemented in order to detect defect in the respective other wafer area with the help of one or more of the run-time displacement values calculated in stage 5212:

A stage of determining a frame run-time displacement for each of multiple run-time frames scanned in the respective other wafer area, based on the target run-time displacements determined for multiple targets in the respective run-time frame.

A stage of modifying a comparison scheme, which is used for defect detection, based on the run-time displacements calculated for multiple database targets. Such modifying may include updating the comparison scheme. The modifying of the comparison scheme may include, for example, modifying defect detection instructions which pertain to different areas of the respective other wafer area (e.g. use D2D comparison instead of C2C comparison), and/or modifying the definitions of the areas to which such instructions apply.

A stage of comparing a scanned image of at least a portion of the respective other wafer area to reference data, based on the modified comparison scheme.

As mentioned above, in some implementations, scanning of some or all of the areas of a wafer may be executed in elongated slices, substantially parallel to each other, which are scanned serially, usually in alternating scanning direction. A slice may include portions of multiple dies, and possibly from all of the dies in a column of dies in the wafer, e.g. as illustrated in FIG. 15A. The scanning of slices may be implemented by shifting the entire wafer by moving an entire stage on which the wafer is positioned along the elongated axis of the slice (e.g. the Y-axis direction). Once the scanning of a first slice in one direction is done, the adjacent slice may then be scanned in the opposite direction (e.g. by moving the stage in the opposite direction).

Reverting to FIG. 4, method 500 may include stage 511 of scanning (prior to the calculating, e.g. as part of stage 510) the scanned area of the wafer in slices which are scanned in alternating scanning directions. The scanning directions may be opposing each other (or substantially opposing each other), but this is not necessarily so. While the following explanation refers to a situation in which slices are scanned in opposite direction, it may be applied (with the required modifications) to any situations in which different parts of the wafer are scanned in different directions.

Figure 16:
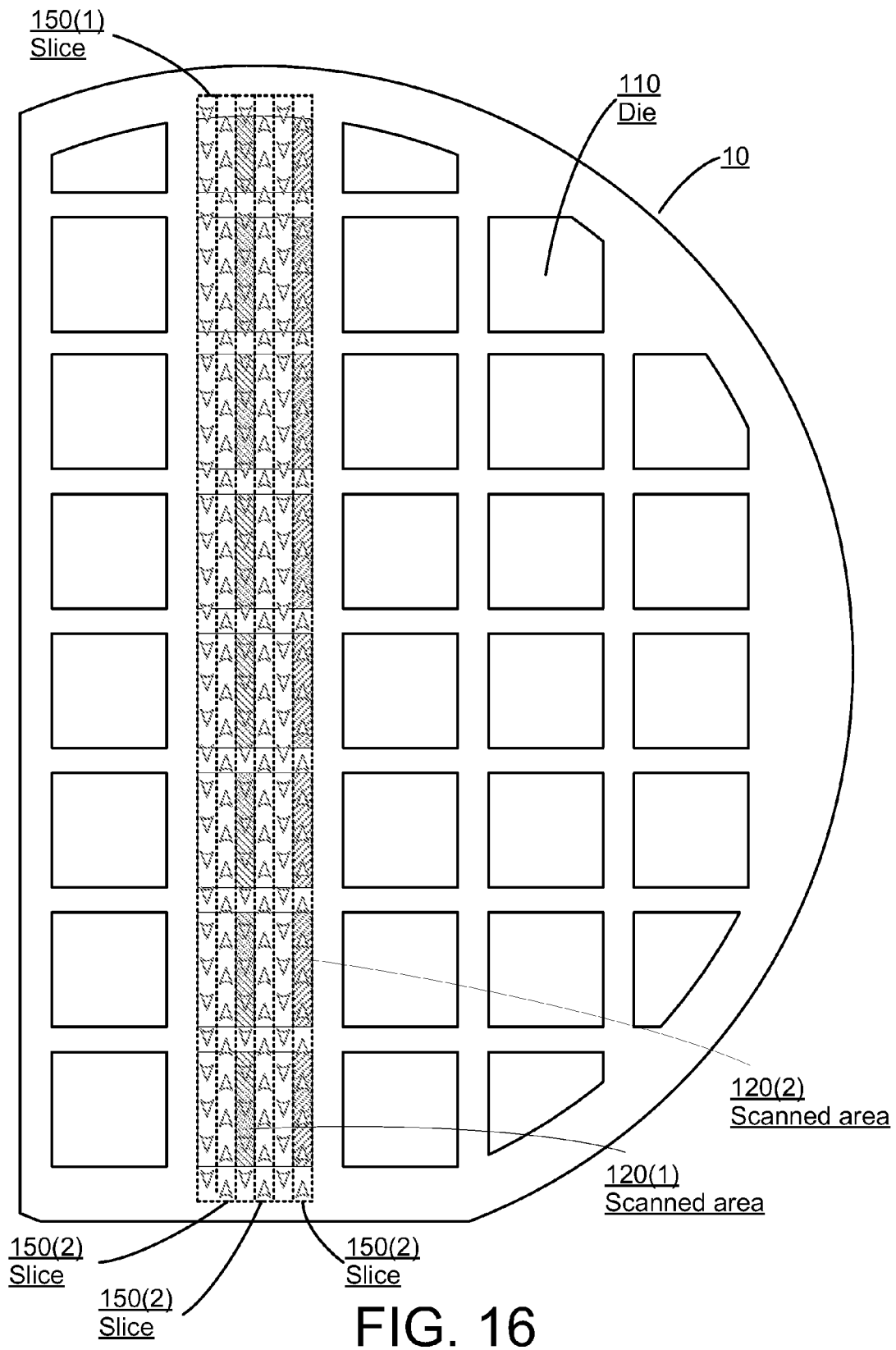
FIG. 16 illustrates scanning of a wafer in slices of alternating scanning directions, according to an embodiment of the invention.

FIG. 16 illustrates scanning of wafer 100 in slices 150 of alternating scanning directions, according to an embodiment of the invention. The slices denoted 150(1) are scanned in a first direction (from top to bottom of the drawings), while the slices denoted 150(2) are scanned in the opposite direction (from bottom to top of the drawing). The scanned areas 120 of adjacent slices are therefore scanned in the opposing direction (some of those areas are denoted and highlighted as 120(1) and 120(2), respectively).

Reverting to method 500, the generating of stage 560 may, in such an implementation, include stage 562 of generating a first displacement map which includes frame-displacements of scanned frames scanned in a first scanning direction, and a second displacement map which includes frame-displacements of scanned frames scanned in a second scanning direction. Referring to the examples set forth in the previous drawings, stage 562 may be carried out by a processing module such as subsequent processing module 220. Each of the displacement maps generated may be similar to the calibration information, but pertain only to areas of the wafer scanned in a similar scanning direction.

In such an embodiment, the transmitting of stage 565 may include transmitting the first and the second displacement maps, possibly as separate data structures.

The defect detection for defects in an analyzed frame of the second wafer area (if implemented) was disclosed above as being based on displacement determined for the respective scanned-frame of the scanned wafer area. However, if the analyzed frame is scanned in a scanning direction substantially different than the one in which the respective scanned frame was scanned, the displacement information determined for that scanned frame may possibly be less accurate than displacement determined for adjacent frames which were scanned in the same direction. By way of example, in electron beam scanning, the displacement in each frame may depend on the charge accumulated during scanning—and if two frames are scanned in opposite direction and therefore are scanned after different accumulation of charge, the displacements for those frames may be different.

FIG. 8 illustrates additional stages of method 500, according to an embodiment of the invention. The stages illustrated in FIG. 8 are optional, and may be implemented in order to detect defects in the second wafer area, if at least some of its frames are scanned in a direction other than the direction in which the respective frames of the scanned area of the wafer were scanned.

Stage 560 of generating of the target database may include stage 563 of generating target information of a subgroup that includes multiple targets in an analyzed frame out of the scanned frames, wherein the analyzed frame was scanned in a first scanning direction. The target information of each of the targets of the subgroup includes the target image associated with the target and location information.

Stage 570 that includes scanning of a second wafer area other than the scanned area may include stage 571 of scanning the second wafer area which includes a frame that corresponds to the analyzed frame and is scanned in a second scanning direction which is opposite to the first scanning direction.

Optionally, some or all of the scanned-wafer features in each of the run-time frames (and especially in the frame that corresponds to the analyzed frame) and in a corresponding scanned frame, substantially overlap.

The defining of the search windows in such an implementation may be preceded by stage 5300 of computing an averaged displacement by averaging frame-displacements of scanned frames that are adjacent to the analyzed frame and which were scanned in the second scanning direction. While the computing may be carried out after the scanning of the second wafer area (as illustrated), in other implementations it may be executed beforehand—e.g. as part of the generating in stage 560.

The defining of the search windows may be implemented as stage 581 of defining search windows which correspond to the targets of the subgroup, wherein the defining of each of the search windows is based on the averaged displacement.

Stage 581 may be followed by any combination of the aforementioned stages 590, 5100, 5110, 5120, 5130 and 5140. For example, stage 581 may be followed by calculating a target run-time displacement for each of the targets of the subgroup, based on a correlation of the respective target image to a scanned image of the corresponding search window; and detecting defects in the second wafer area, wherein the detecting is responsive to at least one of the target run-time displacements.

Reverting to FIG. 2, in which the aforementioned system 200 is illustrated, apart from recipe database 234, system 200 may include recipe interface 238 for retrieving the recipe (e.g. from a storage, from an external system), and possibly also for sending updates to the recipe. The same components 234 and 238 may be used for retrieving, storing, and/or updating of the config. In another implementation, other database and/or interface may be used for the retrieving, storing and/or updating of the config. It should be noted that the recipe and/or the config may be receiving from an external machine such as a CAD server (illustrated in FIGS. 17A and 17B) which is used for the storing and/or processing of the design data.

Many variations and possible implementations of system 200 would become clear to a person who is of skill in the art in view of method 500, and only some of those implementations will be discussed explicitly below.

For example, it is noted that subsequent processing module 220 may be configured to subsequently save the location information of the database targets in CAD coordinates.

System 200 may include an input interface 280 for receiving scanned image data (e.g. from sensor 230, from an external sensor or an external inspection system, etc.). Input interface 280 may be configured for receiving scanned image data of the scanned area 120 of wafer 100. Likewise, sensor 230 may be configured to scan at least the scanned area 120 of wafer 100, to provide corresponding scanned image data.

System 200 may also include image processing module 250, configured to process the scanned image data it receives. Image processing module 250 may be configured to select the image for each of the multiple targets 140, based on image processing of the scanned image data. Image processing module 250 may be further configured to save the multiple images based on the selection. Optionally, image processing module 250 may be configured to define the scanned frames based on image processing of the scanned image data.

Subsequent processing module 220 may be configured to determine the displacement for at least one of the scanned frames 130 by determining for the scanned frame an X-axis displacement value for the frame 130 based on the displacements determined for targets 140 of a first subgroup of the targets 140 of the frame 130, and determining a Y-axis displacement value for the frame 130 based on the displacements determined for the targets 140 of a second subgroup of other targets 140 of the scanned frame 130. It should be noted that while not necessarily so, the determining of the Y-axis displacement value by subsequent processing module 220 is irrespective of the displacements determined by it for the targets 140 of the first subgroup.

Input interface 280, if implemented, may also be used for receiving scanned image data of a second wafer area other than the scanned area. The second wafer area may be another area on the same wafer 100, or an area on another wafer. Sensor 230, if implemented, may be used for scanning the second wafer area. If the second wafer area belongs to another wafer, that other wafer may be positioned on the movable stage 232 before that scanning.

According to some embodiments of the invention, system 200 may be used for defect detection, apart from the creation of the correlation information and of the target database.

Figure 2B:
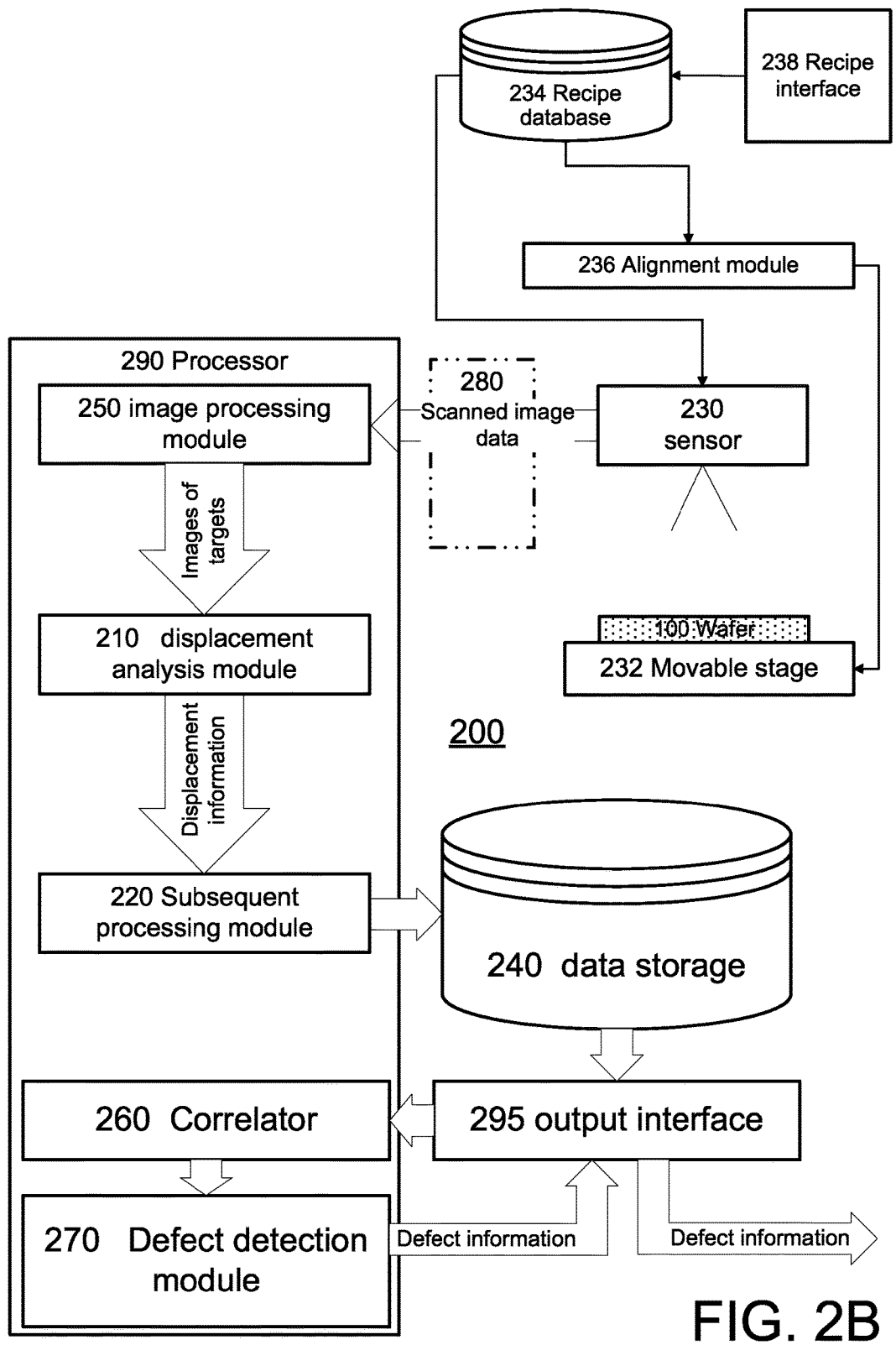

FIG. 2B illustrates system 200, according to an embodiment of the invention. System 200 may also include correlator 260. Correlator 260 may be configured to define search windows, each of which corresponds to one of the database targets, wherein the defining of each of the search windows is based on the determined displacement of the respective scanned-frame in which the corresponding target is included.

Correlator 260 may further be configured to calculate a run-time displacement for multiple database targets, based on a correlation of the respective target image to at least a portion of a scanned image of the corresponding search window.

If defect detection based on the correlation information is implemented in system 200, it may be executed by a defect detection module thereof, denoted 270. Defect detection module 270 may be used to detect defects in wafer areas other than scanned area 120—either in the same wafer 100 or in other wafer or wafers—based on information generated by the subsequent processing module 220. Especially, defect detection module 270 may be configured to detect defects in the second wafer area with the help of at least one of the target run-time displacements.

System 200 may further include an output interface (whether output interface 295 or another output interface) which is configured to report at least some of the defects (e.g. to an external system, to a display unit, to a human operator, etc.). Optionally, that reporting may include reporting location information of at least one of the defects in coordinates of the design data.

Correlator 260, if implemented, may be configured to determine a frame run-time displacement for each of multiple run-time frames scanned in the second wafer area, based on the target run-time displacements determined for multiple targets in the respective run-time frame; wherein defect detection module 270 in such an implementation may be further configured to modify a comparison scheme based on the frame run-time displacement of the multiple run-time frames. In such an implementation of system 200, defect detection module 270 may further be configured to compare a scanned image of at least a portion of the second wafer area to reference data, based on the modified comparison scheme and to detect defects in the second wafer area based on results of the comparing.

As aforementioned, in some implementations, defect detection module may be used to detect defects in several other wafer areas (possibly in multiple wafers, e.g. all of the wafers of a batch). Input interface 280 may be configured to receive (and/or sensor 230 may be configured to scan and accordingly generate) scanned image data of a series of multiple other wafer areas other than the scanned area. In the following description, it is assumed that this series includes the second wafer area, and that each of the other wafer areas covers a different die of the same wafer. However, as noted above, this is not necessarily so.

In such an implementation, correlator 260 may be configured to perform the following actions for each of the other wafer areas, other than the second scanned area:

define search windows which correspond to a subgroup which includes at least some of the database targets, wherein the defining of each of the search windows is based on a frame run-time displacement determined for a previous wafer area of the series, wherein the size of at least one of the search windows is smaller than the size of a search window defined for the corresponding target in the second wafer area; and calculate a target run-time displacement for each of the targets of the subgroup, based on a correlation of the respective target image to a scanned image of the corresponding search window.

Defect detection module 270 in such an implementation may be configured to detect defects in the other wafer area in response to at least one of the target run-time displacements.

Referring to the example of FIG. 16, it is noted that the scanning of the wafer may be executed in slices of substantially opposing direction. Input interface 280 may be used for receiving scanning results of a scan of the scanned area 120 of wafer 100 that was scanned in slices scanned in alternating scanning directions, as well as other areas of that wafer or of other wafers. Sensor 230, if implemented, may be configured to scan the scanned area 120 of wafer 100 in slices scanned in alternating scanning directions, as well as other areas of that wafer or of other wafers, and to provide respective scanning results (e.g. via input interface 280).

Subsequent processing module 220 may possibly be configured to generate, as part of the calibration information, a first displacement map which includes frame-displacements of scanned frames scanned in a first scanning direction, and a second displacement map which includes frame-displacements of scanned frames scanned in a second scanning direction.

Also, subsequent processing module 220 may be configured to generate, as part of the target database, target information of a subgroup that includes multiple targets in an analyzed frame out of the scanned frames, wherein the analyzed frame was scanned in a first scanning direction; wherein the target information of each of the targets of the subgroup includes the target image associated with the target and location information.

Continuing the same example, input interface 280 may be configured to receive scanned image data of a second wafer area other than the scanned area, wherein the second wafer area includes a frame that corresponds to the analyzed frame and is scanned in a second scanning direction which is opposite to the first scanning direction, and correlator 260 may be configured, in such an implementation, to: (a) compute an averaged displacement by averaging frame-displacements of scanned frames that are adjacent to the analyzed frame and which were scanned in the second scanning direction; (b) define search windows which correspond to the targets of the subgroup, wherein the defining of each of the search windows is based on the averaged displacement; and (c) calculate a target run-time displacement for each of the targets of the subgroup, based on a correlation of the respective target image to a scanned image of the corresponding search window. Defect detection module 270 may be configured to detect defects in the second wafer area in response to at least one of the target run-time displacements.

It should be noted that while system 200 was described as a single system, it may be implemented in two or more systems which communicate which each other. For example, it may be implemented as an inspection machine and a CAD server, which stores and processes design data. FIGS. 17A and 17B illustrate two implementations of implementing system 200 as an inspection machine 2100 and a CAD server 2200 that communicate with each other (either directly or indirectly). It should be noted that for reasons of clarity, not all the functionalities and components discussed above in relation to the various implementations of system 200 are represented in FIGS. 17A and 17B.

System 200 may include a recipe generator 2210 which is configured to determine (and possibly later update) a recipe which is used for the scanning of the wafer, and especially for the scanned area 120 and also of the other series of areas—e.g. if scanned by the same machine.

A communication module 2220 of the CAD server 2200 may be used to export the generated recipe to inspection machine 2100, which imports it using communication module 2120 thereof. The transmission which includes that transmission of the recipe from the CAD server 2200 to the inspection machine 2100 may include transmission of some or more of the following information:

- A comparison scheme (also referred to as "layout" or "die layout"), in which different portions of each die are assigned different comparison techniques.
- Wafer layout (which indicates the sizes of different dies on the wafer, and their location with respect to the wafer).
- Coarse alignment targets for global alignment of the wafer.

Alignment module 236 as well as image processing module 250 may be implemented as part of the inspection machine, and may align the wafer 100, e.g. using alignment that is based on coarse anchor points from the design data. Image processing module 250 in such an implementation would provide information on the selected targets (e.g. images and locations) to a design data processing module 2250 of the CAD server 2200, which would extract design data images corresponding to the target images selected by the inspection system 2100. It is noted that design data processing module 2250 may be configured to generate those images in grayscale intensity image format from vectorial design data, in order to enable correlation with the target images. Design data processing module 2250 may be configured to transmit to displacement analysis modules design data which pertains to relatively small areas (also referred to as "CAD clips").

The significant difference between the two implementations illustrated in FIGS. 17A and 17B is the location of displacement analysis module 210—in the implementation of FIG. 17A it is located in inspection machine 2100, while in the implementation of FIG. 17B it is located in the CAD server 2200.

Regardless of the way system 200 is implemented, it would usually include one or more components that are capable, inter alia, of processing data. For example, both displacement analysis module 210 and subsequent processing module 220 are capable of processing data. All such units which are capable of data processing may be implemented in hardware, software, or firmware, or any combination thereof. While in some implementations such processing capabilities may be implemented by dedicated software which is executed by general purpose processors, other implementations of the invention may require utilizing dedicated hardware or firmware, especially when volume and speed of processing of the data are of the essence.

Reverting to system 200, it will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

Reverting to method 500, it is noted that since method 500 is a computerized method, a program of instructions may be implemented, which when executed by one or more processors results in the execution of one of the aforementioned variations of method 500.

It would be clear to a person who is of skill in the art that instructions may be included in the program of instructions for executing some or all of the stages of method 500 (in all possible combinations suggested above), even if the inclusion of such instructions was not explicitly elaborated.

Referring to FIG. 18 which illustrates computerized method 600 for location based wafer analysis of at least one wafer, according to an embodiment of the invention. Referring to the examples set forth in the following drawings, method 600 may be carried out by a system such as system 300. While not necessarily so, the process of operation of system 300 may correspond to some or all of the stages of method 600. Likewise, method 600 and its possible implementations may possibly be implemented by a system such as system 300. It is therefore noted that embodiments of the invention discussed in relation to method 600 may also be implemented, mutatis mutandis, in hardware counterpart as various embodiments of system 300, and vice versa.

It will be clear to a person that is of skill in the art that once calibration information and target database were generated—either according to the respective stages of method 500 or otherwise, the utilization of this data to detect defects does not necessarily depend on the process in which this information is generated. For example, calibration information that includes frame displacements, and target database that includes target images and location information may possibly be generated without correlating between design data and scanned image data.

Method 600 discloses a process which may be regarded as similar to that illustrated in FIGS. 5, 6, 7 and 8—but which is irrespective of the way the calibration information and target database are implemented. For clarity of discussion, similar numbering was used in the disclosure of method 600—wherein the first digit in the number of each stage is changed from 5 to 6. That is—stage 670 is similar to stage 570 (though not necessarily identical or related), and so on. Therefore, for clarity and brevity of disclosure, some of the different variations, implementations and considerations which related to method 500 and its different stages are not necessarily explicitly repeated in full. That is, method 600 and each of its various stages may be implemented with the variations discussed in relation to the numerally corresponding stage of method 500, even if not explicitly elaborated.

Method 600 may start with stage 601 of obtaining: (a) calibration information that includes displacements of multiple frames included in a wafer area of a reference wafer, and (b) a target database that includes a target image and location information for each out of multiple targets in each of the multiple frames. Referring to the examples set forth in the following drawings, stage 601 may be carried out by calibration data input interface 301. Stage 601 does not have a single stage of method 500 which corresponds to it, but in some implementations thereof, the obtaining may include executing some or all of stage 510 through 560 of method 500.

While not necessarily so, the obtaining of the displacements of the multiple frames may be a part of obtaining calibration information including the same. Especially, this obtaining may include obtaining the calibration information as specified with respect to method 500. For example, the obtaining may include obtaining the displacement for a system like system 200.

While not necessarily so, the obtaining of the location information of the targets may include obtaining the location information in computer aided design (CAD) coordinates.

The obtaining may include obtaining the displacements and/or the target database from a database, from another machine, and/or from the same machine which executes method 600. The machine from which the displacements and/or the target database is received may be a system like system 200, but this is not necessarily so, and the displacement and/or the target database may be generated in a process which differs from the process of method 500. In but one example, the generation of the displacements may not be based on correlating any scanning image data to design data, but rather on comparing scanning imaged data to high resolution reference image data.

As aforementioned, method 600 is a computerized method for location based wafer analysis of at least one wafer. The reference wafer of stage 601 (which is optionally also the wafer that the target images of the database image) may be one of the one or more wafers analyzed in method 600, but this is not necessarily so, and method 600 may include analysis of one or more wafers other than the reference wafer.

Method 600 continues with stage 670 of scanning an inspected area of an inspected wafer (which, as aforementioned, may be either the reference wafer or another wafer). The scanning of stage 670 provides a scanned image of the inspected area.

Referring to the examples set off in the following drawings, stage 670 may be carried out by sensor 330. The scanning may be implemented by any type of suitable sensor, such as an optical sensor, electron beam sensor, and so forth.

Stage 680 of method 600 includes defining search windows, each of which corresponds to one of the targets of the database, wherein the defining of each of the search windows is based on the displacement of the respective frame in which the corresponding target is included (the displacement which was obtained in stage 601). Referring to the examples set forth in the following drawings, stage 680 may be carried out by a correlator such as correlator 360. The search windows may be defined with respect to the scanned image data of the inspected area obtained in stage 670.

Stage 6100 of method 600 includes calculating a run-time displacement for each of the targets, based on a correlation of the target image of the respective target to at least a portion of a scanned image of the corresponding search window. Referring to the examples set off in the following drawings, stage 6100 may be carried out by a correlator such as correlator 360.

By stages 680 and 6100 (and possibly also 690), method 600 includes carrying out for each out of multiple targets of the database the following actions: (a) defining a corresponding search window based on the displacement of the frame in which the target is included; and (b) calculating a run-time displacement for the target, based on a correlation of the target image of the target to at least a portion of an area of the scanned image which is defined by the corresponding search window.

Like the corresponding stage 5100, stage 6100 may be preceded by stage 690 that includes correlating each of multiple target images to at least a portion of a scanned image of the corresponding search window (a scanned image which is obtained in the scanning of stage 670). Referring to the examples set forth in the following drawings, stage 690 may be carried out by a correlator such as correlator 360.

As discussed below in more detail, optional stage 6140 of method 600 includes detecting defects in the inspected area, wherein the detecting is provided with the help of at least one of the target run-time displacements (and possibly with the help of all of them). Referring to the examples set forth in the following drawings, stage 6140 may be carried out by a processor such as processor 390, and especially by a defect detection module such as defect detection module 370.

Method 600 may further include a stage of reporting the defects, after the detecting. Optionally, this reporting may include reporting location information of at least one of the defects (and possibly of all of them) in coordinates of the design data (e.g. in CAD coordinates such as micrometers). It should be noted that the determining of stage 6140 may include determining for each of the detected defects a location in coordinates of the design data (e.g. in CAD coordinates).

The detecting of defects, other than its dependency on at least one of the run-time displacements, may be similar to known practices of defect detecting. For example, the detecting of defects in stage 6140 may include comparing between the scanned image of the second wafer area, and reference data. Such reference data may be design data (e.g. CAD data) in Die-to-Database (D2 DB) defect detection techniques, and may be scanned image data of other parts of the wafer in Die-to-Die (D2D) or Cell-to-Cell (C2C) defect detection techniques. Such other parts may belong to the second wafer area, or to other areas of the wafer.

All the more so, several such techniques may be implemented, in which defects in some parts of the second wafer area may be detected using D2 DB detection, while defects in other parts of the second wafer area may be detected using D2D and/or C2C detection.

The decision as to what comparison technique (e.g. D2 DB, D2D, C2C) will be used in each area of second wafer area (and possibly in other areas of the wafer) may be based on a predetermined comparison scheme in which different portions of each die are assigned different comparison techniques.

Some of the manners by which the defect detection of stage 6140 may be executed with the help of one or more of the run-time displacements calculated in stage 5100 are detailed in relation to FIG. 19.

FIG. 19 illustrates additional stages of method 600, according to an embodiment of the invention. The stages illustrated in FIG. 19 are optional, and may be implemented in order to detect defect in the inspected area with the help of one or more of the run-time displacement values calculated in stage 6100.

Method 600 may include stage 6110 of determining a frame run-time displacement for each of multiple run-time frames scanned in the second wafer area, based on the target run-time displacements determined for multiple targets in the respective run-time frame.

The determining of the frame run-time displacements in stage 6110 may be implemented similarly to the determining of the frame-displacements in stage 550 of method 500 (for which several examples of implementation were provided), but this is not necessarily so.

Frame run-time displacements may be determined in stage 6110 for all of the frames in the inspected area, but not necessarily so. Also, frame run-time displacements may be determined in stage 6110 for all of the frames which correspond to the multiple scanned frames of stage 650, but this is not necessarily so.

While the run-time frame-displacements may have a physical meaning in at least some implementations of the invention, this is not necessarily so, and in other implementations its meaning may only be as an imaginary construct which is only defined as a result of a computation that is based on (though not necessarily only on) run-time displacements calculated for the respective targets.

Method 600 may include stage 6150 of providing inspection results for the inspected wafer, with the help of at least one of the frame run-time displacements. This may be facilitated by executing stage 6140 as an intermediate step (and possibly other stages as well, such as stages 6120 and 6130), but this is not necessarily so. Optionally, the providing of stage 6150 may include providing some or all of the results of the defect detection of stage 6140. Referring to the examples set forth with respect to the previous drawings, stage 6150 may be carried out by a processor such as processor 390.

Apart from defect detection, the frame run-time displacements may also be utilized for other uses, such as improving an accuracy of the scanning of the inspection area, or parts thereof. For example, the scanning of the inspected area may include improving location accuracy of the scanning of at least one of the run-time frames based on the frame run-time displacement determined for another run-time frame. This may be implemented, for example, by correcting a direction of an electron beam which is used for the scanning of a given frame (or part thereof) based on the run-time displacement of a previous frame. Likewise, the improving of the accuracy may be implemented by correcting a direction and/or a location of a camera, a sensor, or a stage on which the wafer is placed, during a scanning of a given frame (or part thereof) based on the run-time displacement of a previous frame.

Method 600 may include stage 6120 of modifying a comparison scheme, which is used for defect detection, based on the run-time displacements calculated for multiple database targets. The modifying of stage 6120 may include updating the comparison scheme. In some implementations, stage 6100 may be executed based on the calculations of stage 6100 and further based on the intermediary computations of stage 6110 (determining of the frame run-time displacements). In other implementations, computations other than those of stage 6110 may be used for the updating in stage 6120. Referring to the examples set forth in the previous drawings, stage 6120 may be carried out by a processor such as processor 390, and especially by a defect detection module such as defect detection module 370.

According to an embodiment of the invention, stage 6120 may include stage 6121 of modifying the comparison scheme based on the frame run-time displacement of the multiple run-time frames. Referring to the examples set forth in the previous drawings, stage 6121 may be carried out by a processor such as processor 390, and especially by a defect detection module such as defect detection module 370.

The modifying of the comparison scheme may include, for example, modifying defect detection instructions which pertain to different areas of the inspected area (e.g. use D2D comparison instead of C2C comparison), and/or modifying the definitions of the areas to which such instructions apply. The redefining of the boundaries of such areas may be based on the run-time displacements computed beforehand in stage 6110 and/or 6120.

Other parameters that may be included in the comparison scheme are, for example, instructions not to look for defects in some areas (e.g. "do not compare to reference image"), and sensitivity level indications, indicating what counts as a defect (e.g. threshold levels).

Method 600 may further include stage 6130 of comparing a scanned image of at least a portion of the inspected area to reference data, based on the modified comparison scheme. Referring to the examples set forth in the previous drawings, stage 6130 may be carried out by a processor such as processor 390, and especially by a defect detection module such as defect detection module 370. In such an implementation, the detecting of the defects in stage 6140 may be based on results of the comparing of stage 6130.

As aforementioned, some or all of stages 670 through 6140 which are illustrated in FIGS. 18 and 19 may be repeated for N different wafer areas (this is illustrated by the "×N times" denotement). Those N different wafer areas may be in a single wafer or in more than one wafer. In some implementations, that process of defect detection in each of those N different wafer areas may be based directly on the calibration information obtained in stage 601 (based on the data of the reference wafer). However, in other implementations the process of defect detection in some of these N different wafer areas may be based on calibration processes previously carried out for previously processed wafer areas. For example, the defect detection in a given die in a slice of the wafer may be based on displacement and/or calibration calculations which were used for previously processed dies of the same slice in that wafer.

FIG. 20 illustrates additional stages of method 600, according to an embodiment of the invention. The stages illustrated in FIG. 20 are optional, and may be implemented in order to detect defects in each wafer area of a series of inspected wafer areas (in one or more wafers), with the help of run-time displacement values computed for another area of the series. Each of the stages illustrated in FIG. 20 is carried out—if implemented—after stage 601 is fully executed.

Optional stage 6200 includes scanning a series of multiple inspected wafer areas, each of which covers a different die (the entire die, or a portion thereof) of the same wafer. The series of other wafer area may include for example all of the die-areas in a slice, wherein each die-area covers an area from a single die (but not necessarily all of it).

Referring to the examples of FIGS. 15A and 15B, the series of gray scanned areas 120 (illustrated as gray areas) includes the portion of a single slice 150 in each of the dies 110 in a single column of the wafer 10. Referring to the stages of method 600 discussed in relation to the previous figures, it is noted that stage 6200 may include multiple instances of stage 670, executed for different inspected areas. Especially, the series of other wafer areas may include the aforementioned inspected area.

Stage 6200 may be followed, if implemented, by stage 6210 in which, for each of the inspected areas other than the first inspected area of the series, the following stages 6211, 6212, and 6213 are carried out.

Stage 6211 includes defining search windows which correspond to a subgroup which includes at least some of the database targets, wherein the defining of each of the search windows is based on a frame run-time displacement determined for a previous inspected wafer area of the series. For example, the search windows for the subgroup of a third wafer area may be defined based on the frame run-time displacement determined for the inspected area, and the search windows for the subgroup of a sixth wafer area may be defined based on the frame run-time displacement determined for a fifth wafer area (but in other implementations also—either in addition or alternatively—based on the frame run-time displacement determined for another one or more previous wafer areas of the series such as the second and/or the third wafer areas). Referring to the examples set forth in the previous drawings, stage 6211 may be carried out by a correlator such as correlator 360. It should be noted that search window in stage 6211 may be defined for other targets of the database targets, apart from those of the subgroup.

If the respective wafer area includes more than one frame, the search window may be defined based on the frame run-time displacement determined in the previous inspected wafer area for the frame in which the corresponding target is included.

Since for each inspected area of the series (with the exception of the first), the search windows are defined based on the frame run-time displacement that was determined for a previous inspected wafer area of the series, displacement values that are determined for one inspected area are used to refine the estimated location of the targets, and thereby possibly reduce the displacement error of the target location. Since the displacement errors may be smaller than would be possible without the correction, the size of the search windows may be reduced.

For example, if in the aforementioned example, a search window of 100×100 is defined for the first inspected area (in stage 680) for a 32×32 pixels sized target, even smaller windows may possibly be defined for consecutive inspected wafer areas of the series. According to an embodiment of the invention, the size of at least one of the search windows defined for the subgroup targets is smaller than the size of a search window defined for the corresponding target in the first inspected area. It should be noted that the subgroups of targets used in stage 6211 may differ between different wafer areas of the series.

Stage 6212 includes calculating a target run-time displacement for each of the targets of the subgroup, based on a correlation of the respective target image to a scanned image of the corresponding search window. While not necessarily so, the calculating of the target displacement in stage 6212 may be implemented similarly to the calculating of stage 6100. For example, it may include (or be preceded by) correlating a target image of each of the targets of the subgroup to at least a portion of a scanned image of the corresponding search window. Referring to the examples set forth in the previous drawings, stage 6212 may be carried out by a correlator such as correlator 360.

Stage 6213 includes detecting defects in that inspected wafer area of the series, wherein the detecting is responsive to at least one of the target run-time displacements. Referring to the examples set forth in the previous drawings, stage 6213 may be carried out by a processor such as processor 390, and especially by a defect detection module such as defect detection module 370. The detecting of the defects in stage 6213 may be preceded by various stages, and especially it may be preceded by stages which are based on the calculating of the target run-time displacements for each of the respective targets in stage 6212. While not necessarily so, such stages may be similar to stages 6110, 6120 and 6130, mutatis mutandis.

For example, method 600 may include, for some or all of the inspected wafer areas of the series executing the following stages, which are optional, and may be implemented in order to detect defect in the respective other wafer area with the help of one or more of the run-time displacement values calculated in stage 6212:

A stage of determining a frame run-time displacement for each of multiple run-time frames scanned in the respective inspected wafer area, based on the target run-time displacements determined for multiple targets in the respective run-time frame.

A stage of modifying a comparison scheme, which is used for defect detection, based on the run-time displacements calculated for multiple database targets. Such modifying may include updating the comparison scheme. The modifying of the comparison scheme may include, for example, modifying defect detection instructions which pertain to different areas of the respective inspected wafer area (e.g. use D2D comparison instead of C2C comparison), and/or modifying the definitions of the areas to which such instructions apply.

A stage of comparing a scanned image of at least a portion of the respective inspected wafer area to reference data, based on the modified comparison scheme.

Referring to the comparison scheme (e.g. the inspection layout), it should be noted that even if a given inspected wafer area that belongs in a first die is not required to be compared to a corresponding area of another die (e.g. in a preceding other wafer area of the series) for Die-to-Die defect detection, it may optionally be nevertheless compared to such a corresponding area, in order to update location information.

As mentioned above, in some implementations, scanning of some or all of the areas of a wafer may be executed in elongated slices, substantially parallel to each other, which are scanned serially, usually in alternating scanning direction. A slice may include portions of multiple dies, and possibly from all of the dies in a column of dies in the wafer, e.g. as illustrated in FIG. 15A. The scanning of slices may be implemented by shifting the entire wafer by moving an entire stage on which the wafer is positioned along the elongated axis of the slice (e.g. the Y-axis direction). Once the scanning of a first slice in one direction has completed, the adjacent slice may then be scanned in the opposite direction (e.g. by moving the stage in the opposite direction).

FIG. 21 illustrates additional stages of method 600, according to an embodiment of the invention. The stages illustrated in FIG. 21 are optional, and may be implemented in order to detect defects in the inspected area, if at least some of its frames are scanned in a direction other than the direction in which the respective frames of the scanned area of the wafer were scanned.

Stage 601 may include stage 602 of obtaining displacements of frames scanned in a first scanning direction, and displacements of frames scanned in a second scanning direction other than the first scanning direction. The displacements of the frames scanned in a first scanning direction may be obtained in a first displacement map, and the displacement of the frames scanned in the second scanning direction may be obtained in a second displacement map. Each of the displacement maps generated may be similar to the calibration information, but pertain only to areas of the wafer scanned in a similar scanning direction.

The scanning directions may oppose each other (or substantially oppose each other), but this is not necessarily so. While the following explanation refers to a situation in which slices are scanned in opposite directions, this may be applied (with the required modifications) to any situations in which different parts of the wafer are scanned in opposing directions.

As aforementioned, FIG. 16 illustrates scanning of wafer 100 in slices 150 of alternating scanning directions, according to an embodiment of the invention. The slices denoted 150(1) are scanned in a first direction (from top to bottom of the drawings), while the slices denoted 150(2) are scanned in the opposite direction (from bottom to top of the drawing).

Stage 601 may also include stage 603 of obtaining target information of targets in an analyzed frame, wherein the target information is based on results of a scanning of the analyzed frame in a first scanning direction.

Stage 670 that includes scanning of the inspected area may include stage 671 of scanning the inspected area which includes a frame that corresponds to the analyzed frame and is scanned in a second scanning direction which is opposite to the first scanning direction. Optionally, some or all of the scanned-wafer features in each of the run-time frames (and especially in the frame that corresponds to the analyzed frame) and in a corresponding scanned frame substantially overlap.

The defining of the search windows in such an implementation may be preceded by stage 6300 of computing an averaged displacement by averaging frame-displacements of scanned frames that are adjacent to the analyzed frame and which were scanned in the second scanning direction. While the computing may be carried out after the scanning of the inspected area (as illustrated), in other implementations it may be executed beforehand—e.g. as part of the generating in stage 660.

The defining of the search windows may be implemented as stage 681 of defining search windows which correspond to the targets of the subgroup, wherein the defining of each of the search windows is based on the averaged displacement.

Stage 681 may be followed by any combination of the aforementioned stages 690, 6100, 6110, 6120, 6130 and 6140. For example, stage 681 may be followed by calculating a target run-time displacement for each of the targets of the subgroup, based on a correlation of the respective target image to a scanned image of the corresponding search window; and detecting defects in the inspected area, wherein the detecting is responsive to at least one of the target run-time displacements.

Figure 22:
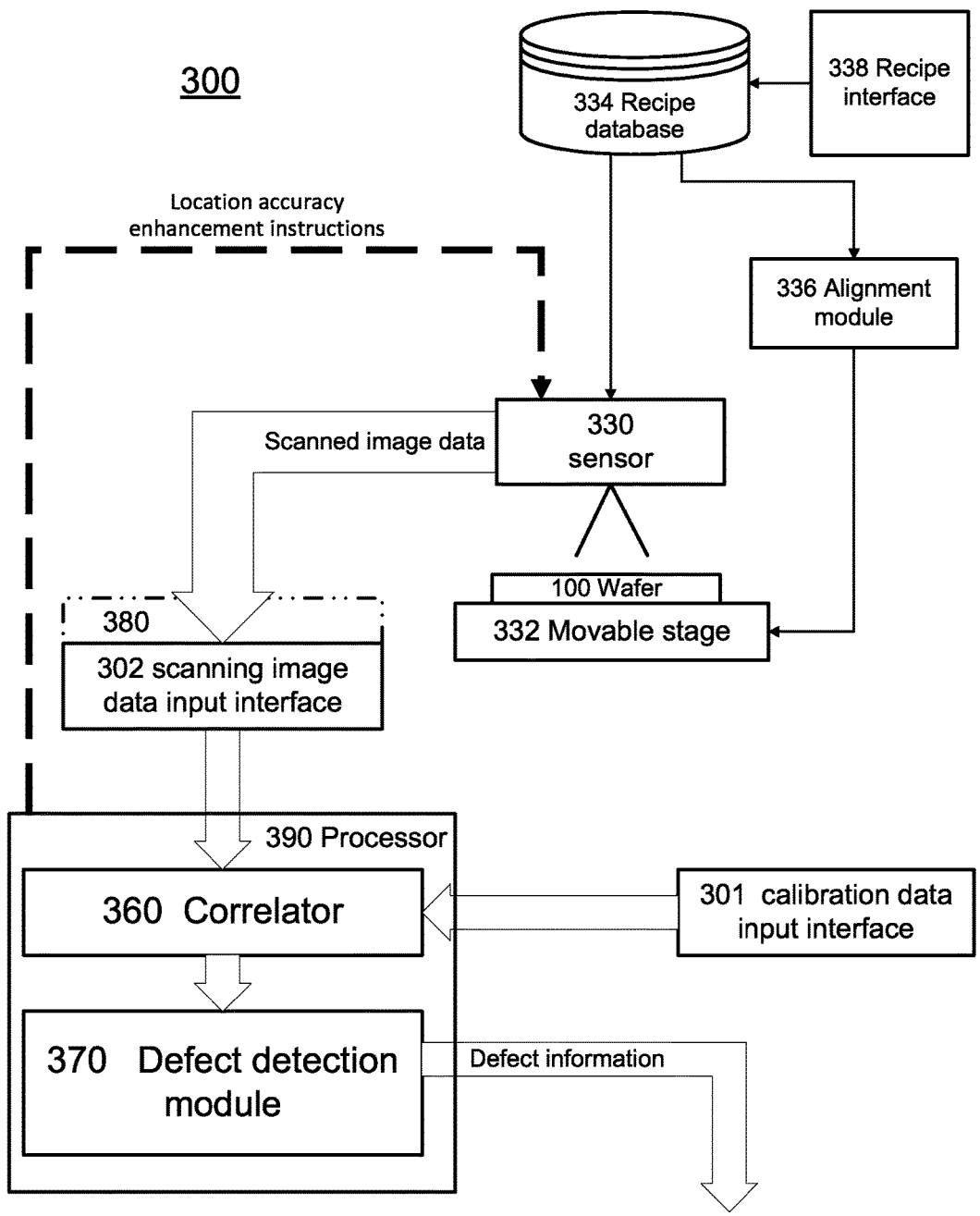
FIG. 22 illustrates a system for location based wafer analysis, according to an embodiment of the invention.

FIG. 22 illustrates system 300 for location based wafer analysis, according to an embodiment of the invention. System 300 may be combined with an inspection machine that is used to inspect the wafer (e.g. during different stages of manufacturing thereof) or connected to such a machine, but this is not necessarily so. Also, system 300 may be an inspection machine into which some or all of the modifications and/or features discussed below have been integrated.

It should be noted that, as will be clear to any person who is of skill in the art, wherever the term "wafer" is used—similar techniques, systems, methods and computer program products may be implemented for optical masks that are used for the manufacturing of wafers.

The operation of system 300 and of the various components thereof may be better understood in view of the process of operation. While not necessarily so, the process of operation of system 300 may correspond to some or all of the stages of method 600. Likewise, method 600 and its possible implementations may possibly be implemented by a system such as system 300. It is therefore noted that embodiments of the invention discussed in relation to method 600 may also be implemented, mutatis mutandis, in a hardware counterpart as various embodiments of system 300, and vice versa.

System 300 includes components which may be regarded as similar to some of the components of system 200, and which operate irrespectively of the way the calibration information and target database are implemented or generated. For clarity of discussion, similar numbering was used in the disclosure of system—wherein the first digit in the number of each component is changed from 2 to 3. That is—component 360 is similar to component 250 (though not necessarily identical or related), and so on. Therefore, for clarity and brevity of disclosure, some of the different variations, implementations and considerations which related to system 200 and its different components are not necessarily explicitly repeated in full. That is, system 300 and each of its various components may be implemented with the variations discussed in relation to the numerally corresponding component of system 200, even if not explicitly elaborated.

System 300 includes calibration data input interface 301 (also referred to as "first input interface" in the context of system 300) which is configured to obtain: (a) calibration information that includes at least displacements of multiple frames, which may consist of some or all of a plurality of frames included in a wafer area of a reference wafer, and (b) a target database that includes a target image and location information for each out of the multiple targets in each of the multiple frames.

System 300 further includes scanning image data input interface 302 (also referred to as "second input interface" in the context of system 300), that is configured to obtain scanning image data of a scan of an inspected area of an inspected wafer. While not necessarily so, input interface 302 may be similar to input interface 280, and/or combined with an input interface 380 that is similar to input interface 280.

Correlator 360 of system 300 is configured to: (a) define for each out of multiple targets of the database a search window, based on the displacement of the frame in which the target is included; (b) calculate, for each out of multiple targets, a run-time displacement, based on a correlation of the target image of the target to at least a portion of an area of the scanned image which is defined by the corresponding search window; and (c) determine a frame run-time displacement for each of multiple run-time frames scanned, based on the target run-time displacements determined for multiple targets in the respective run-time frame.

System 300 further includes processor 390, which is configured to generate inspection results for the inspected wafer, with the help of at least one of the frame run-time displacements. Processor 390 may utilize the inspection results, and/or provide them to another component and/or external system (e.g. another processor, a data storage apparatus, a display, and so on).

System 300 may include a defect detection module 370 that is configured to detect defects in the inspected area, wherein the detecting is provided with the help of at least one of the target run-time displacements. According to such an embodiment of the invention, processor 390 may be configured to generate the inspection results in response to the detected defects.

Each of correlator 360 and defect detection module 370 may be implemented by one or more hardware processors, either independent of those of the other module, or shared with it. Those modules may also include software processing modules and/or firmware processing modules. For example, some or all of those modules may be implemented on a hardware processor 390.

Calibration data input interface 301 may be configured to obtain the location information in computer aided design (CAD) coordinates.

Defect detection module 370 may be configured to report detected defects and to report location information of at least one of the defects in CAD coordinates.

Correlator 360 may be configured to: (a) determine a frame run-time displacement for each of multiple run-time frames scanned, based on the target run-time displacements determined for multiple targets in the respective run-time frame; and possibly also to (b) modify a comparison scheme based on the frame run-time displacement of the multiple run-time frames; and (c) compare an image obtained at the scanning to reference data, based on the modified comparison scheme; wherein the defect detection module is configured to detect the defects based on results of the comparing.

Scanning image data input interface 302 may be configured to receive scanning image data of a series of inspected wafer areas, each of which covers a different die, and correlator 360 may be configured to perform the following actions for each of the other wafer areas, other than the first: (a) defining search windows which correspond to a subgroup which includes at least some of the database targets, wherein the defining of each of the search windows is based on a frame run-time displacement determined for a previous inspected wafer area of the series, wherein the size of at least one of the search windows is smaller than the size of a search window defined for the corresponding target in the inspected area; (b) calculating a target run-time displacement for each of the targets of the subgroup, based on a correlation of the respective target image to a scanned image of the corresponding search window; and (c) detecting defects in the inspected wafer area, wherein the detecting is responsive to at least one of the target run-time displacements.

Calibration data input interface 301 may be configured to obtain: (a) displacements of frames scanned in a first scanning direction; (b) displacements of frames scanned in a second scanning direction other than the first scanning direction; and (c) target information of targets in an analyzed frame, wherein the target information is based on results of a scanning of the analyzed frame in a first scanning direction. Scanning image data input interface 302 may be configured to obtain scanning image data of a frame included within the inspected area which corresponds to the analyzed frame and that was scanned in the second scanning direction.

In such an implementation, correlator 360 may be further configured to: (a) compute an averaged displacement by averaging obtained frame-displacements of frames that are adjacent to the analyzed frame and whose target information of included targets is based on results of scanning in the second scanning direction; (b) define search windows which correspond to the targets of the analyzed frame, wherein the defining of each of the search windows is based on the averaged displacement; and (c) calculate a target run-time displacement for each of the targets of the analyzed frame, based on a correlation of the respective target image to a scanned image of the corresponding search window, and defect detection module 370 may be configured to detect defects in response to at least one of the target run-time displacements.

It is noted that scanning image data input interface 302 may receive the scanning image data from a sensor 330 which is part of system 300. Sensor 330, if implemented, may be is configured to scan one or more areas of the inspected wafer, including the inspected area.

System 300 may include a processor (which may be a processor 390 or another processor), which is configured to improve location accuracy of a scanning of at least one of the run-time frames (e.g. by sensor 330, or by an external sensor), based on the frame run-time displacement determined for another run-time frame. For example, such a processor may be configured to generate instructions for modifying a direction (or other parameters) of an electron beam which is used for the scanning of a given run-time frame, based on the run-time displacement of a previous frame.

Regardless of the way system 300 is implemented, it would usually include one or more components that are capable, inter alia, of processing data. For example, both correlator 360 and defect detection module 370 are capable of processing data. All such units which are capable of data processing may be implemented in hardware, software, or firmware, or any combination thereof. While in some implementations such processing capabilities may be implemented by dedicated software which is executed by general purpose processors, other implementations of the invention may require utilizing dedicated hardware or firmware, especially when volume and speed of processing of the data are of the essence.

Reverting to system 300, it will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

Reverting to method 600, it is noted that since method 600 is a computerized method, a program of instructions may be implemented, which, when executed by one or more processors, results in the execution of one of the aforementioned variations of method 600.

It would be clear to a person who is of skill in the art that instructions may be included in the program of instructions for executing some or all of the stages of method 500 (in all possible combinations suggested above), even if the inclusion of such instructions has not been explicitly elaborated.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention, as defined in the appended claims.

What is claimed is:

1. A system capable of generating calibration information usable for wafer inspection, the system comprising:
    an inspection machine usable for inspecting a wafer for detecting potential defects and/or for review thereof, and capable to obtain a scanned image of an inspected wafer area;
    a memory configured to store data obtained by the inspection machine and informative of the scanned image, the scanned image comprising multiple scanned frames;
    a processor communicatively coupled to the memory, wherein the processor is configured to:

select multiple targets in each of the multiple scanned frames, each given target being an image comprising a pattern which is identifiable within an environment of the given target in the scanned image, and wherein each given target is characterized by data informative of location of the given target in the scanned image;

calculate, for each of the multiple scanned frames, a target-displacement for each given target out the multiple targets selected in the respective scanned frame, the calculating based on a correlation of: (i) location of the given target in the scanned image, and (ii) location of the given target as defined by design data corresponding to the scanned image, wherein, for each given target, the calculated displacement is informative of displacement of location of the given target in the scanned image relative to its location defined by the design data;

determine a frame-displacement for each of the multiple scanned frames, the determining for a given scanned frame based on the target-displacements calculated for multiple targets selected in the given scanned frame; and generate: (a) calibration information corresponding to the frame-displacements determined for the multiple scanned frames, and (b) a target database that, for each given selected target, includes an image of the given target and data informative of location of the given target in the scanned image, wherein the generated calibration information and the target database are usable for wafer inspection;

an input interface configured to receive scanned image data of a second wafer area other than the inspected wafer area;

a processor-based correlator, configured to: (a) define search windows for the second wafer area, each of which corresponds to one of the database targets, wherein the defining of each of the search windows is based on the determined frame-displacement of the respective scanned frame in which the corresponding target is selected, the frame-displacement determined for the inspected area; and (b) calculate for the second wafer area a run-time target-displacement for each out of multiple database targets, based on a correlation of the respective target image to at least a portion of a scanned image of the corresponding search window; and a processor-based defect detection module, configured to detect defects in the second wafer area based on at least one of the run-time target-displacements.

2. The system according to claim 1, wherein the processor is further configured to provide data informative of location of the database targets in the scanned image in coordinates of the design data.

3. The system according to claim 1, wherein the processor is further configured to: (a) provide the target image for each of the multiple targets based on image processing of the scanned image data; and (b) define the multiple scanned frames based on image processing of the scanned image data.

4. The system according to claim 1, further comprising an output interface configured to report at least some of the defects, wherein the reporting comprises reporting location information of at least one of the defects in coordinates of the design data.

5. The system according to claim 1, wherein the correlator is configured to determine a run-time frame-displacement for each of multiple run-time frames scanned in the second wafer area, based on the run-time target-displacements determined for multiple targets in the respective run-time frame; wherein the defect detection module is further configured to modify a comparison scheme based on the run-time frame-displacement of the multiple run-time frames; and wherein the defect detection module is further configured to compare a scanned image of at least a portion of the second wafer area to reference data, based on the modified comparison scheme and to detect defects in the second wafer area based on results of the comparing.

6. The system according to claim 1, further comprising an input interface configured to receive scanning results of a scan of the inspected area of the wafer that was scanned in slices scanned in alternating scanning directions; wherein the processor is further configured to generate, as part of the calibration information, a first displacement map which includes frame-displacements of scanned frames scanned in a first scanning direction, and a second displacement map which includes frame-displacements of scanned frames scanned in a second scanning direction.

7. A computerized method of generating calibration information usable for wafer inspection, the method comprising:

upon obtaining and storing in a memory data informative of a scanned image of an inspected wafer area, the data being obtained by scanning an area of a wafer by an inspection machine usable for inspecting wafers and detecting potential defects and/or for review thereof, and the scanned image comprising multiple scanned frames, selecting multiple targets in each of the multiple scanned frames, each given target being an image comprising a pattern which is identifiable within an environment of the given target in the scanned image, and wherein each given target is characterized by data informative of location of the given target in the scanned image, the selecting provided by a processor communicatively coupled to the memory;

calculating by the processor, for each of the multiple scanned frames, a target-displacement for each given target out the multiple targets selected in the respective scanned frame, wherein, for each given target, the calculated displacement is informative of displacement of location of the given target in the scanned image relatively to its location as defined by design data corresponding to the scanned image;

determining, by the processor, a frame-displacement for each of the multiple scanned frames, the determining for a given scanned frame based on target-displacements calculated by the processor for multiple targets selected in the given scanned frame;

generating by the processor: (a) calibration information corresponding to the frame-displacements determined for the multiple scanned frames, and (b) a target database that, for each given selected target, includes an image of the given target and data informative of location of the given target in the scanned image, wherein the generated calibration information and the target database are usable for wafer inspection;

scanning a second wafer area other than the inspected area;

for each out of multiple targets of the database:
defining for the second wafer area a corresponding search window based on the frame displacement of the scanned frame in which the target is selected, the frame-displacement determined for the inspected area; and calculating for the second wafer area a run-time target-displacement for the target, based on a correlation of the target image to at least a portion of an area of the scanned image which is defined by the corresponding search window;

determining a run-time frame-displacement for each of multiple run-time frames scanned in the second wafer area, based on the run-time target-displacements determined for multiple targets in the respective run-time frame; and providing inspection results for the second wafer area based on at least one of the run-time frame-displacements.

8. The method according to claim 7, the method comprising enabling utilizing the calibration information and the target database for determining location information in an inspection of another wafer.

9. The method according to claim 7, wherein data informative of location information of the database targets are saved in computer aided design (CAD) coordinates.

10. The method according to claim 7, further comprising: scanning the inspected area of the wafer to provide scanned image data; selecting the target image for each of the multiple targets based on image processing of the scanned image data; saving the images of the multiple targets based on the selection; and defining the scanned frames based on image processing of the scanned image data.

11. The method according to claim 7, further comprising detecting defects in the second wafer area based on at least one of the run-time target-displacements, wherein the inspection results comprise results of the defect detecting.

12. The method according to claim 7, further comprising reporting defects, after detecting, wherein the reporting comprises reporting location information of at least one of the defects in coordinates of design data.

13. The method according to claim 7, further comprising: scanning, prior to calculating, the inspected area of the wafer in slices which are scanned in alternating scanning directions; wherein the generating of the calibration information comprises generating a first displacement map which includes frame-displacements of scanned frames scanned in a first scanning direction, and a second displacement map which includes frame-displacements of scanned frames scanned in a second scanning direction.

14. A program storage device comprising a non-transitory storage medium readable by a processor and tangibly embodying a computer-readable program of instructions executable by the processor that, when executed by the processor, causes the processor to perform a method of generating calibration information usable for wafer inspection, comprising the steps of:

upon obtaining and storing in a memory communicatively coupled to the processor data informative of a scanned image of an inspected wafer area, the data being obtained by scanning an area of a wafer by an inspection machine usable for inspecting a wafer and detecting potential defects and/or for review thereof, the scanned image comprising multiple scanned frames, selecting multiple targets in each of the multiple scanned frames, each given target being an image comprising a pattern which is identifiable within an environment of the given target in the scanned image, and wherein each given target is characterized by data informative of location of the given target in the scanned image;

calculating by the processor, for each of the multiple scanned frames, a target-displacement for each given target out the multiple targets selected in the respective scanned frame, wherein, for each given target, the calculated displacement is informative of displacement of location of the given target in the scanned image relatively to its location as defined by design data corresponding to the scanned image;

determining a frame-displacement for each of the multiple scanned frames, the determining for a given scanned frame based on target-displacements calculated for multiple targets selected in the given scanned frame;

generating (i) calibration information corresponding to the frame-displacements determined for the multiple scanned frames, and (ii) a target database that, for each given selected target, includes an image of the given target and data informative of location of the given target in the scanned image, wherein the generated calibration information and the target database are usable for wafer inspection;

scanning a second wafer area other than the inspected area;

for each out of multiple targets of the database:
defining for the second wafer area a corresponding search window based on the frame displacement of the scanned frame in which the target is selected, the frame-displacement determined for the inspected area; and calculating for the second wafer area a run-time target-displacement for the target, based on a correlation of the target image to at least a portion of an area of the scanned image which is defined by the corresponding search window;

determining a run-time frame-displacement for each of multiple run-time frames scanned in the second wafer area, based on the run-time target-displacements determined for multiple targets in the respective run-time frame; and providing inspection results for the second wafer area based on at least one of the run-time frame-displacements.

15. The program storage device according to claim 14, wherein the program of instructions further includes computer readable program code for causing the machine to enable utilizing the calibration information and the target database for determining location information in an inspection of another wafer.

16. The program storage device according to claim 14, wherein computer readable program code that is included in the program of instructions for causing the machine to perform the step of generating comprise instructions for saving the location information of the database targets in computer aided design (CAD) coordinates.

17. The program storage device according to claim 14, wherein the program of instructions further includes computer readable program code for causing the machine to: (a) scan the inspected area of the wafer to provide scanned image data; (b) select the target image for each of the multiple targets based on image processing of the scanned image data; (c) save the multiple scanned images based on the selection; and (d) define the scanned frames based on image processing of the scanned image data.

18. The program storage device according to claim 14, wherein the program of instructions further includes computer readable program code for causing the machine to report defects, after detecting, wherein the reporting comprises reporting location information of at least one of the defects in coordinates of design data.

* * * * *